(12) United States Patent
Ormrod et al.

(10) Patent No.: US 12,290,638 B2
(45) Date of Patent: May 6, 2025

(54) HUMIDIFIER

(71) Applicant: ResMed Pty Ltd, Bella Vista (AU)

(72) Inventors: Joseph Samuel Ormrod, Sydney (AU);
Michael James Dent, Sydney (AU);
Wei Liang Lau, Sydney (AU)

(73) Assignee: ResMed Pty Ltd, Bella Vista (AU)

( * ) Notice: Subject to any disclaimer, the term of this patent is extended or adjusted under 35 U.S.C. 154(b) by 987 days.

(21) Appl. No.: 17/357,021

(22) Filed: Jun. 24, 2021

(65) Prior Publication Data

US 2021/0316109 A1  Oct. 14, 2021

Related U.S. Application Data

(63) Continuation of application No. 15/974,758, filed on May 9, 2018, now Pat. No. 11,052,217.

(Continued)

(51) Int. Cl.
*A61M 16/16*   (2006.01)
*A61M 16/00*   (2006.01)
(Continued)

(52) U.S. Cl.
CPC ........ *A61M 16/16* (2013.01); *A61M 16/0066* (2013.01); *A61M 16/026* (2017.08);
(Continued)

(58) Field of Classification Search
CPC ............................................ A61M 16/16–165
See application file for complete search history.

(56) References Cited

U.S. PATENT DOCUMENTS 3,793,810 A   2/1974 McPhee
3,852,385 A   12/1974 Huggins
(Continued)

FOREIGN PATENT DOCUMENTS

GB         1453512 A      10/1976
WO    WO 98/004310 A1    2/1998
(Continued)

OTHER PUBLICATIONS

"*Respiratory Physiology*", by John B. West, Lippincott Williams & Wilkins, 9th edition published 2012 (8 pages).

(Continued)

*Primary Examiner* — Bradley H Philips
(74) *Attorney, Agent, or Firm* — Nixon & Vanderhye P.C.

(57) ABSTRACT

A humidifier comprises a water reservoir and a reservoir dock configured to receive the water reservoir in an operative position. The water reservoir is configured to hold a volume of liquid. The water reservoir includes a chamber and a single conduit providing an inner opening arranged within the chamber. The reservoir dock includes a dock inlet conduit arranged to receive the flow of air from the RPT device. The dock inlet conduit is structured and arranged to extend within the single conduit of the water reservoir when the water reservoir reaches the operative position such that the dock inlet conduit and the single conduit at least partially overlap one another. The dock inlet conduit includes an inner opening arranged adjacent the inner opening of the single conduit when the water reservoir reaches the operative position, the inner openings of the dock inlet conduit and the single conduit arranged to provide an inlet for the flow of air into the chamber and an outlet for delivering a humidified flow of air from the chamber.

19 Claims, 48 Drawing Sheets

Related U.S. Application Data

(60) Provisional application No. 62/507,384, filed on May 17, 2017.

(51) Int. Cl.
    *A61M 16/06* (2006.01)
    *A61M 16/08* (2006.01)
    *A61M 16/10* (2006.01)

(52) U.S. Cl.
    CPC ........ *A61M 16/06* (2013.01); *A61M 16/0816* (2013.01); *A61M 16/109* (2014.02); *A61M 2016/0027* (2013.01); *A61M 2016/0036* (2013.01); *A61M 16/1095* (2014.02); *A61M 16/164* (2014.02); *A61M 2205/18* (2013.01); *A61M 2205/3365* (2013.01); *A61M 2205/3368* (2013.01); *A61M 2205/3382* (2013.01); *A61M 2205/581* (2013.01); *A61M 2205/582* (2013.01); *A61M 2205/583* (2013.01); *A61M 2206/14* (2013.01)

(56) References Cited

U.S. PATENT DOCUMENTS

| | | | |
|---|---|---|---|
| 4,152,379 | A | 5/1979 | Suhr |
| 4,782,832 | A | 11/1988 | Trimble et al. |
| 4,944,310 | A | 7/1990 | Sullivan |
| 6,532,959 | B1 | 3/2003 | Berthon-Jones |
| 6,581,594 | B1 | 6/2003 | Drew et al. |
| 7,866,944 | B2 | 1/2011 | Kenyon et al. |
| 8,631,789 | B2 | 1/2014 | Virr et al. |
| 8,636,479 | B2 | 1/2014 | Kenyon et al. |
| 8,638,014 | B2 | 1/2014 | Sears et al. |
| 8,733,349 | B2 | 5/2014 | Bath et al. |
| 8,985,105 | B2 * | 3/2015 | Burton .................. A61M 16/16 318/400.38 |
| 2007/0079826 | A1 * | 4/2007 | Kramer ............... A61M 16/109 128/200.14 |
| 2007/0193580 | A1 | 8/2007 | Feldhahn et al. |
| 2009/0044808 | A1 | 2/2009 | Guney et al. |
| 2009/0050156 | A1 | 2/2009 | Ng et al. |
| 2009/0056712 | A1 | 3/2009 | Cortez, Jr. |
| 2009/0120434 | A1 * | 5/2009 | Smith ............... A61M 16/0075 128/202.13 |
| 2010/0000534 | A1 | 1/2010 | Kooij et al. |
| 2010/0065051 | A1 * | 3/2010 | Potharaju .............. A61M 16/16 128/203.26 |
| 2013/0146054 | A1 | 6/2013 | Ho |
| 2013/0228177 | A1 | 9/2013 | Schueller |
| 2015/0023782 | A1 | 1/2015 | Velzy et al. |
| 2018/0110955 | A1 | 4/2018 | Drew et al. |
| 2018/0333556 | A1 | 11/2018 | Ormrod et al. |

FOREIGN PATENT DOCUMENTS

| | | |
|---|---|---|
| WO | WO 98/034665 A1 | 8/1998 |
| WO | WO 2000/078381 A1 | 12/2000 |
| WO | WO 02/066106 A1 | 8/2002 |
| WO | WO 2004/073778 A1 | 9/2004 |
| WO | WO 2005/063328 A1 | 7/2005 |
| WO | WO 2006/074513 A1 | 7/2006 |
| WO | WO 2006/130903 A1 | 12/2006 |
| WO | WO 2007/045017 A2 | 4/2007 |
| WO | WO 2009/052560 A1 | 4/2009 |
| WO | WO 2010/135785 A1 | 12/2010 |
| WO | WO 2012/025846 A1 | 3/2012 |
| WO | WO 2012/171072 A1 | 12/2012 |
| WO | WO 2013/020167 A1 | 2/2013 |
| WO | WO 2014/138804 A1 | 9/2014 |
| WO | 2018/033863 A1 | 2/2018 |

OTHER PUBLICATIONS

Ormrod et al., U.S. Appl. No. 15/974,758, filed May 9, 2018, for "Humdifier," (parent application).

* cited by examiner

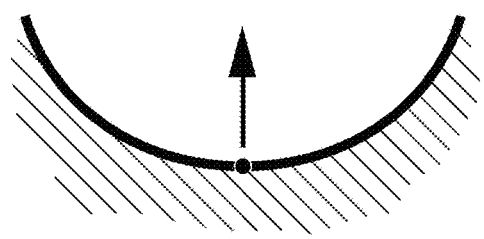
FIG. 3B — Relatively Large Positive Curvature
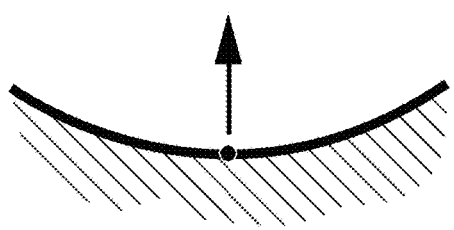
FIG. 3C — Relatively Small Positive Curvature
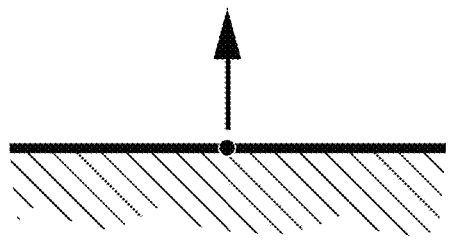
FIG. 3D — Zero Curvature
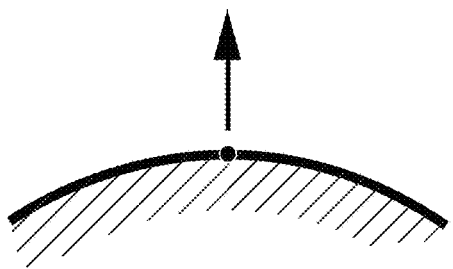
FIG. 3E — Relatively Small Negative Curvature
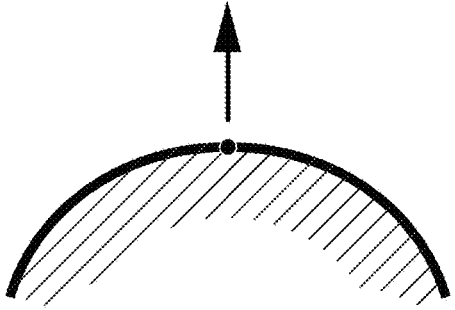
FIG. 3F — Relatively Large Negative Curvature
Copyright 2015 ResMed Limited

HUMIDIFIER

1 CROSS-REFERENCE TO RELATED APPLICATIONS

This application is a continuation of U.S. application Ser. No. 15/974,758, filed May 9, 2018, which claims the benefit of U.S. Provisional Application No. 62/507,384, filed May 17, 2017, each of which are incorporated herein by reference in their entirety.

A portion of the disclosure of this patent document contains material which is subject to copyright protection. The copyright owner has no objection to the facsimile reproduction by anyone of the patent document or the patent disclosure, as it appears in Patent Office patent files or records, but otherwise reserves all copyright rights whatsoever.

2 BACKGROUND OF THE TECHNOLOGY

2.1 Field of the Technology

The present technology relates to one or more of the detection, diagnosis, treatment, prevention and amelioration of respiratory-related disorders. The present technology also relates to medical devices or apparatus, and their use.

2.2 Description of the Related Art 2.2.1 Human Respiratory System and its Disorders The respiratory system of the body facilitates gas exchange. The nose and mouth form the entrance to the airways of a patient.

The airways include a series of branching tubes, which become narrower, shorter and more numerous as they penetrate deeper into the lung. The prime function of the lung is gas exchange, allowing oxygen to move from the inhaled air into the venous blood and carbon dioxide to move in the opposite direction. The trachea divides into right and left main bronchi, which further divide eventually into terminal bronchioles. The bronchi make up the conducting airways, and do not take part in gas exchange. Further divisions of the airways lead to the respiratory bronchioles, and eventually to the alveoli. The alveolated region of the lung is where the gas exchange takes place, and is referred to as the respiratory zone. See "*Respiratory Physiology*", by John B. West, Lippincott Williams & Wilkins, 9th edition published 2012.

A range of respiratory disorders exist. Certain disorders may be characterised by particular events, e.g. apneas, hypopneas, and hyperpneas.

Examples of respiratory disorders include Obstructive Sleep Apnea (OSA), Cheyne-Stokes Respiration (CSR), respiratory insufficiency, Obesity Hyperventilation Syndrome (OHS), Chronic Obstructive Pulmonary Disease (COPD), Neuromuscular Disease (NMD) and Chest wall disorders.

Obstructive Sleep Apnea (OSA), a form of Sleep Disordered Breathing (SDB), is characterised by events including occlusion or obstruction of the upper air passage during sleep. It results from a combination of an abnormally small upper airway and the normal loss of muscle tone in the region of the tongue, soft palate and posterior oropharyngeal wall during sleep. The condition causes the affected patient to stop breathing for periods typically of 30 to 120 seconds in duration, sometimes 200 to 300 times per night. It often causes excessive daytime somnolence, and it may cause cardiovascular disease and brain damage. The syndrome is a common disorder, particularly in middle aged overweight males, although a person affected may have no awareness of the problem. See U.S. Pat. No. 4,944,310 (Sullivan).

Cheyne-Stokes Respiration (CSR) is another form of sleep disordered breathing. CSR is a disorder of a patient's respiratory controller in which there are rhythmic alternating periods of waxing and waning ventilation known as CSR cycles. CSR is characterised by repetitive de-oxygenation and re-oxygenation of the arterial blood. It is possible that CSR is harmful because of the repetitive hypoxia. In some patients CSR is associated with repetitive arousal from sleep, which causes severe sleep disruption, increased sympathetic activity, and increased afterload. See U.S. Pat. No. 6,532,959 (Berthon-Jones).

Respiratory failure is an umbrella term for respiratory disorders in which the lungs are unable to inspire sufficient oxygen or exhale sufficient $CO_2$ to meet the patient's needs. Respiratory failure may encompass some or all of the following disorders.

A patient with respiratory insufficiency (a form of respiratory failure) may experience abnormal shortness of breath on exercise.

Obesity Hyperventilation Syndrome (OHS) is defined as the combination of severe obesity and awake chronic hypercapnia, in the absence of other known causes for hypoventilation. Symptoms include dyspnea, morning headache and excessive daytime sleepiness.

Chronic Obstructive Pulmonary Disease (COPD) encompasses any of a group of lower airway diseases that have certain characteristics in common. These include increased resistance to air movement, extended expiratory phase of respiration, and loss of the normal elasticity of the lung. Examples of COPD are emphysema and chronic bronchitis. COPD is caused by chronic tobacco smoking (primary risk factor), occupational exposures, air pollution and genetic factors. Symptoms include: dyspnea on exertion, chronic cough and sputum production.

Neuromuscular Disease (NMD) is a broad term that encompasses many diseases and ailments that impair the functioning of the muscles either directly via intrinsic muscle pathology, or indirectly via nerve pathology. Some NMD patients are characterised by progressive muscular impairment leading to loss of ambulation, being wheelchair-bound, swallowing difficulties, respiratory muscle weakness and, eventually, death from respiratory failure. Neuromuscular disorders can be divided into rapidly progressive and slowly progressive: (i) Rapidly progressive disorders: Characterised by muscle impairment that worsens over months and results in death within a few years (e.g. Amyotrophic lateral sclerosis (ALS) and Duchenne muscular dystrophy (DMD) in teenagers); (ii) Variable or slowly progressive disorders: Characterised by muscle impairment that worsens over years and only mildly reduces life expectancy (e.g. Limb girdle, Facioscapulohumeral and Myotonic muscular dystrophy). Symptoms of respiratory failure in NMD include: increasing generalised weakness, dysphagia, dyspnea on exertion and at rest, fatigue, sleepiness, morning headache, and difficulties with concentration and mood changes.

Chest wall disorders are a group of thoracic deformities that result in inefficient coupling between the respiratory muscles and the thoracic cage. The disorders are usually characterised by a restrictive defect and share the potential of long term hypercapnic respiratory failure. Scoliosis and/or kyphoscoliosis may cause severe respiratory failure. Symptoms of respiratory failure include: dyspnea on exertion, peripheral oedema, orthopnea, repeated chest infections, morning headaches, fatigue, poor sleep quality and loss of appetite.

A range of therapies have been used to treat or ameliorate such conditions. Furthermore, otherwise healthy individuals may take advantage of such therapies to prevent respiratory disorders from arising. However, these have a number of shortcomings.

2.2.2 Therapy

Various therapies, such as Continuous Positive Airway Pressure (CPAP) therapy, Non-invasive ventilation (NIV) and Invasive ventilation (IV) have been used to treat one or more of the above respiratory disorders.

Continuous Positive Airway Pressure (CPAP) therapy has been used to treat Obstructive Sleep Apnea (OSA). The mechanism of action is that continuous positive airway pressure acts as a pneumatic splint and may prevent upper airway occlusion, such as by pushing the soft palate and tongue forward and away from the posterior oropharyngeal wall. Treatment of OSA by CPAP therapy may be voluntary, and hence patients may elect not to comply with therapy if they find devices used to provide such therapy one or more of: uncomfortable, difficult to use, expensive and aesthetically unappealing.

Non-invasive ventilation (NIV) provides ventilatory support to a patient through the upper airways to assist the patient breathing and/or maintain adequate oxygen levels in the body by doing some or all of the work of breathing. The ventilatory support is provided via a non-invasive patient interface. NIV has been used to treat CSR and respiratory failure, in forms such as OHS, COPD, NMD and Chest Wall disorders. In some forms, the comfort and effectiveness of these therapies may be improved.

Invasive ventilation (IV) provides ventilatory support to patients that are no longer able to effectively breathe themselves and may be provided using a tracheostomy tube. In some forms, the comfort and effectiveness of these therapies may be improved.

2.2.3 Treatment Systems

These therapies may be provided by a treatment system or device. Such systems and devices may also be used to diagnose a condition without treating it.

A treatment system may comprise a Respiratory Pressure Therapy Device (RPT device), an air circuit, a humidifier, a patient interface, and data management.

Another form of treatment system is a mandibular repositioning device.

2.2.3.1 Patient Interface

A patient interface may be used to interface respiratory equipment to its wearer, for example by providing a flow of air to an entrance to the airways. The flow of air may be provided via a mask to the nose and/or mouth, a tube to the mouth or a tracheostomy tube to the trachea of a patient. Depending upon the therapy to be applied, the patient interface may form a seal, e.g., with a region of the patient's face, to facilitate the delivery of gas at a pressure at sufficient variance with ambient pressure to effect therapy, e.g., at a positive pressure of about 10 cmH$_2$O relative to ambient pressure. For other forms of therapy, such as the delivery of oxygen, the patient interface may not include a seal sufficient to facilitate delivery to the airways of a supply of gas at a positive pressure of about 10 cmH$_2$O.

Certain other mask systems may be functionally unsuitable for the present field. For example, purely ornamental masks may be unable to maintain a suitable pressure. Mask systems used for underwater swimming or diving may be configured to guard against ingress of water from an external higher pressure, but not to maintain air internally at a higher pressure than ambient.

Certain masks may be clinically unfavourable for the present technology e.g. if they block airflow via the nose and only allow it via the mouth.

Certain masks may be uncomfortable or impractical for the present technology if they require a patient to insert a portion of a mask structure in their mouth to create and maintain a seal via their lips.

Certain masks may be impractical for use while sleeping, e.g. for sleeping while lying on one's side in bed with a head on a pillow.

The design of a patient interface presents a number of challenges. The face has a complex three-dimensional shape. The size and shape of noses and heads varies considerably between individuals. Since the head includes bone, cartilage and soft tissue, different regions of the face respond differently to mechanical forces. The jaw or mandible may move relative to other bones of the skull. The whole head may move during the course of a period of respiratory therapy.

As a consequence of these challenges, some masks suffer from being one or more of obtrusive, aesthetically undesirable, costly, poorly fitting, difficult to use, and uncomfortable especially when worn for long periods of time or when a patient is unfamiliar with a system. Wrongly sized masks can give rise to reduced compliance, reduced comfort and poorer patient outcomes. Masks designed solely for aviators, masks designed as part of personal protection equipment (e.g. filter masks), SCUBA masks, or for the administration of anaesthetics may be tolerable for their original application, but nevertheless such masks may be undesirably uncomfortable to be worn for extended periods of time, e.g., several hours. This discomfort may lead to a reduction in patient compliance with therapy. This is even more so if the mask is to be worn during sleep.

CPAP therapy is highly effective to treat certain respiratory disorders, provided patients comply with therapy. If a mask is uncomfortable, or difficult to use a patient may not comply with therapy. Since it is often recommended that a patient regularly wash their mask, if a mask is difficult to clean (e.g., difficult to assemble or disassemble), patients may not clean their mask and this may impact on patient compliance.

While a mask for other applications (e.g. aviators) may not be suitable for use in treating sleep disordered breathing, a mask designed for use in treating sleep disordered breathing may be suitable for other applications.

For these reasons, patient interfaces for delivery of CPAP during sleep form a distinct field.

2.2.3.2 Respiratory Pressure Therapy (RPT) Device

A respiratory pressure therapy (RPT) device may be used to deliver one or more of a number of therapies described above, such as by generating a flow of air for delivery to an entrance to the airways. The flow of air may be pressurised. Examples of RPT devices include a CPAP device and a ventilator.

Air pressure generators are known in a range of applications, e.g. industrial-scale ventilation systems. However, air pressure generators for medical applications have particular requirements not fulfilled by more generalised air pressure generators, such as the reliability, size and weight requirements of medical devices. In addition, even devices designed for medical treatment may suffer from shortcomings, pertaining to one or more of: comfort, noise, ease of use, efficacy, size, weight, manufacturability, cost, and reliability.

An example of the special requirements of certain RPT devices is acoustic noise.

Table of noise output levels of prior RPT devices (one specimen only, measured using test method specified in ISO 3744 in CPAP mode at 10 cmH$_2$O).

| RPT Device name | A-weighted sound pressure level dB(A) | Year (approx.) |
|---|---|---|
| C-Series Tango ™ | 31.9 | 2007 |
| C-Series Tango ™ with Humidifier | 33.1 | 2007 |
| S8 Escape ™ II | 30.5 | 2005 |
| S8 Escape ™ II with H4i ™ Humidifier | 31.1 | 2005 |
| S9 AutoSet ™ | 26.5 | 2010 |
| S9 AutoSet ™ with H5i Humidifier | 28.6 | 2010 |

One known RPT device used for treating sleep disordered breathing is the S9 Sleep Therapy System, manufactured by ResMed Limited. Another example of an RPT device is a ventilator. Ventilators such as the ResMed Stellar™ Series of Adult and Paediatric Ventilators may provide support for invasive and non-invasive non-dependent ventilation for a range of patients for treating a number of conditions such as but not limited to NMD, OHS and COPD.

The ResMed Elisée™ 150 ventilator and ResMed VS III™ ventilator may provide support for invasive and non-invasive dependent ventilation suitable for adult or paediatric patients for treating a number of conditions. These ventilators provide volumetric and barometric ventilation modes with a single or double limb circuit.

RPT devices typically comprise a pressure generator, such as a motor-driven blower or a compressed gas reservoir, and are configured to supply a flow of air to the airway of a patient. In some cases, the flow of air may be supplied to the airway of the patient at positive pressure. The outlet of the RPT device is connected via an air circuit to a patient interface such as those described above.

RPT devices typically also include an inlet filter, various sensors, and a microprocessor-based controller. A blower may include a servo-controlled motor, a volute, and an impeller. In some cases a brake for the motor may be implemented to more rapidly reduce the speed of the blower so as to overcome the inertia of the motor and impeller. The braking can permit the blower to more rapidly achieve a lower pressure condition in time for synchronization with expiration despite the inertia. In some cases the pressure generator may also include a valve capable of discharging generated air to atmosphere as a means for altering the pressure delivered to the patient as an alternative to motor speed control. The sensors measure, amongst other things, motor speed, mass flow rate and outlet pressure, such as with a pressure transducer or the like. The controller may include data storage capacity with or without integrated data retrieval and display functions.

The designer of a device may be presented with an infinite number of choices to make. Design criteria often conflict, meaning that certain design choices are far from routine or inevitable. Furthermore, the comfort and efficacy of certain aspects may be highly sensitive to small, subtle changes in one or more parameters.

2.2.3.3 Humidifier

Delivery of a flow of air without humidification may cause drying of airways. The use of a humidifier with an RPT device and the patient interface produces humidified gas that minimizes drying of the nasal mucosa and increases patient airway comfort. In addition in cooler climates, warm air applied generally to the face area in and about the patient interface is more comfortable than cold air.

Respiratory humidifiers are available in many forms and may be a standalone device that is coupled to an RPT device via an air circuit, is integrated with the RPT device or configured to be directly coupled to the relevant RPT device. While known passive humidifiers can provide some relief, generally a heated humidifier may be used to provide sufficient humidity and temperature to the air so that the patient will be comfortable. Humidifiers typically comprise a water reservoir or tub having a capacity of several hundred milliliters (ml), a heating element for heating the water in the reservoir, a control to enable the level of humidification to be varied, a gas inlet to receive gas from the flow generator or RPT device, and a gas outlet adapted to be connected to an air circuit that delivers the humidified gas to the patient interface.

Heated passover humidification is one common form of humidification used with an RPT device. In such humidifiers the heating element may be incorporated in a heater plate which sits under, and is in thermal contact with, the water tub. Thus, heat is transferred from the heater plate to the water reservoir primarily by conduction. The air flow from the RPT device passes over the heated water in the water tub resulting in water vapour being taken up by the air flow. The ResMed H4i™ and H5i™ Humidifiers are examples of such heated passover humidifiers that are used in combination with ResMed S8 and S9 CPAP devices respectively.

Other humidifiers may also be used such as a bubble or diffuser humidifier, a jet humidifier or a wicking humidifier. In a bubble or diffuser humidifier the air is conducted below the surface of the water and allowed to bubble back to the top. A jet humidifier produces an aerosol of water and baffles or filters may be used so that the particles are either removed or evaporated before leaving the humidifier. A wicking humidifier uses a water absorbing material, such as sponge or paper, to absorb water by capillary action. The water absorbing material is placed within or adjacent at least a portion of the air flow path to allow evaporation of the water in the absorbing material to be taken up into the air flow.

An alternative form of humidification is provided by the ResMed HumiCare™ D900 humidifier that uses a Counter-Stream™ technology that directs the air flow over a large surface area in a first direction whilst supplying heated water to the large surface area in a second opposite direction. The ResMed HumiCare™ D900 humidifier may be used with a range of invasive and non-invasive ventilators.

A range of artificial humidification devices and systems are known, however they may not fulfil the specialised requirements of a medical humidifier.

Medical humidifiers are used to increase humidity and/or temperature of the flow of air in relation to ambient air when required, typically where the patient may be asleep or resting (e.g. at a hospital). A medical humidifier for bedside placement may be small. A medical humidifier may be configured to only humidify and/or heat the flow of air delivered to the patient without humidifying and/or heating the patient's surroundings. Room-based systems (e.g. a sauna, an air conditioner, or an evaporative cooler), for example, may also humidify air that is breathed in by the patient, however those systems would also humidify and/or heat the entire room, which may cause discomfort to the occupants. Furthermore medical humidifiers may have more stringent safety constraints than industrial humidifiers.

While a number of medical humidifiers are known, they can suffer from one or more shortcomings. Some medical humidifiers may provide inadequate humidification, some are difficult or inconvenient to use by patients.

2.2.3.4 Data Management

There may be clinical reasons to obtain data to determine whether the patient prescribed with respiratory therapy has been "compliant", e.g. that the patient has used their RPT device according to certain a "compliance rule". One example of a compliance rule for CPAP therapy is that a patient, in order to be deemed compliant, is required to use the RPT device for at least four hours a night for at least 21 of 30 consecutive days. In order to determine a patient's compliance, a provider of the RPT device, such as a health care provider, may manually obtain data describing the patient's therapy using the RPT device, calculate the usage over a predetermined time period, and compare with the compliance rule. Once the health care provider has determined that the patient has used their RPT device according to the compliance rule, the health care provider may notify a third party that the patient is compliant.

There may be other aspects of a patient's therapy that would benefit from communication of therapy data to a third party or external system.

Existing processes to communicate and manage such data can be one or more of costly, time-consuming, and error-prone.

3 BRIEF SUMMARY OF THE TECHNOLOGY

The present technology is directed towards providing medical devices used in the diagnosis, amelioration, treatment, or prevention of respiratory disorders having one or more of improved comfort, cost, efficacy, ease of use and manufacturability.

A first aspect of the present technology relates to apparatus used in the diagnosis, amelioration, treatment or prevention of a respiratory disorder.

Another aspect of the present technology relates to methods used in the diagnosis, amelioration, treatment or prevention of a respiratory disorder.

An aspect of certain forms of the present technology is to provide methods and/or apparatus that improve the compliance of patients with respiratory therapy.

Another aspect of one form of the present technology relates to humidifier to change the absolute humidity of a flow of air from an RPT device for delivery to an entrance of the airways of a patient, the change being compared to the absolute humidity of ambient air. The humidifier includes a water reservoir and a reservoir dock configured to receive the water reservoir in an operative position. The water reservoir is configured to hold a volume of liquid. The water reservoir includes a chamber and a single conduit providing an inner opening arranged within the chamber. The reservoir dock includes a dock inlet conduit arranged to receive the flow of air from the RPT device. The dock inlet conduit is structured and arranged to extend within the single conduit of the water reservoir when the water reservoir reaches the operative position such that the dock inlet conduit and the single conduit at least partially overlap one another. The dock inlet conduit includes an inner opening arranged adjacent the inner opening of the single conduit when the water reservoir reaches the operative position. The inner openings of the dock inlet conduit and the single conduit are arranged to provide an inlet for the flow of air into the chamber and an outlet for delivering a humidified flow of air from the chamber.

In an example, the inner openings of the dock inlet conduit and the single conduit are arranged at or near a geometric center of the chamber. In an example, the inner openings of the dock inlet conduit and the single conduit are arranged within at least about 6-11 mm of a geometric center of the chamber. In an example, the single conduit and inner opening thereof are arranged to form an air lock to prevent further ingress of liquid into the water reservoir when a predetermined maximum volume of liquid is reached. In an example, the single conduit and inner opening thereof are arranged such that liquid spills out through the single conduit when the predetermined maximum volume of liquid is reached. In an example, the single conduit and inner opening thereof are arranged to prevent egress of liquid from the water reservoir when the water reservoir is rotated by 90 degrees to 180 degrees in any direction from its normal working orientation. In an example, the inner openings of the dock inlet conduit and the single conduit are arranged to face the liquid in the water reservoir. In an example, the reservoir dock includes a heater plate structured and arranged to thermally contact a conductive portion provided to the water reservoir. In an example, the water reservoir includes a reservoir base and a reservoir lid removably coupled to the reservoir base, the reservoir lid including the single conduit. In an example, the dock inlet conduit and the single conduit each include a non-circular cross-sectional shape. In an example, the dock inlet conduit includes an interior surface that forms an inlet flow path into the chamber, and the dock inlet conduit includes an exterior surface that cooperates with an interior surface of the single conduit to form an outlet flow path from the chamber. In an example, when seen in a cross-section, the dock inlet conduit forms an inlet cross-sectional area for the inlet flow path and the dock inlet conduit and the single conduit cooperate to form an outlet cross-sectional area for the outlet flow path. In an example, it is preferable if the hydraulic resistance of the inlet flow path and the outlet flow path are substantially the same, or at least similar. In an example, the reservoir dock further comprises a dock outlet conduit arranged to deliver the humidified flow of air to an air circuit. In an example, the reservoir dock further comprises a conduit portion communicated with the dock outlet conduit, the conduit portion structured and arranged to engage the single conduit when the water reservoir reaches the operative position and establish a flow path for the humidified flow of air from the chamber to the dock outlet conduit. In an example, the single conduit of the water reservoir includes a seal arranged to engage the conduit portion when the water reservoir reaches the operative position. In an example, the water reservoir includes a baffle plate to enhance moisture pickup by the flow of air passing through the water reservoir. In an example, the water reservoir includes a reservoir base and a reservoir lid removably coupled to the reservoir base, the reservoir lid including the single conduit and the baffle plate. In an example, the baffle plate and the single conduit comprise a one-piece construction. In an example, the baffle plate includes a curvature along at least one of its width and its length such that the baffle plate is arranged to curve downwardly towards a reservoir base of the water reservoir.

Another aspect of one form of the present technology relates to humidifier to change the absolute humidity of a flow of air from an RPT device for delivery to an entrance of the airways of a patient, the change being compared to the absolute humidity of ambient air. The humidifier includes a water reservoir and a reservoir dock configured to receive the water reservoir in an operative position. The water reservoir is configured to hold a volume of liquid. The water reservoir includes a chamber and a single conduit extending into the chamber. The reservoir dock includes a dock inlet conduit arranged to receive the flow of air from the RPT device. The dock inlet conduit is structured and arranged to extend within the single conduit of the water reservoir when the water reservoir reaches the operative position such that the dock inlet conduit and the single conduit at least partially overlap one another. The dock inlet conduit and the single conduit are arranged to provide an inlet for the flow of air into the chamber and an outlet for delivering a humidified flow of air from the chamber. The water reservoir includes a baffle plate to enhance moisture pickup by the flow of air passing through the water reservoir.

An aspect of certain forms of the present technology is a medical device that is easy to use, e.g. by a person who does not have medical training, by a person who has limited dexterity, vision or by a person with limited experience in using this type of medical device.

An aspect of one form of the present technology is a portable RPT device that may be carried by a person, e.g., around the home of the person.

An aspect of one form of the present technology is a humidifier tank that may be washed in a home of a patient, e.g., in soapy water, without requiring specialised cleaning equipment.

Of course, portions of the aspects may form sub-aspects of the present technology. Also, various ones of the sub-aspects and/or aspects may be combined in various manners and also constitute additional aspects or sub-aspects of the present technology.

Other features of the technology will be apparent from consideration of the information contained in the following detailed description, abstract, drawings and claims.

4 BRIEF DESCRIPTION OF THE DRAWINGS

The present technology is illustrated by way of example, and not by way of limitation, in the figures of the accompanying drawings, in which like reference numerals refer to similar elements including:

4.1 Treatment Systems

FIG. 1A shows a system including a patient 1000 wearing a patient interface 3000, in the form of nasal pillows, receiving a supply of air at positive pressure from an RPT device 4000. Air from the RPT device 4000 is humidified in a humidifier 5000, and passes along an air circuit 4170 to the patient 1000. A bed partner 1100 is also shown. The patient is sleeping in a supine sleeping position.

FIG. 1B shows a system including a patient 1000 wearing a patient interface 3000, in the form of a nasal mask, receiving a supply of air at positive pressure from an RPT device 4000. Air from the RPT device is humidified in a humidifier 5000, and passes along an air circuit 4170 to the patient 1000.

FIG. 1C shows a system including a patient 1000 wearing a patient interface 3000, in the form of a full-face mask, receiving a supply of air at positive pressure from an RPT device 4000. Air from the RPT device is humidified in a humidifier 5000, and passes along an air circuit 4170 to the patient 1000. The patient is sleeping in a side sleeping position.

4.2 Respiratory System and Facial Anatomy

4.3 Patient Interface

Figure 1A:
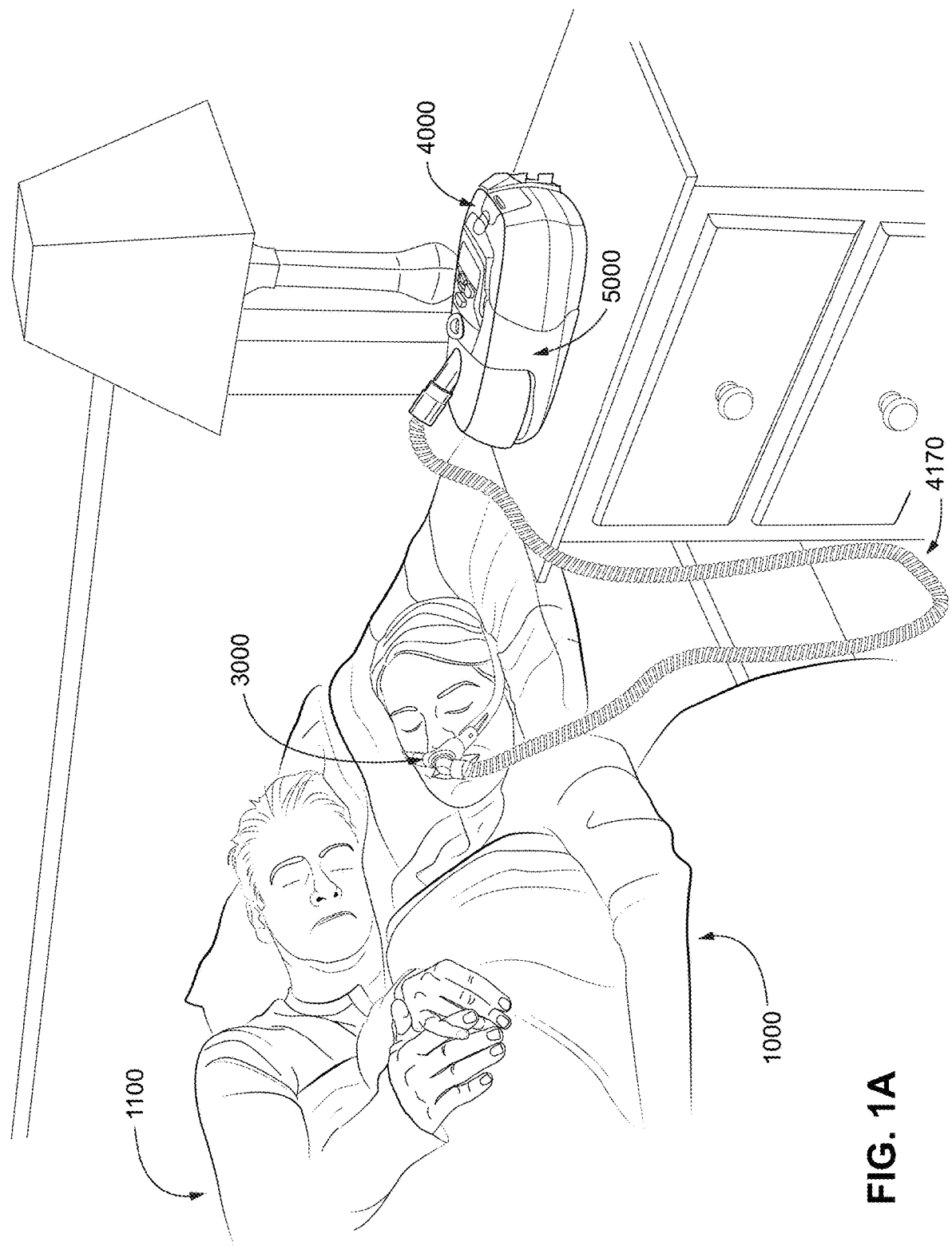
Figure 1B:
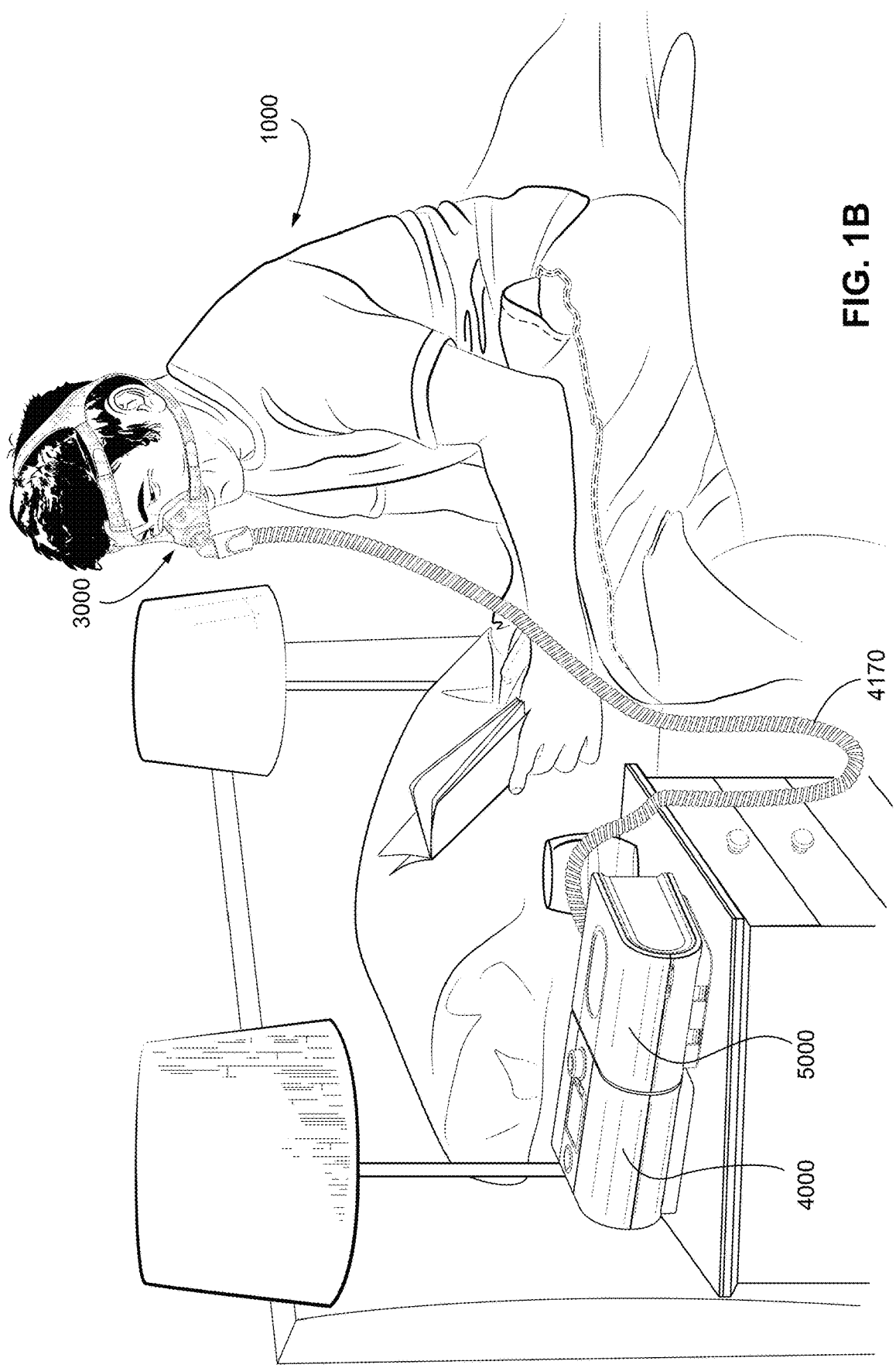
Figure 1C:
Figure 2A:
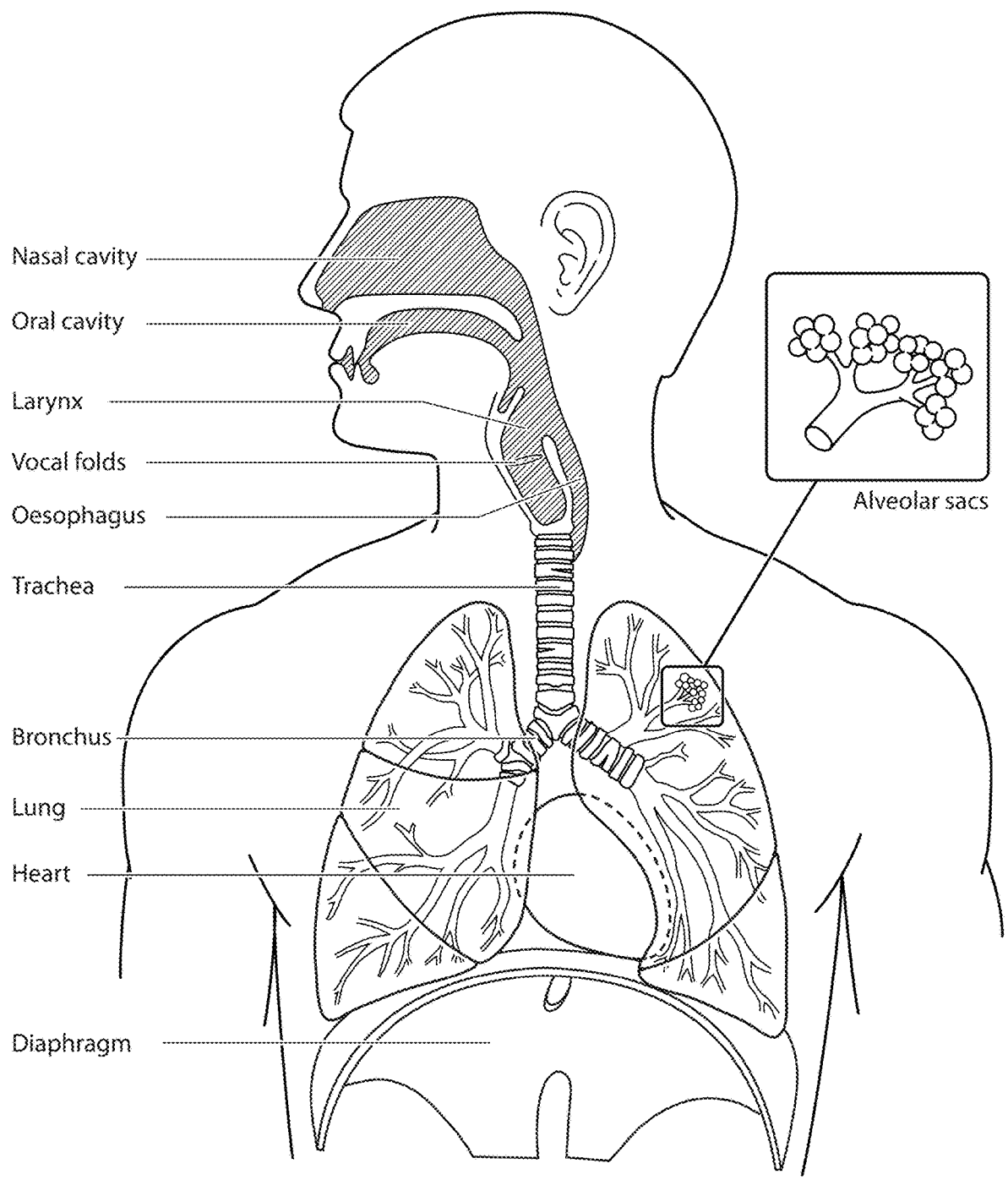
FIG. 2A shows an overview of a human respiratory system including the nasal and oral cavities, the larynx, vocal folds, oesophagus, trachea, bronchus, lung, alveolar sacs, heart and diaphragm.
Figure 2B:
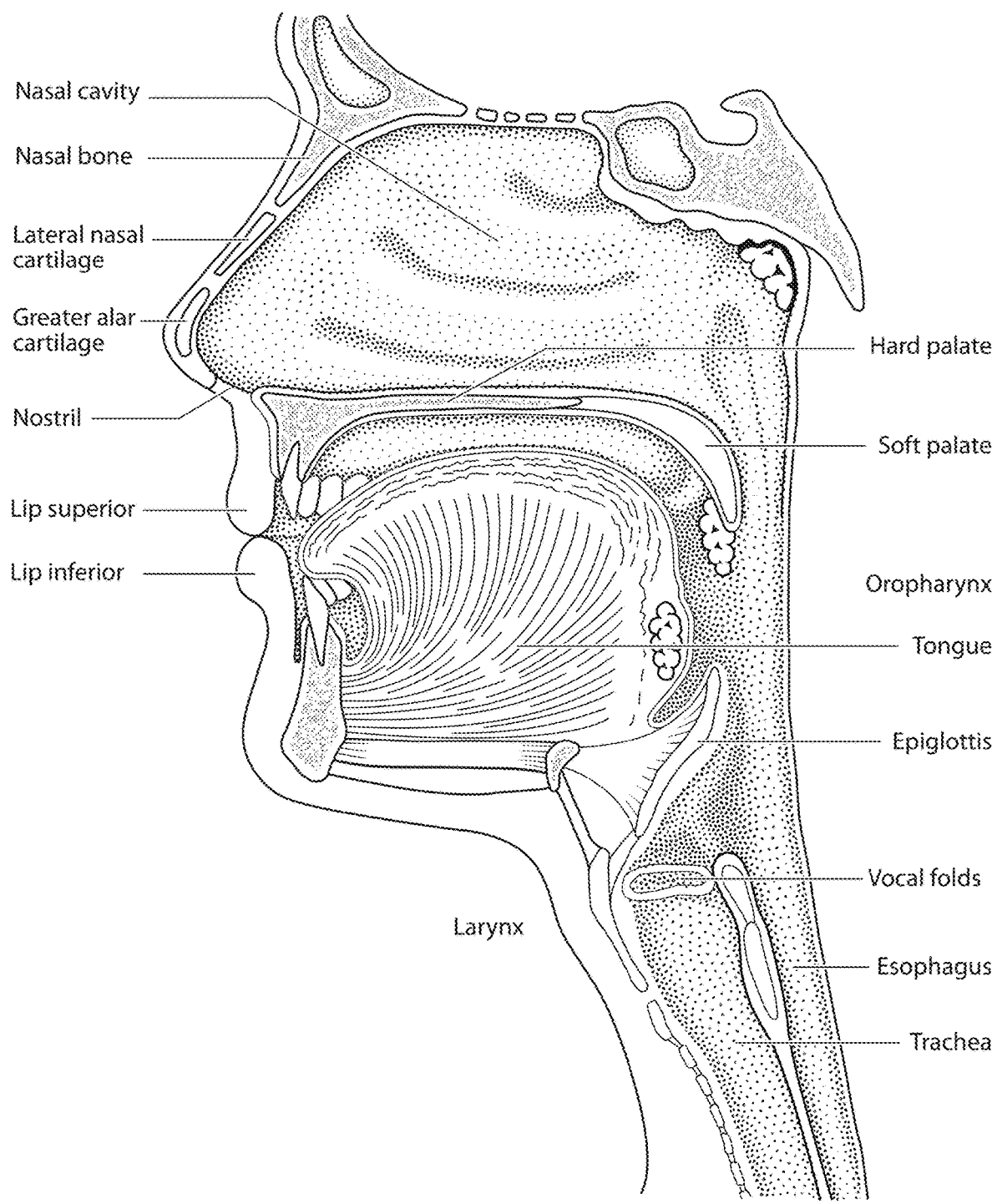
FIG. 2B shows a view of a human upper airway including the nasal cavity, nasal bone, lateral nasal cartilage, greater alar cartilage, nostril, lip superior, lip inferior, larynx, hard palate, soft palate, oropharynx, tongue, epiglottis, vocal folds, oesophagus and trachea.
Figure 3A:
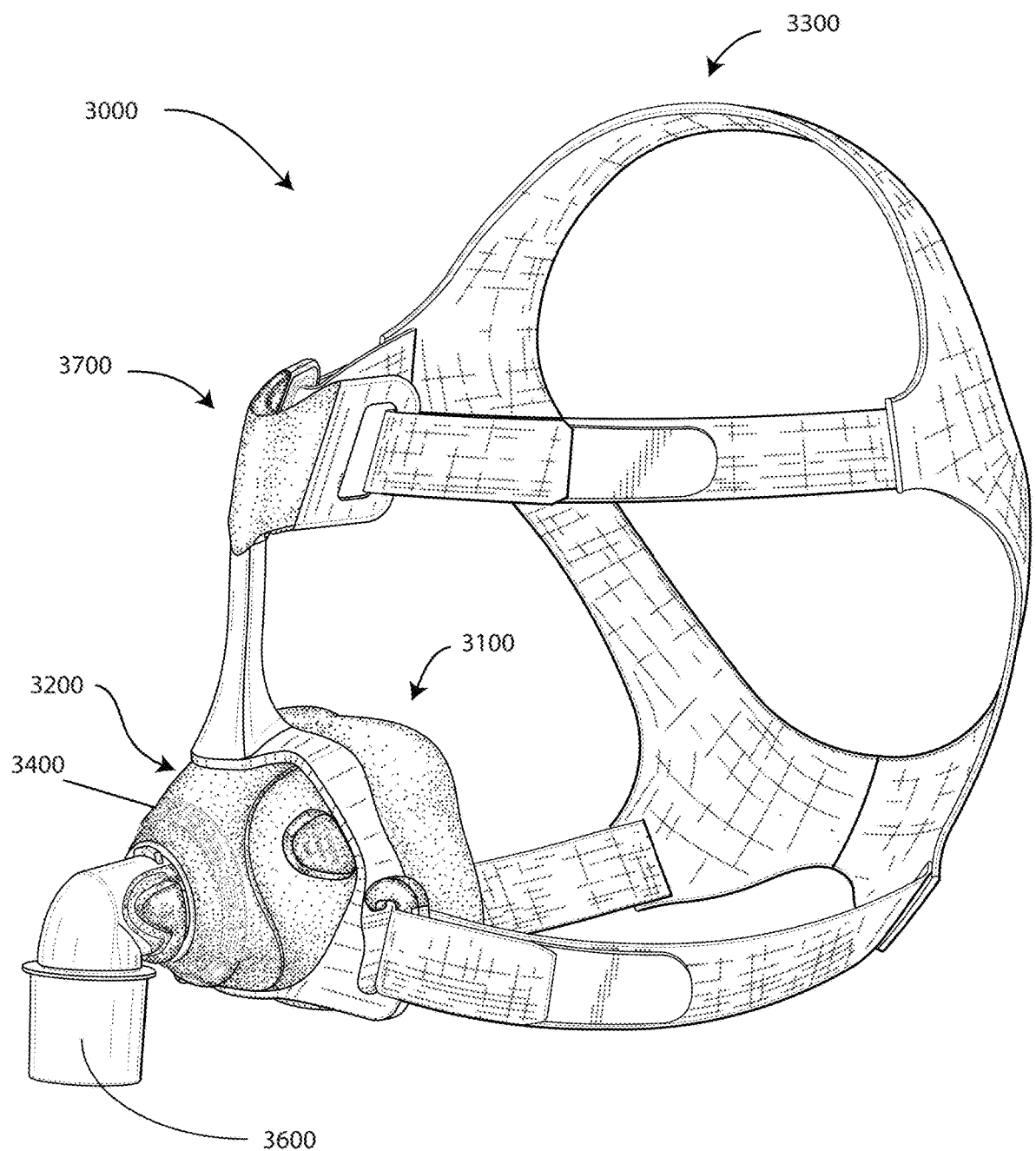

FIG. 3A shows a patient interface in the form of a nasal mask in accordance with one form of the present technology.

FIG. 3B shows a schematic of a cross-section through a structure at a point. An outward normal at the point is indicated. The curvature at the point has a positive sign, and a relatively large magnitude when compared to the magnitude of the curvature shown in FIG. 3C.

FIG. 3C shows a schematic of a cross-section through a structure at a point. An outward normal at the point is indicated. The curvature at the point has a positive sign, and a relatively small magnitude when compared to the magnitude of the curvature shown in FIG. 3B.

FIG. 3D shows a schematic of a cross-section through a structure at a point. An outward normal at the point is indicated. The curvature at the point has a value of zero.

FIG. 3E shows a schematic of a cross-section through a structure at a point. An outward normal at the point is indicated. The curvature at the point has a negative sign, and a relatively small magnitude when compared to the magnitude of the curvature shown in FIG. 3F.

FIG. 3F shows a schematic of a cross-section through a structure at a point. An outward normal at the point is indicated. The curvature at the point has a negative sign, and a relatively large magnitude when compared to the magnitude of the curvature shown in FIG. 3E.

Figure 3G:
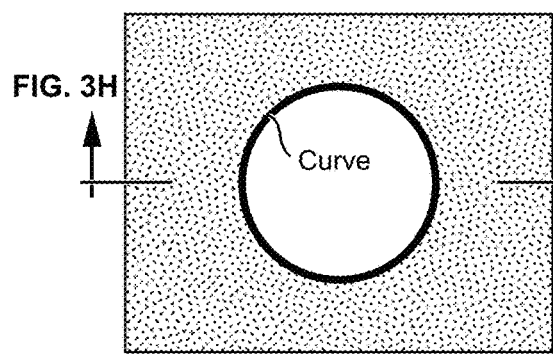

FIG. 3G shows the surface of a structure, with a one dimensional hole in the surface. The illustrated plane curve forms the boundary of a one dimensional hole.

Figure 3H:
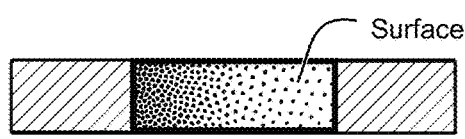

FIG. 3H shows a cross-section through the structure of FIG. 3G. The illustrated surface bounds a two dimensional hole in the structure of FIG. 3G.

Figure 3I:
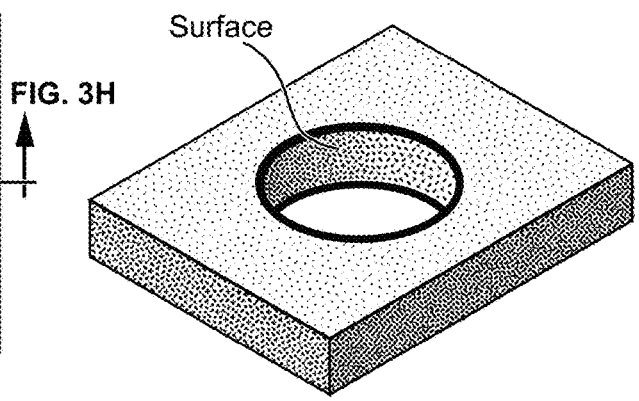

FIG. 3I shows a perspective view of the structure of FIG. 3G, including the two dimensional hole and the one dimensional hole. Also shown is the surface that bounds a two dimensional hole in the structure of FIG. 3G.

4.4 RPT Device

Figure 4A:
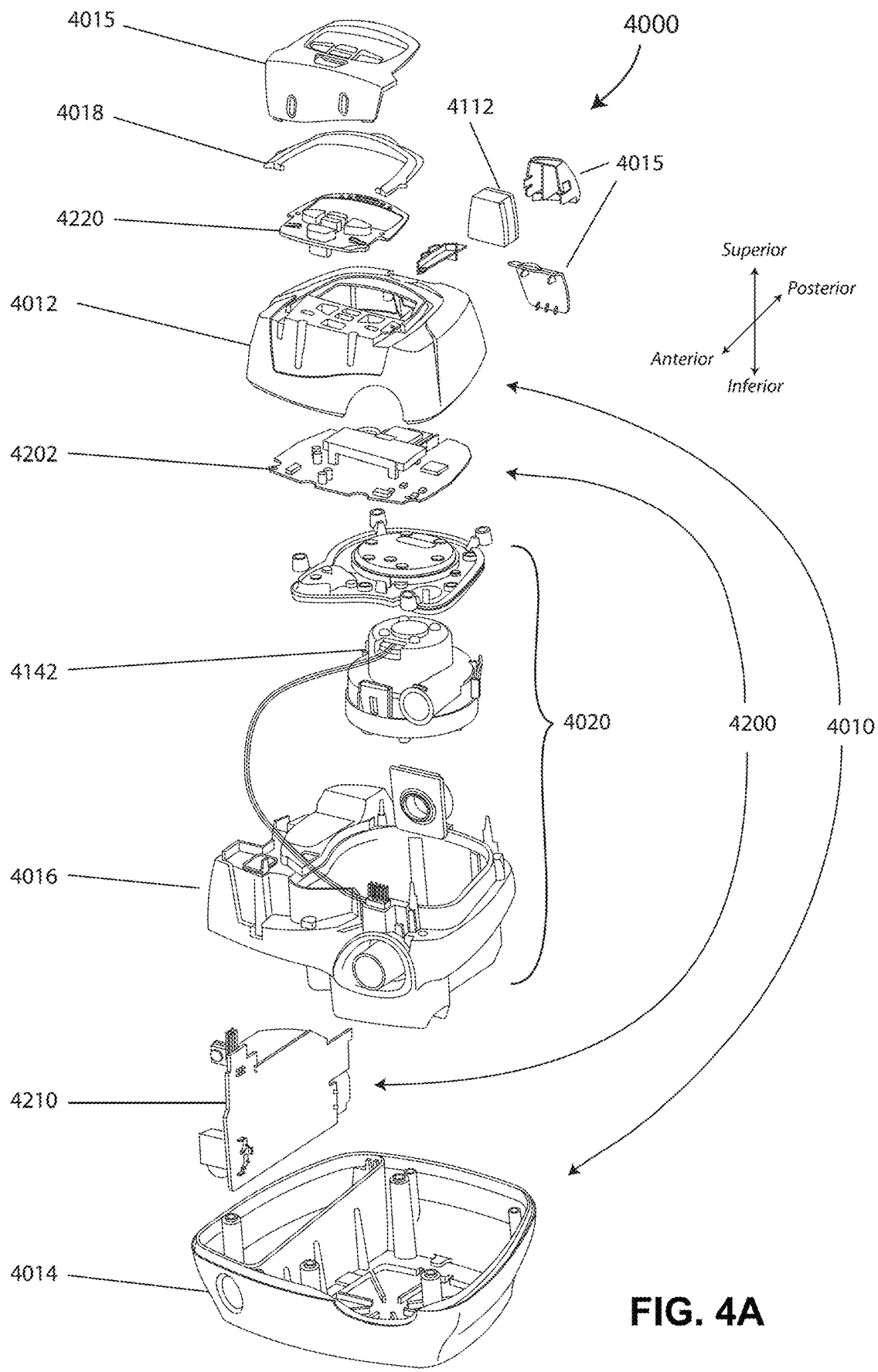

FIG. 4A shows an RPT device in accordance with one form of the present technology.

Figure 4B:
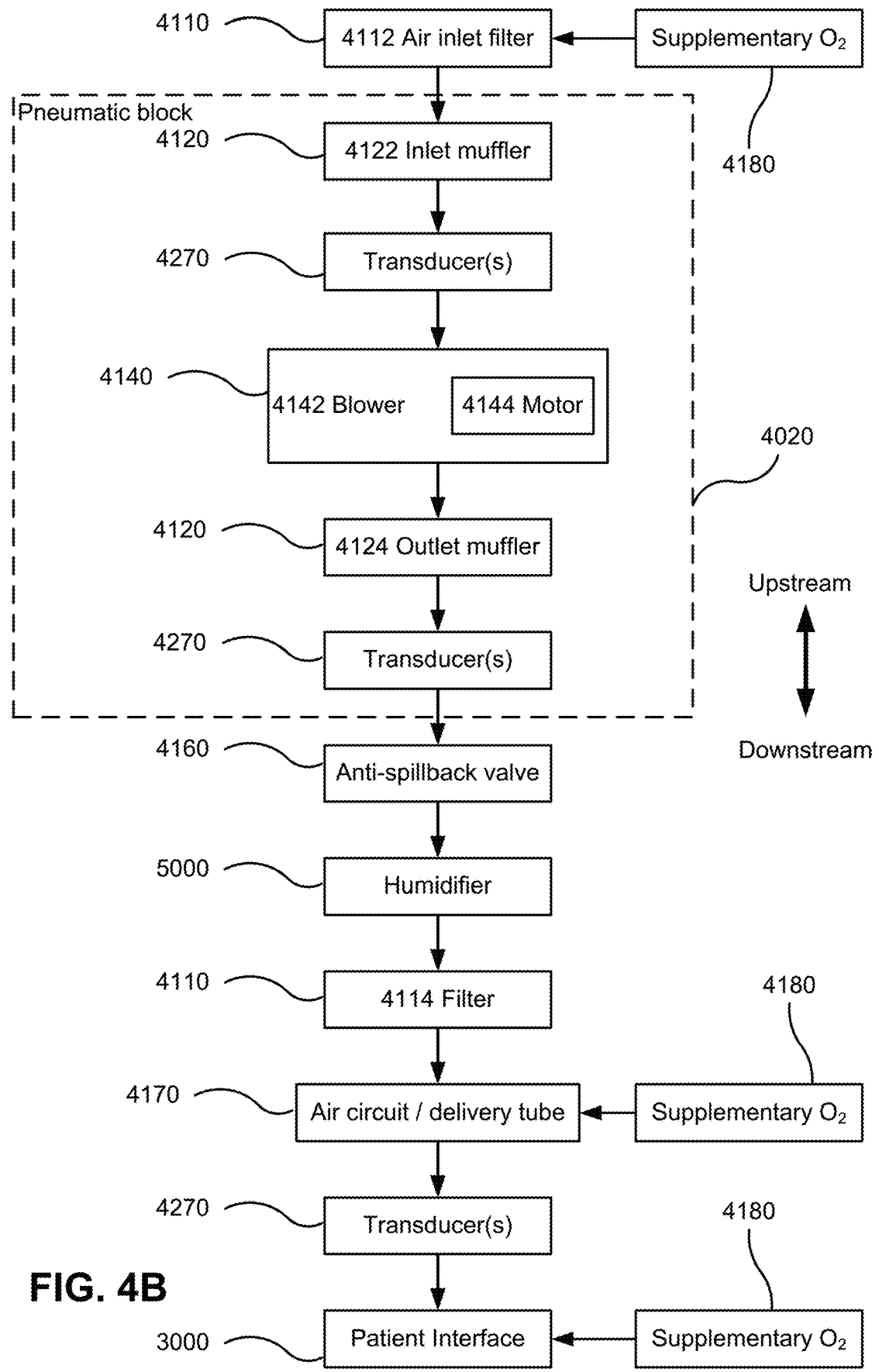

FIG. 4B is a schematic diagram of the pneumatic path of an RPT device in accordance with one form of the present technology. The directions of upstream and downstream are indicated with reference to the blower and the patient interface. The blower is defined to be upstream of the patient interface and the patient interface is defined to be downstream of the blower, regardless of the actual flow direction at any particular moment. Items which are located within the pneumatic path between the blower and the patient interface are downstream of the blower and upstream of the patient interface.

Figure 4C:
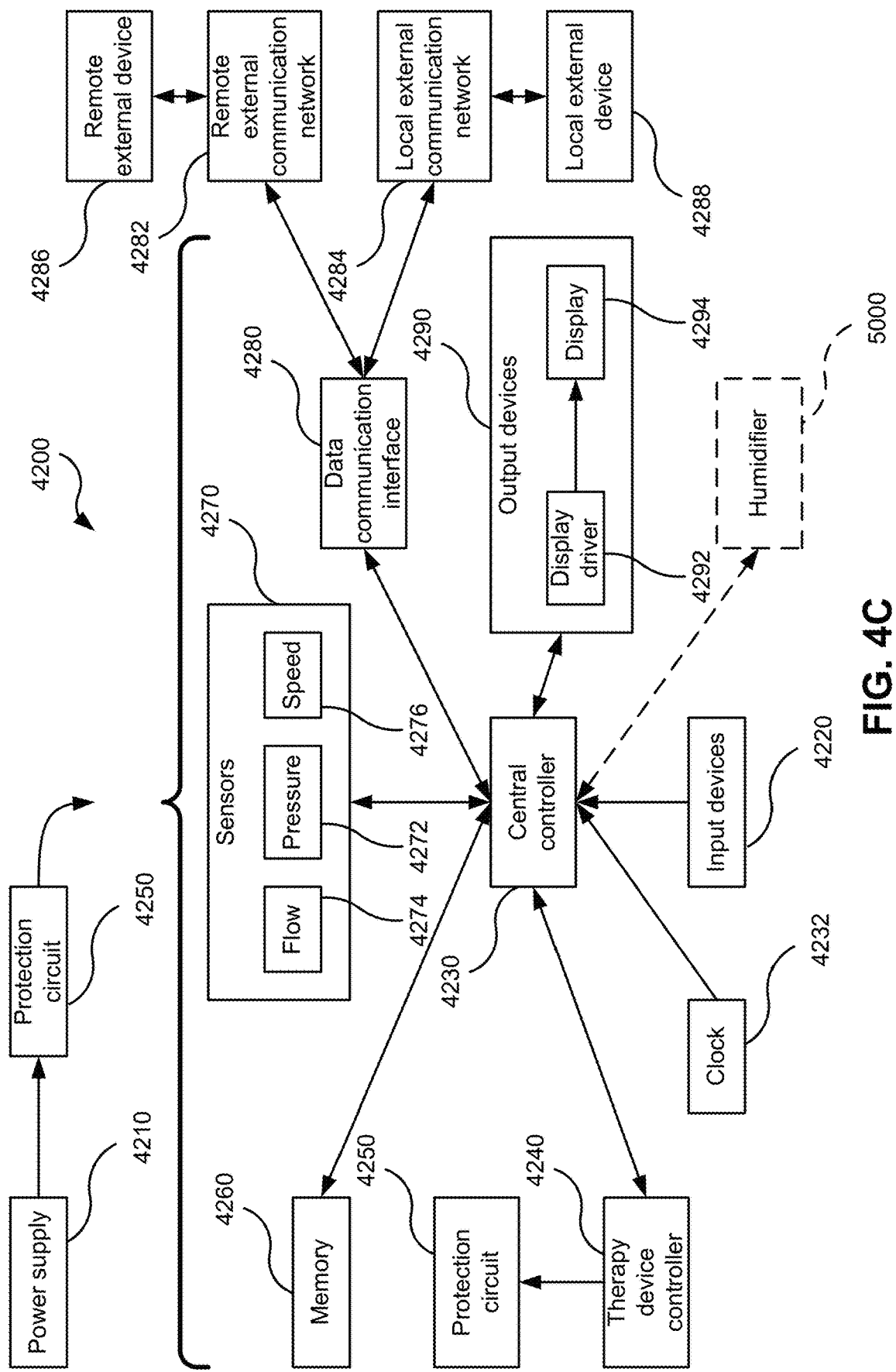

FIG. 4C is a schematic diagram of the electrical components of an RPT device in accordance with one form of the present technology.

Figure 4D:
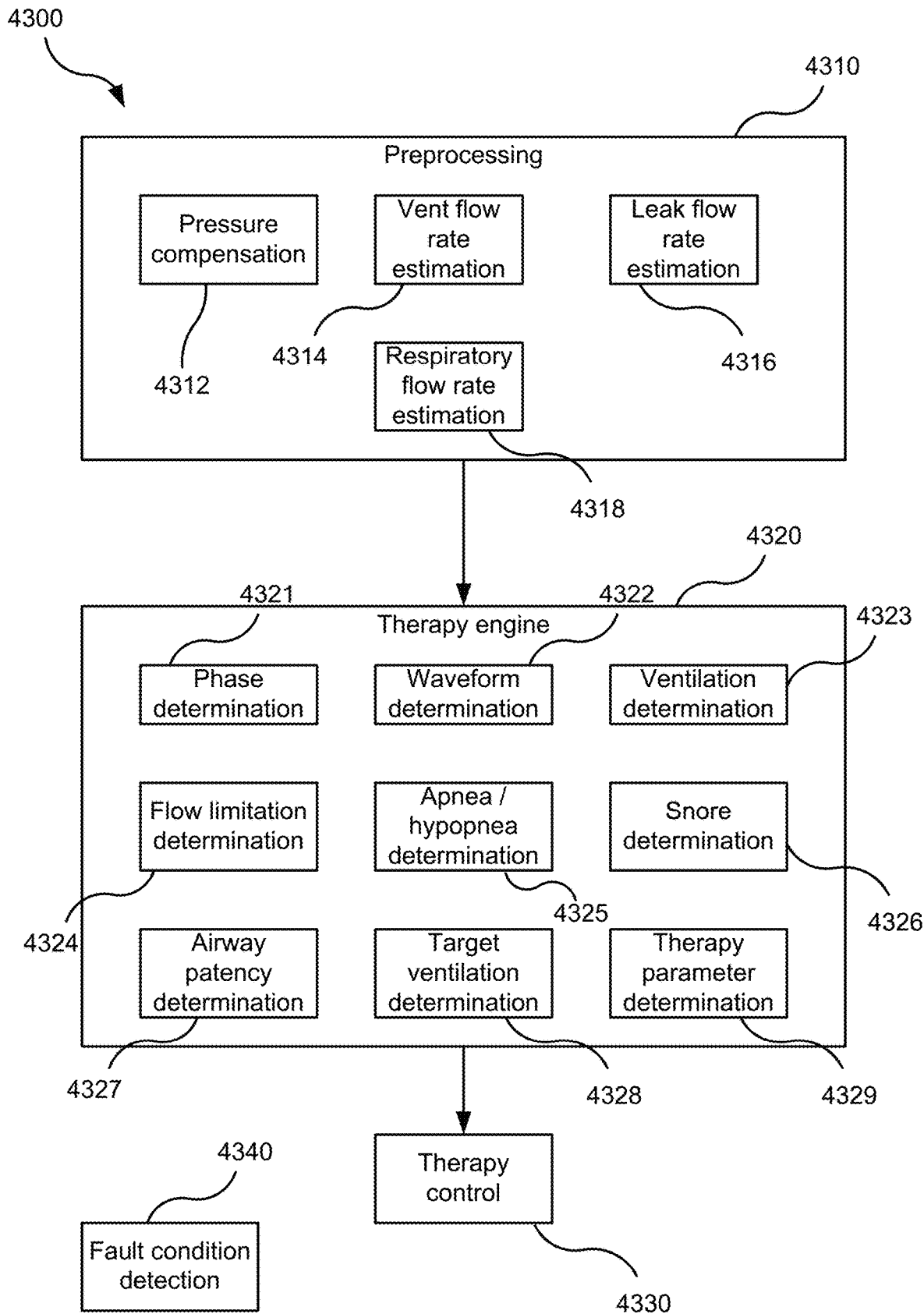

FIG. 4D is a schematic diagram of the algorithms implemented in an RPT device in accordance with one form of the present technology.

4.5 Humidifier

Figure 5A:
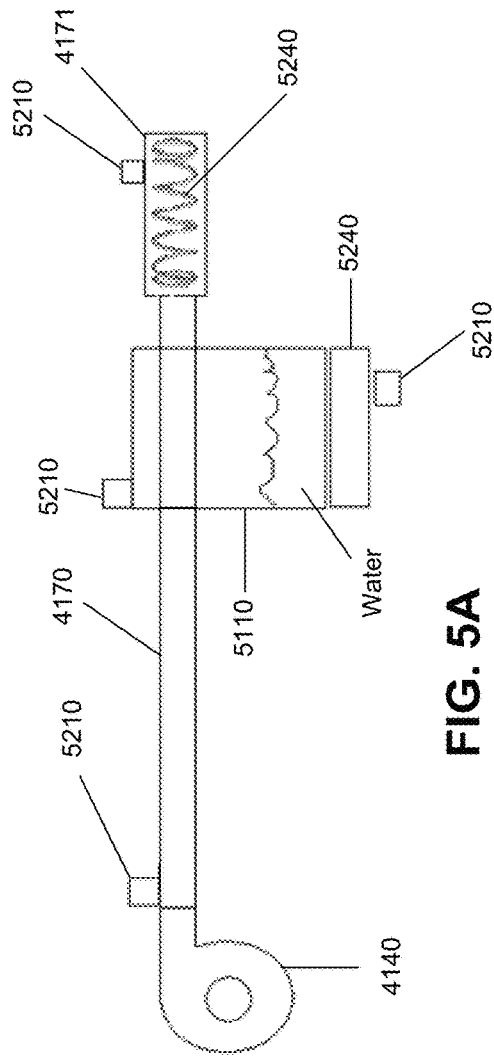

FIG. 5A shows a simplified representation of a humidifier connected to a pressure generator 4140 via an air circuit 4170 in accordance with one form of the present technology.

Figure 5B:
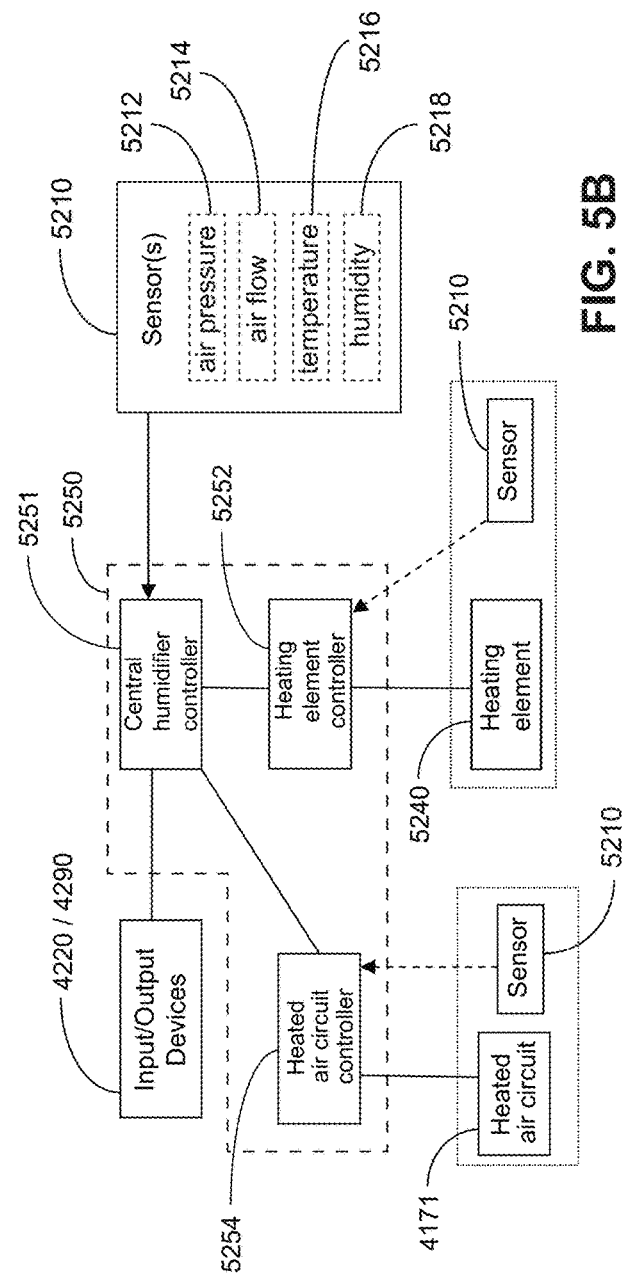

FIG. 5B shows a schematic of a humidifier in accordance with one form of the present technology.

4.6 Breathing Waveforms

Figure 6A:
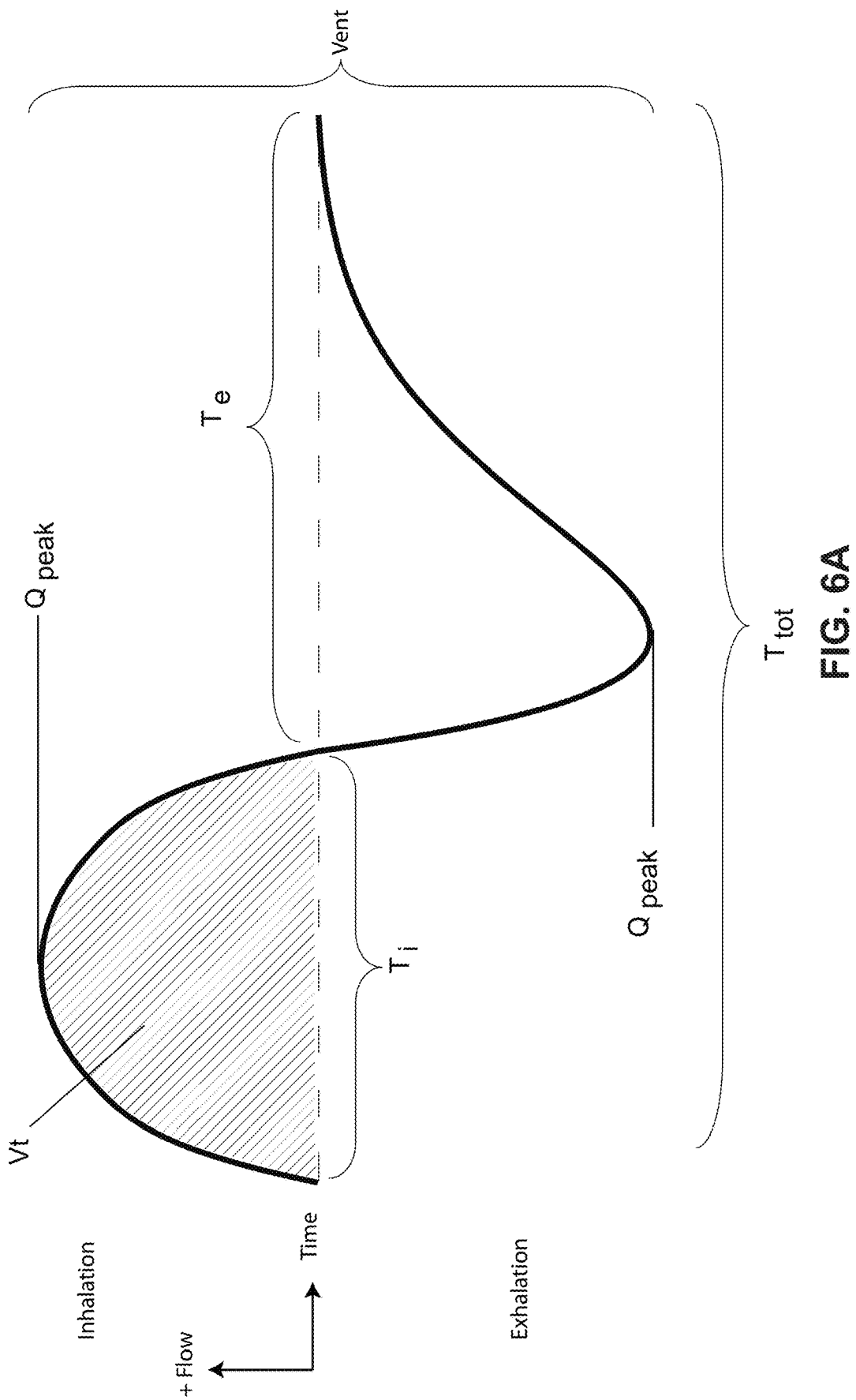

FIG. 6A shows a model typical breath waveform of a person while sleeping. The horizontal axis is time, and the vertical axis is respiratory flow rate. While the parameter values may vary, a typical breath may have the following approximate values: tidal volume, Vt, 0.5 L, inhalation time, Ti, 1.6 s, peak inspiratory flow rate, Qpeak, 0.4 L/s, exhalation time, Te, 2.4 s, peak expiratory flow rate, Qpeak, −0.5 L/s. The total duration of the breath, Ttot, is about 4 s. The person typically breathes at a rate of about 15 breaths per minute (BPM), with Ventilation, Vent, about 7.5 L/min. A typical duty cycle, the ratio of Ti to Ttot, is about 40%.

4.7 RPT Device with Humidifier

Figure 7:
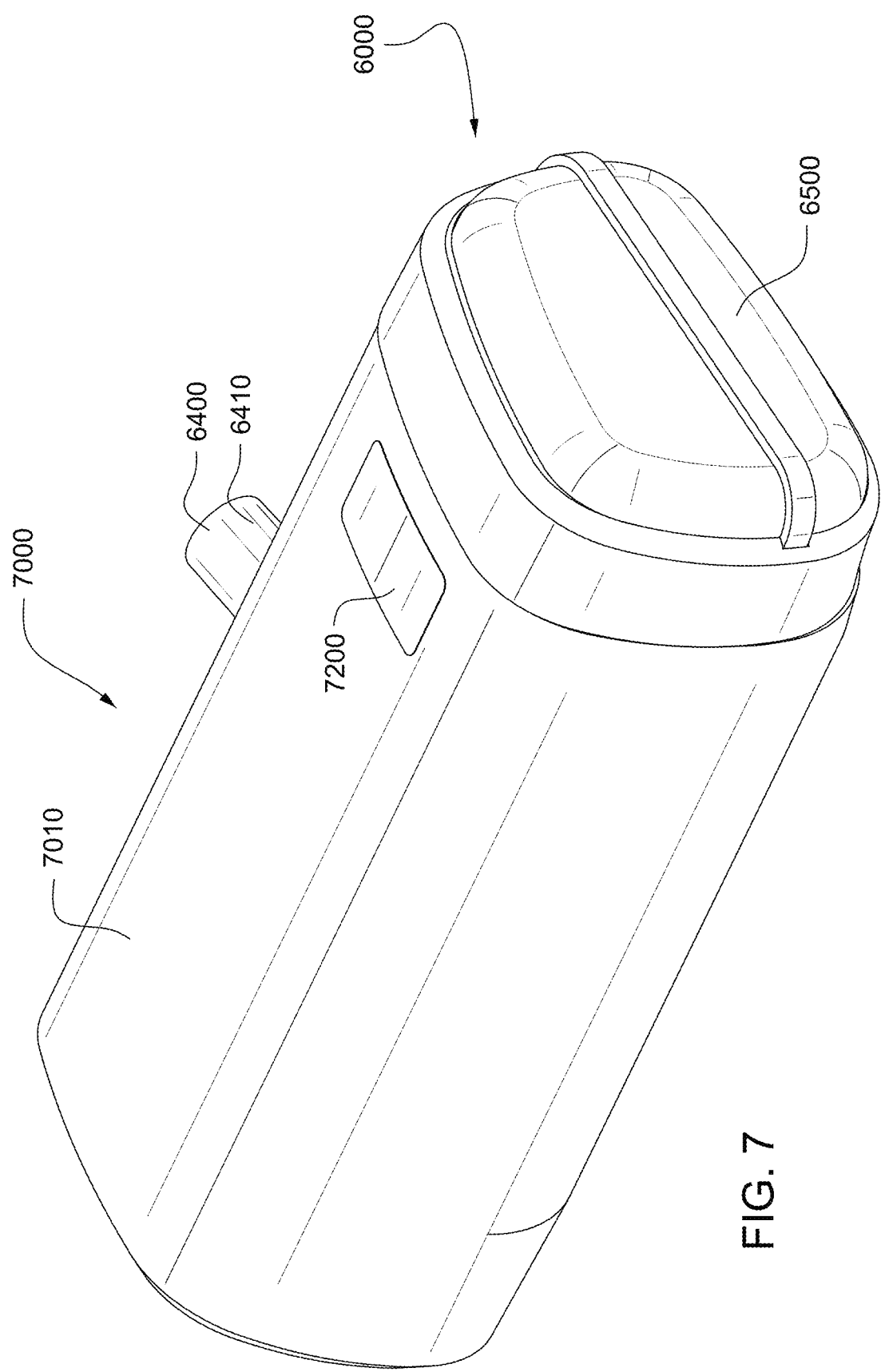

FIG. 7 is a perspective view of an RPT device and an integrated humidifier according to an example of the present technology.

Figure 8:
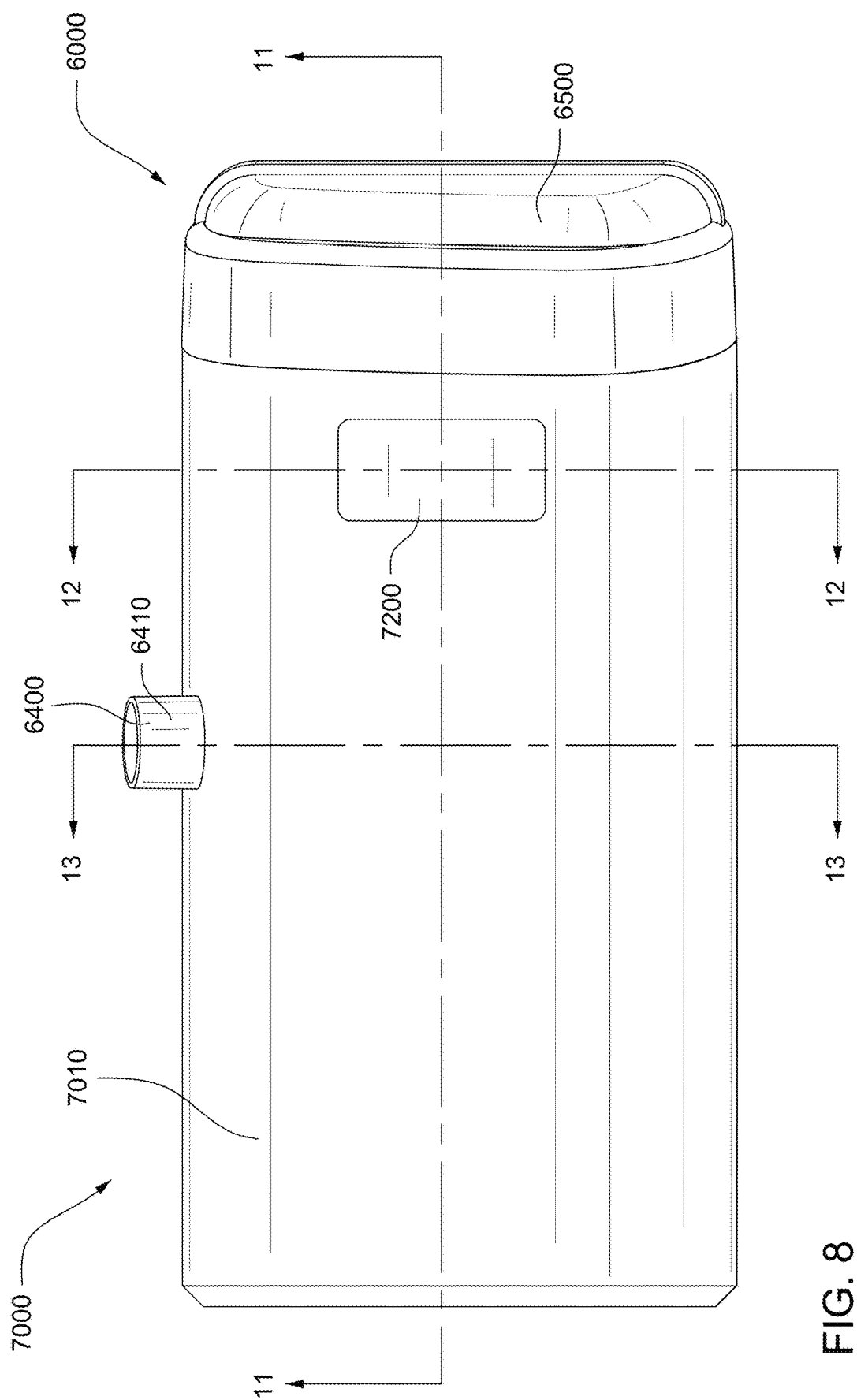

FIG. 8 is a top view of the RPT device and integrated humidifier shown in FIG. 7.

Figure 9:
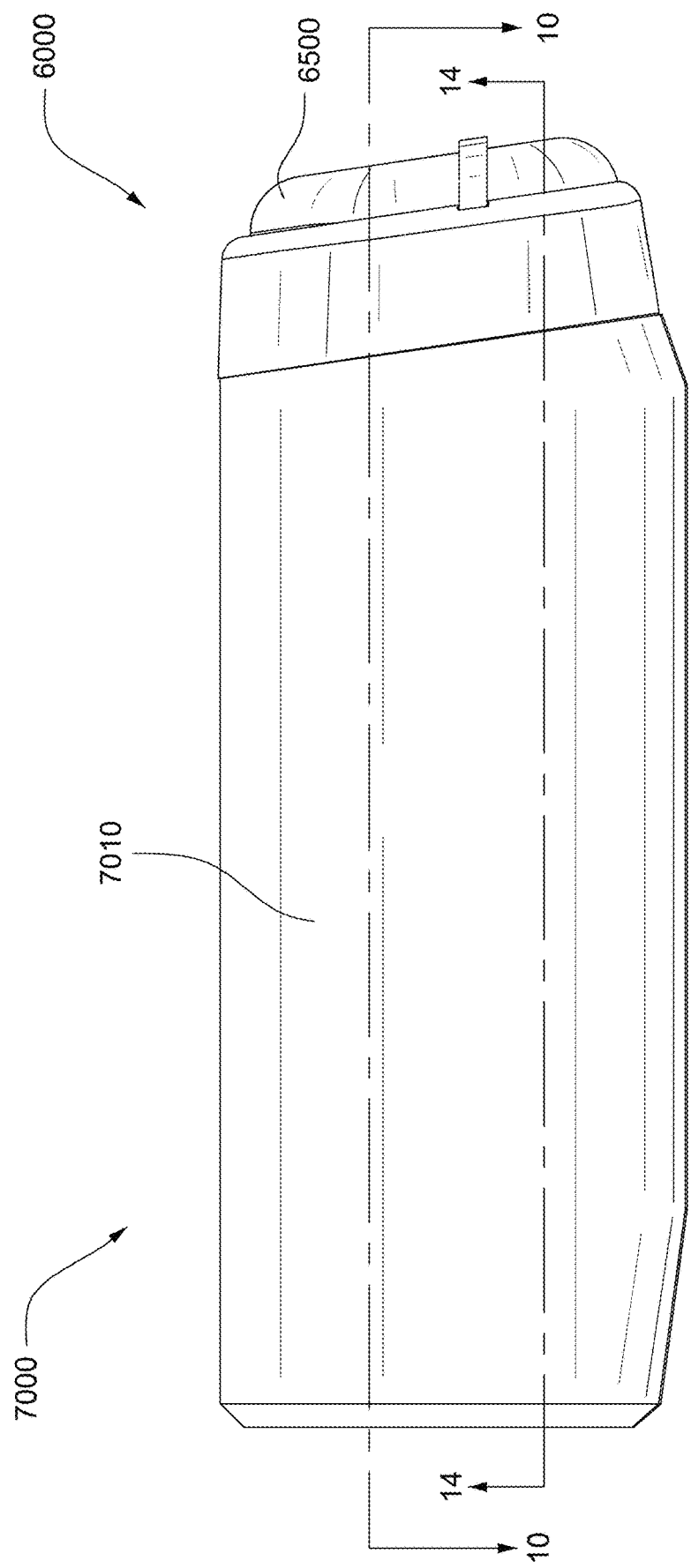

FIG. 9 is a side view of the RPT device and integrated humidifier shown in FIG. 7.

Figure 10:
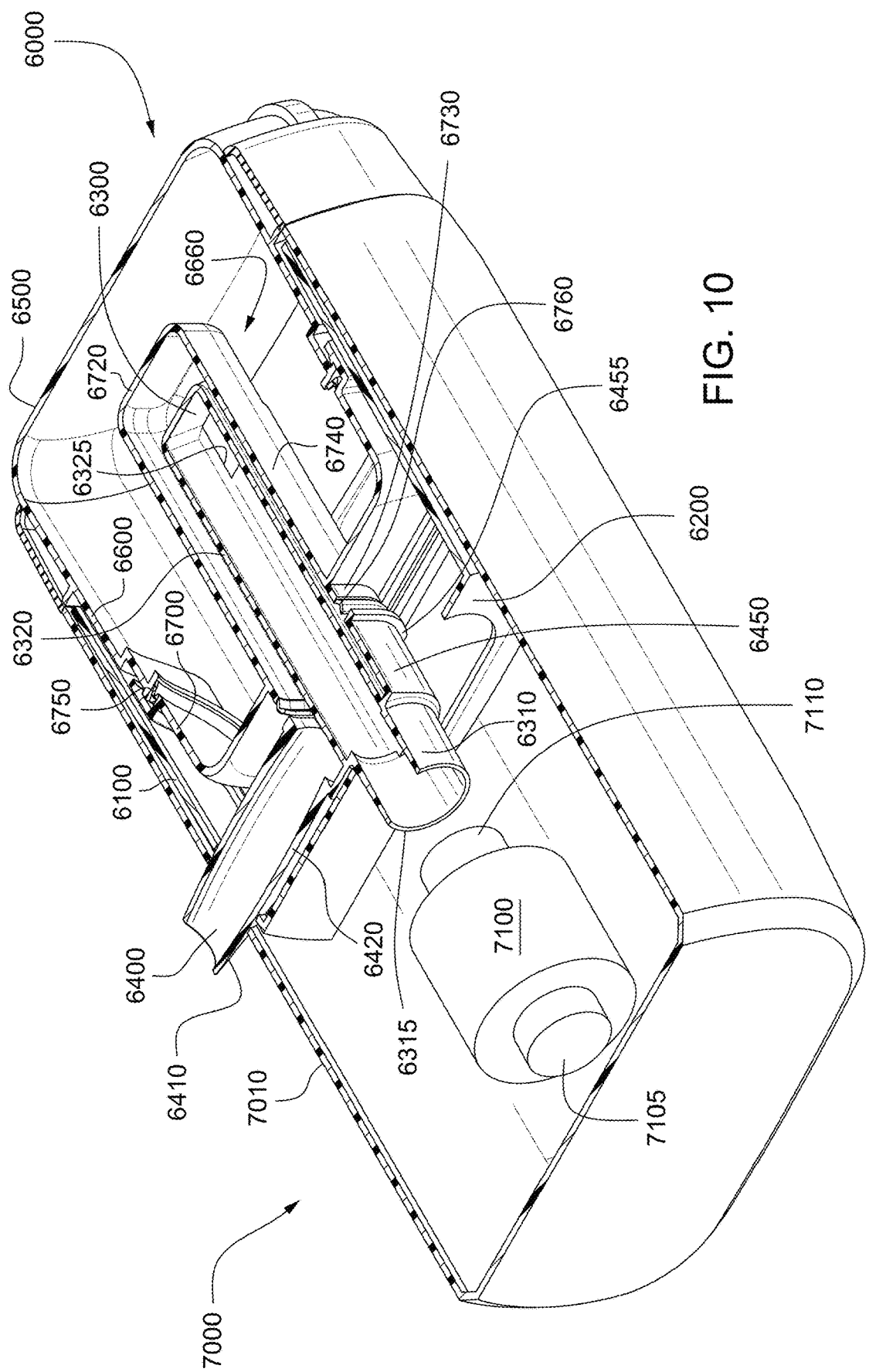

FIG. 10 is a cross-section of the RPT device and integrated humidifier as indicated on FIG. 9.

Figure 11:
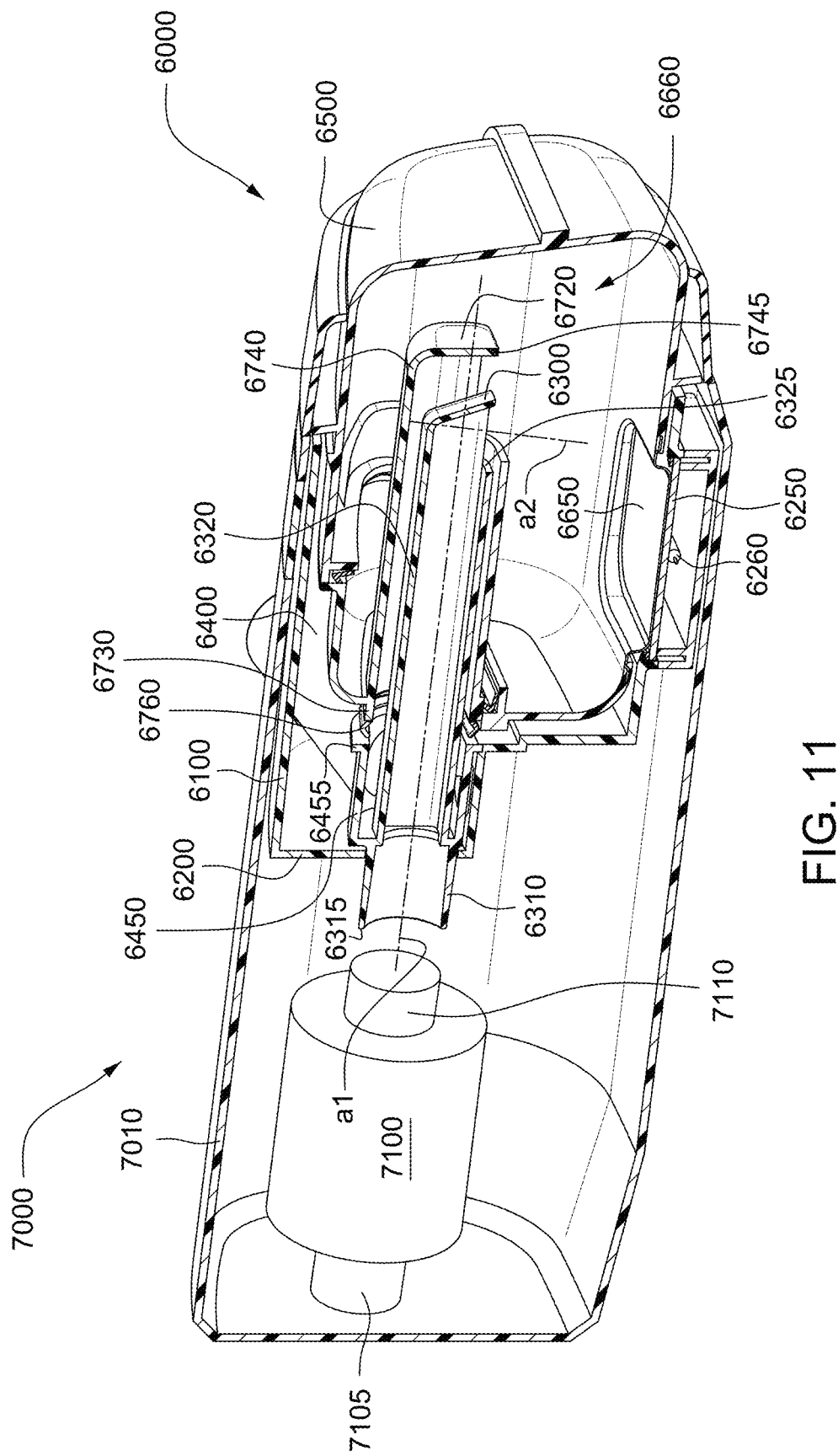

FIG. 11 is a cross-section of the RPT device and integrated humidifier as indicated on FIG. 8.

Figure 12:
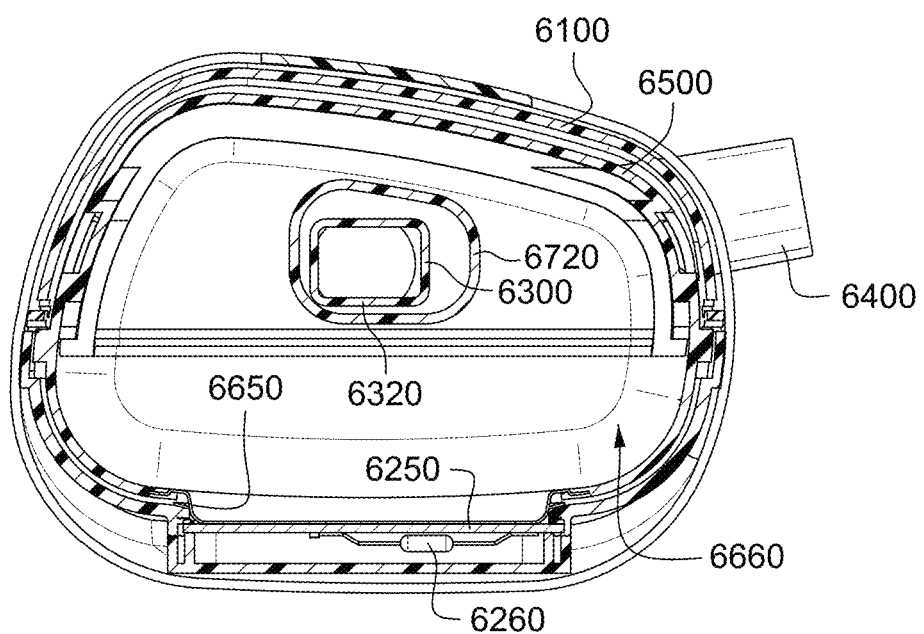

FIG. 12 is a cross-section of the RPT device and integrated humidifier as indicated on FIG. 8.

Figure 13:
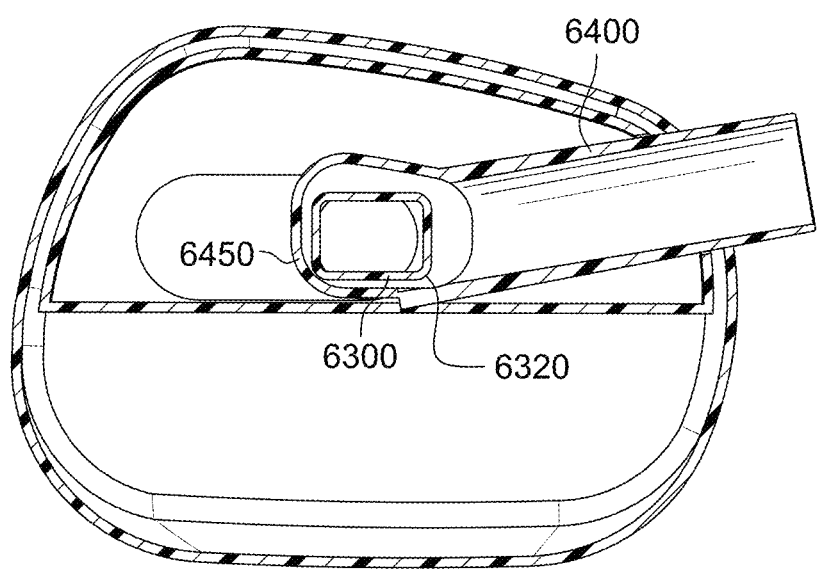

FIG. 13 is a cross-section of the RPT device and integrated humidifier as indicated on FIG. 8.

Figure 14:
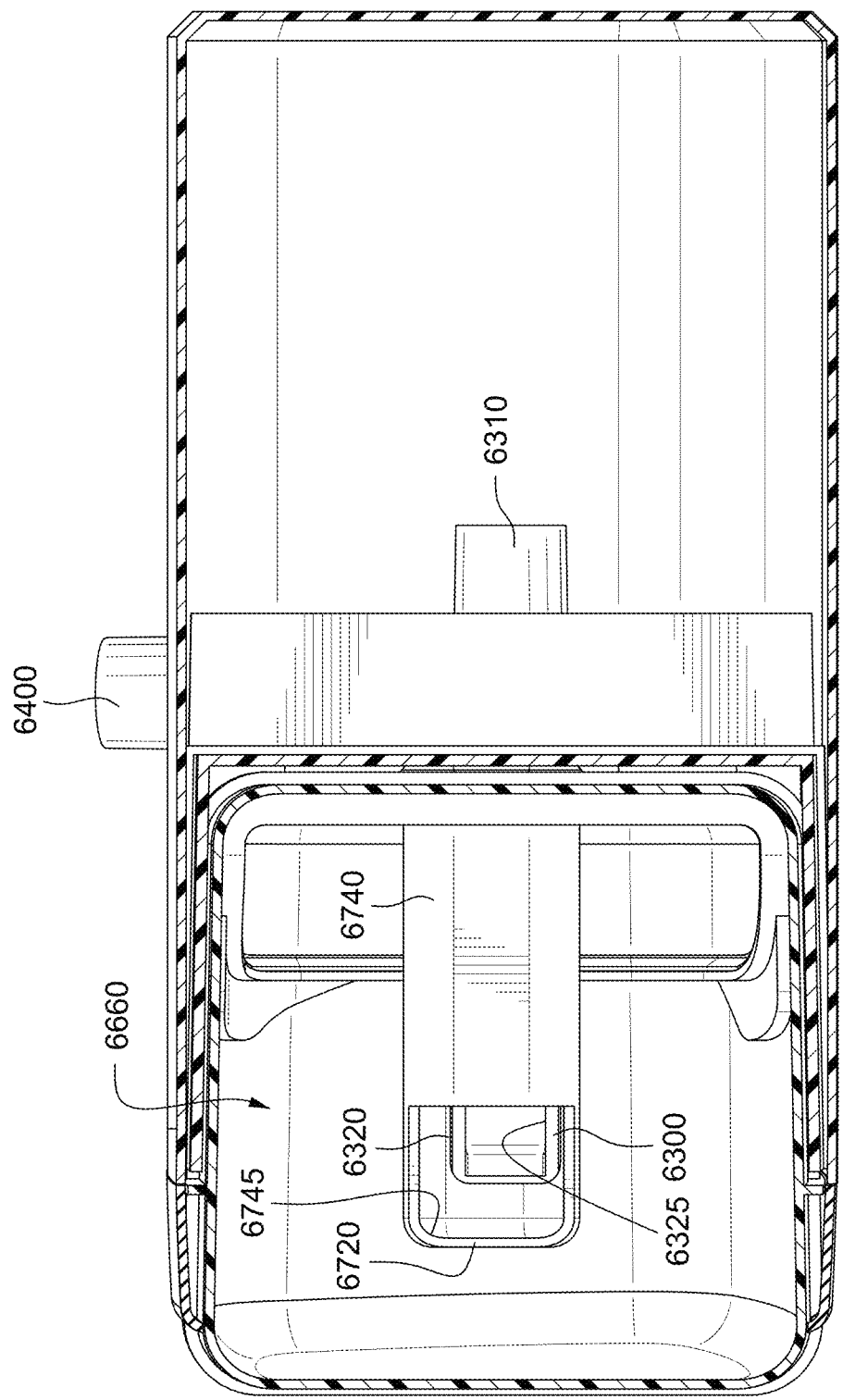

FIG. 14 is a cross-section of the RPT device and integrated humidifier as indicated on FIG. 9.

Figure 15:
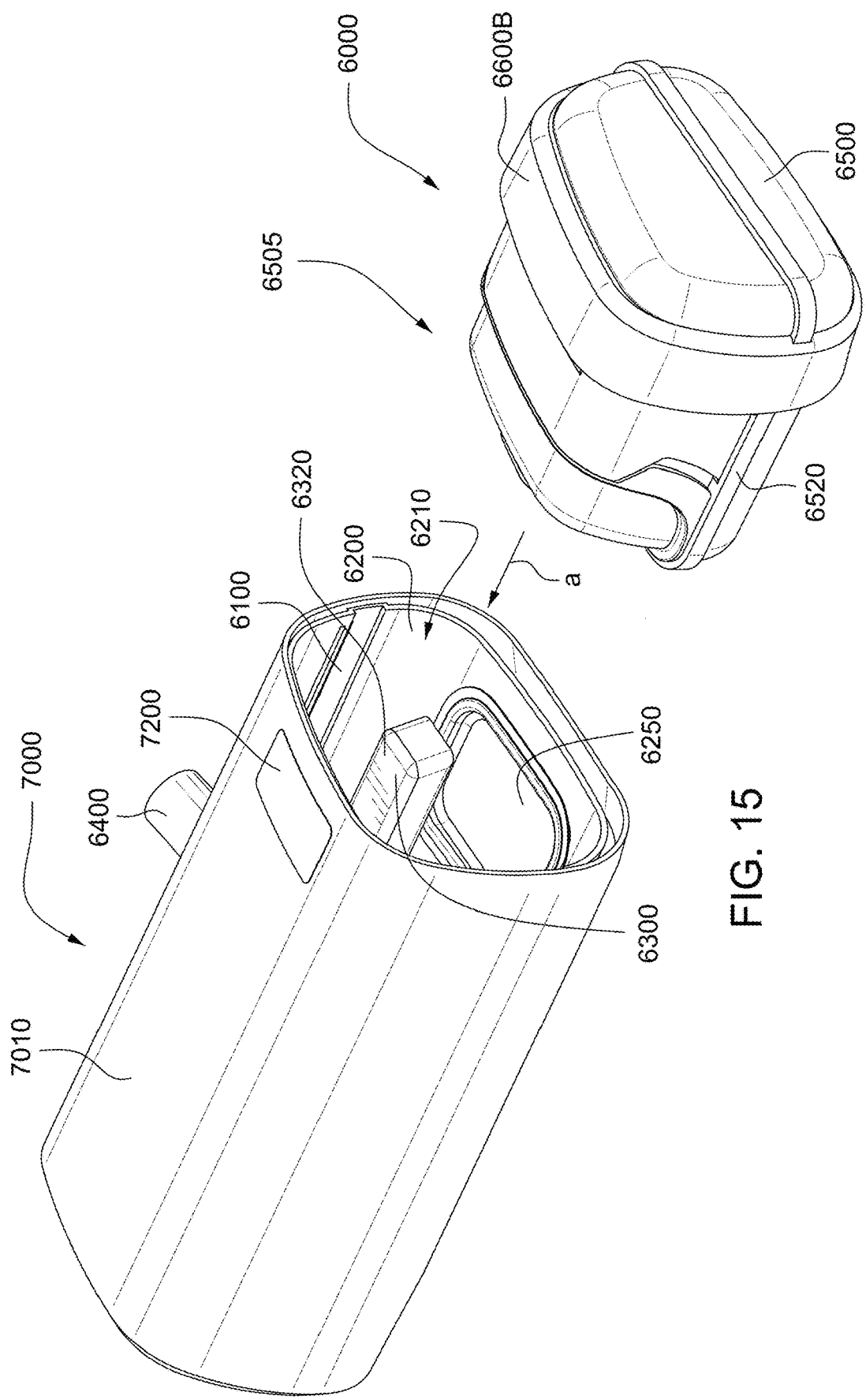

FIG. 15 is an exploded view of the RPT device and integrated humidifier shown in FIG. 7.

Figure 16:
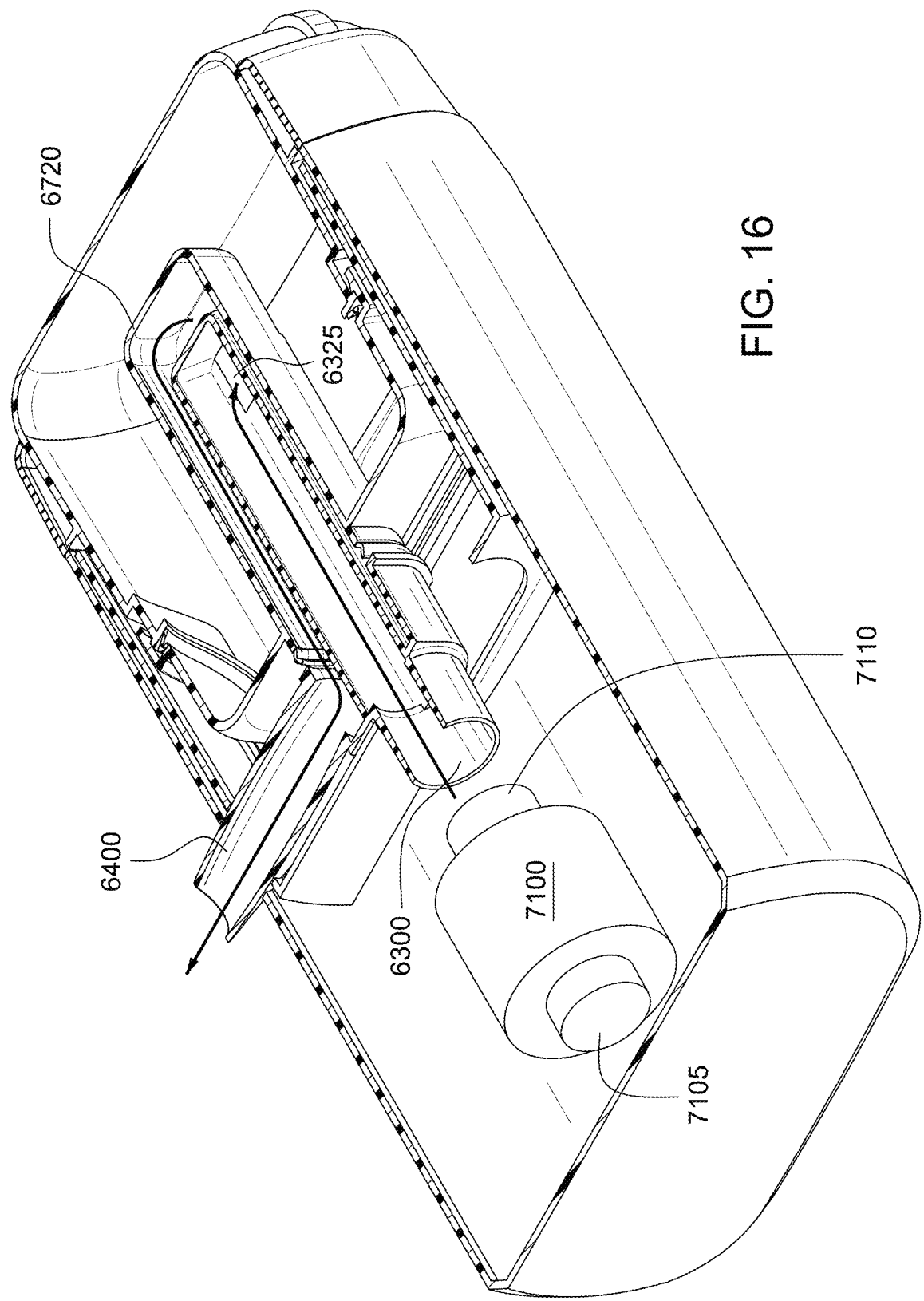

FIG. 16 is a cross-section similar to FIG. 10 showing flow paths through a humidifier according to an example of the present technology.

Figure 17:
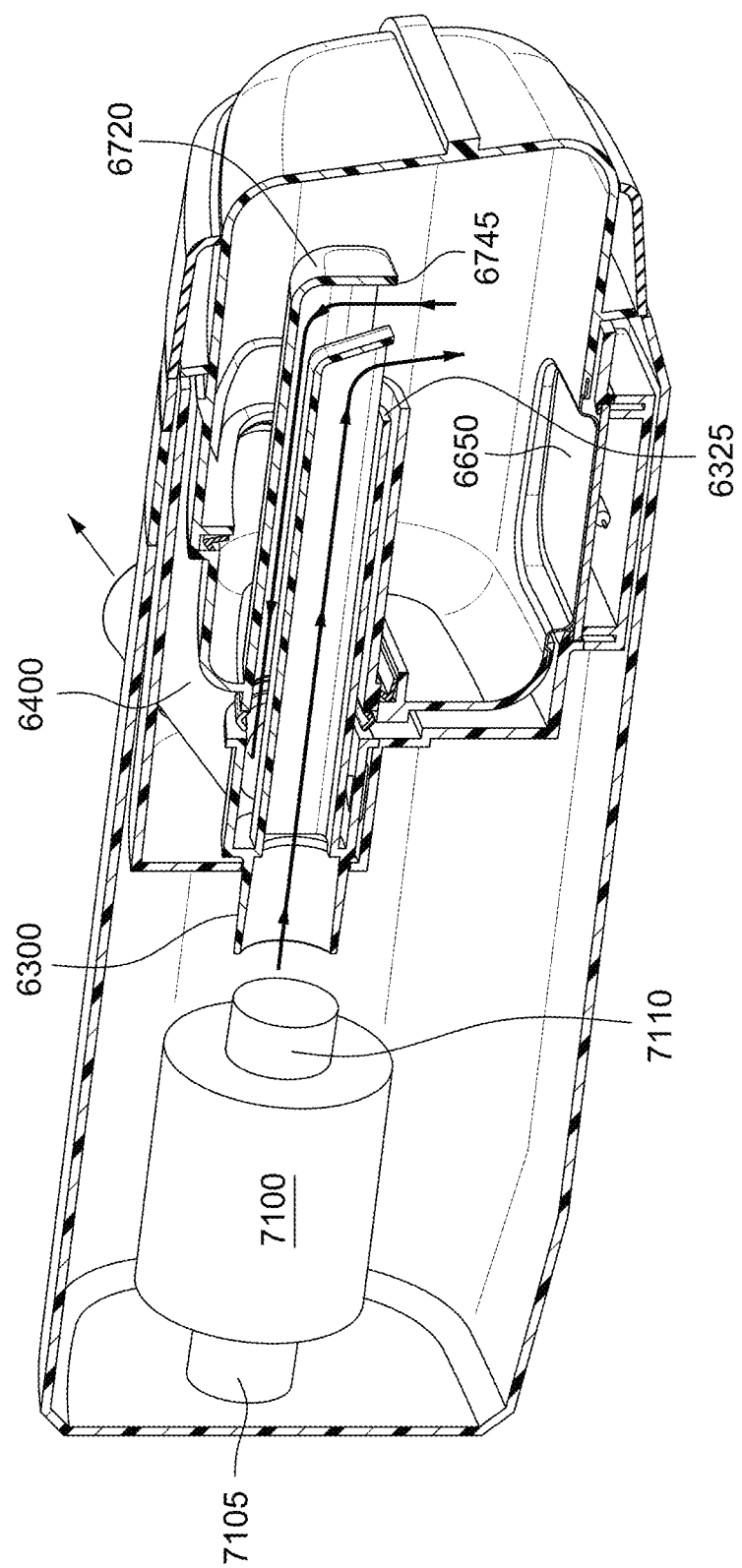

FIG. 17 is a cross-section similar to FIG. 11 showing flow paths through a humidifier according to an example of the present technology.

Figure 18:
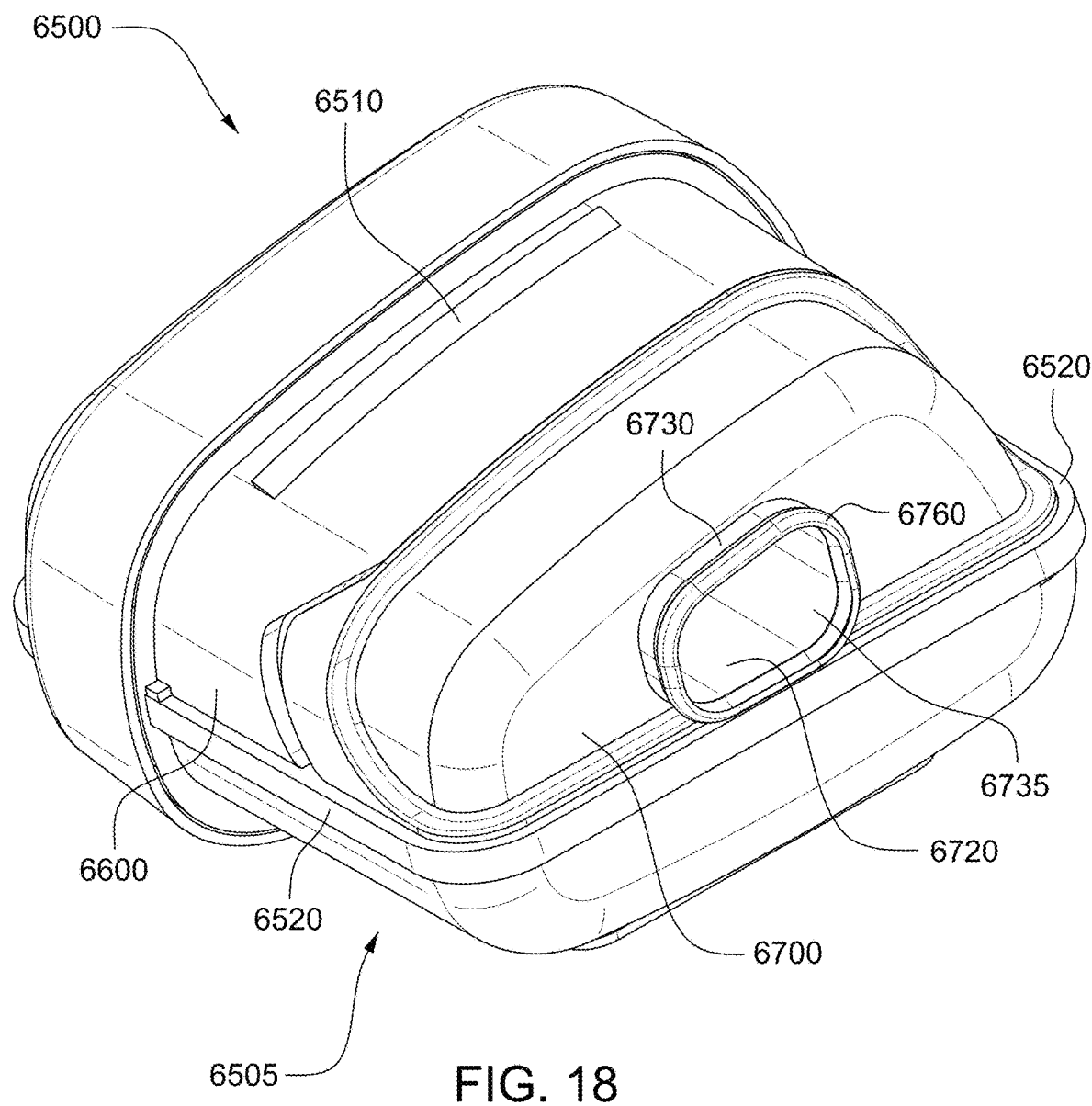

FIG. 18 is a perspective view of a water reservoir for a humidifier according to an example of the present technology.

Figure 19:
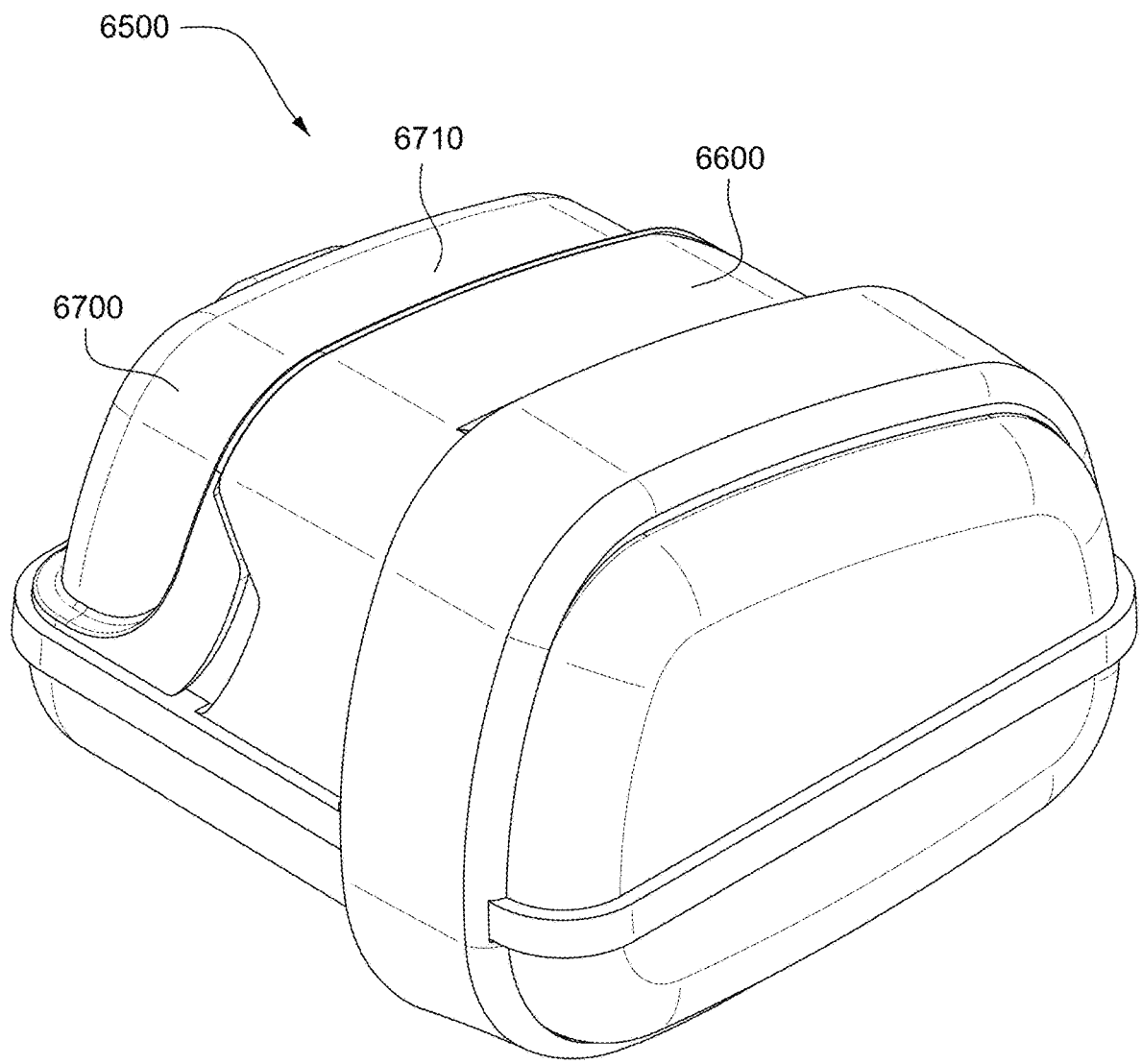

FIG. 19 is another perspective view of the water reservoir shown in FIG. 18.

Figure 20:
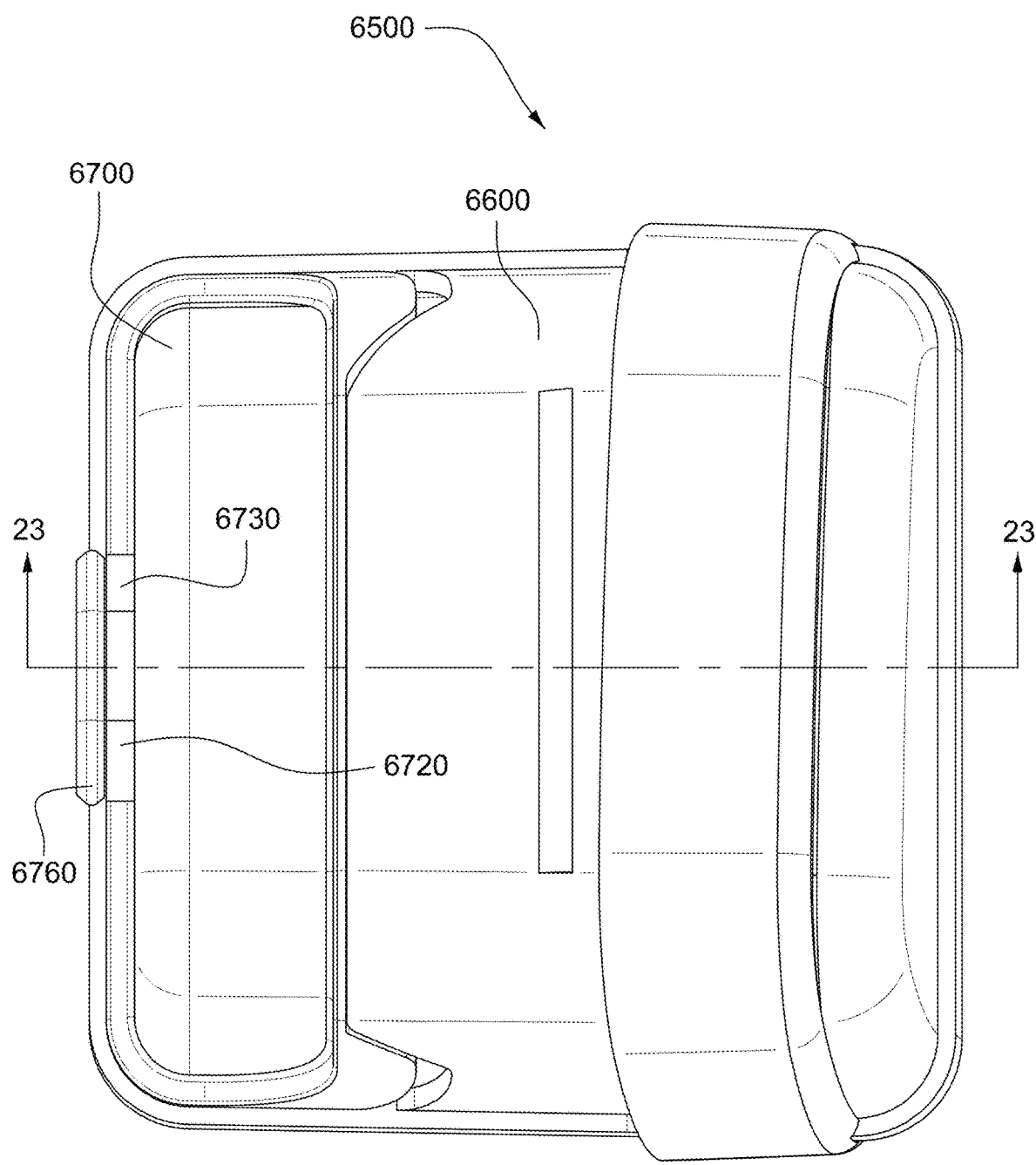

FIG. 20 is a top view of the water reservoir shown in FIG. 18.

Figure 21:
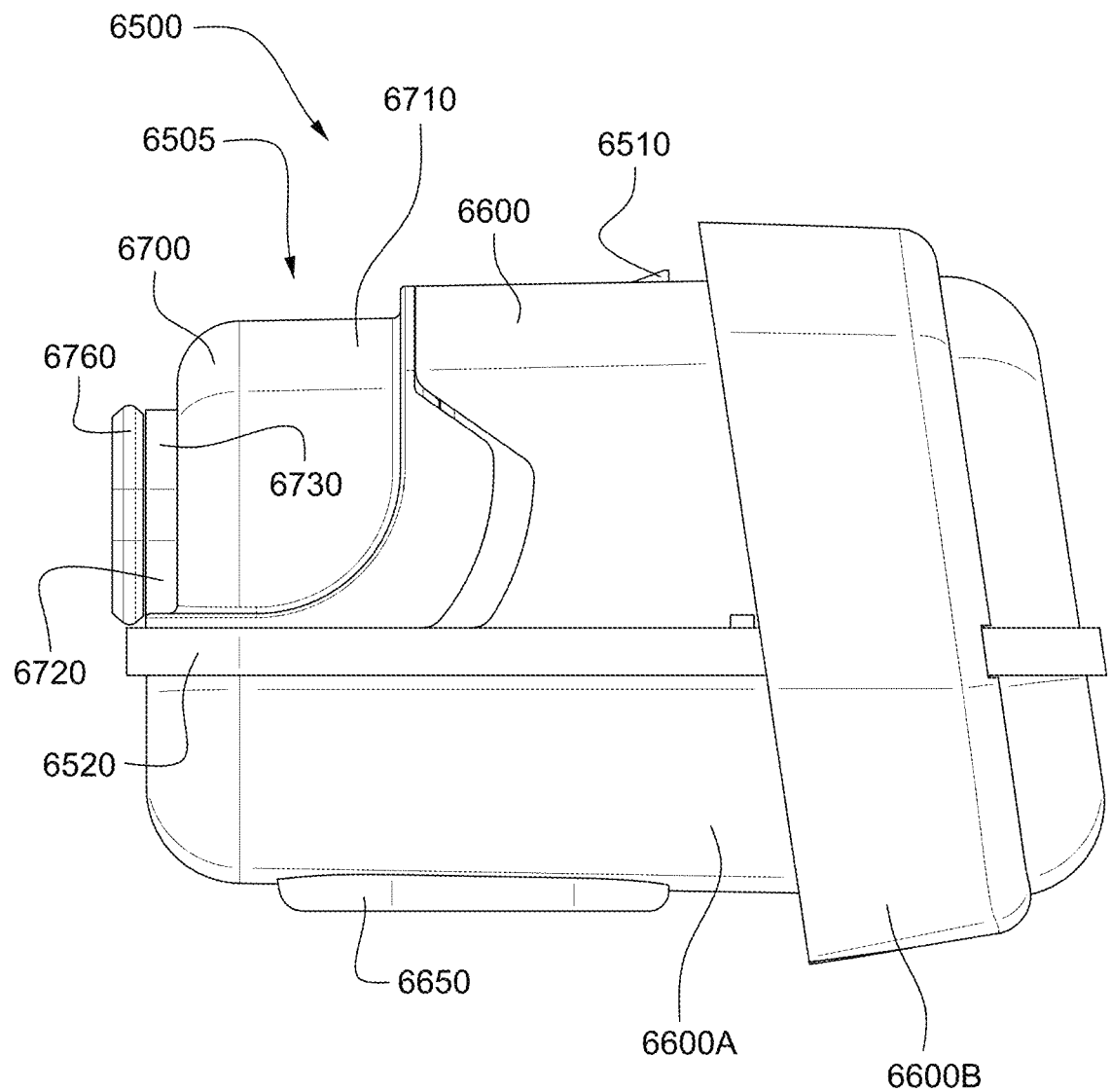

FIG. 21 is a side view of the water reservoir shown in FIG. 18.

Figure 22:
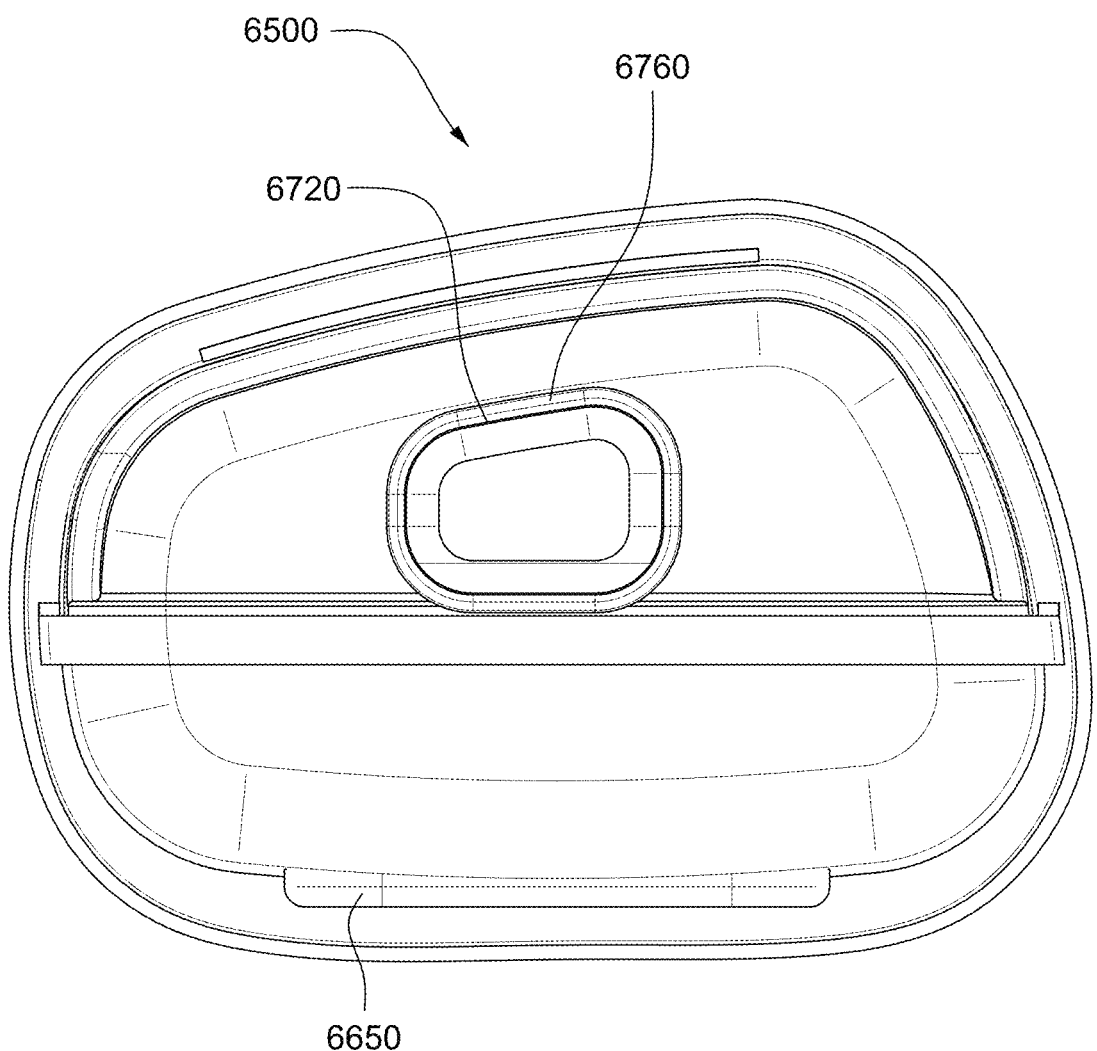

FIG. 22 is a front view of the water reservoir shown in FIG. 18.

Figure 23:
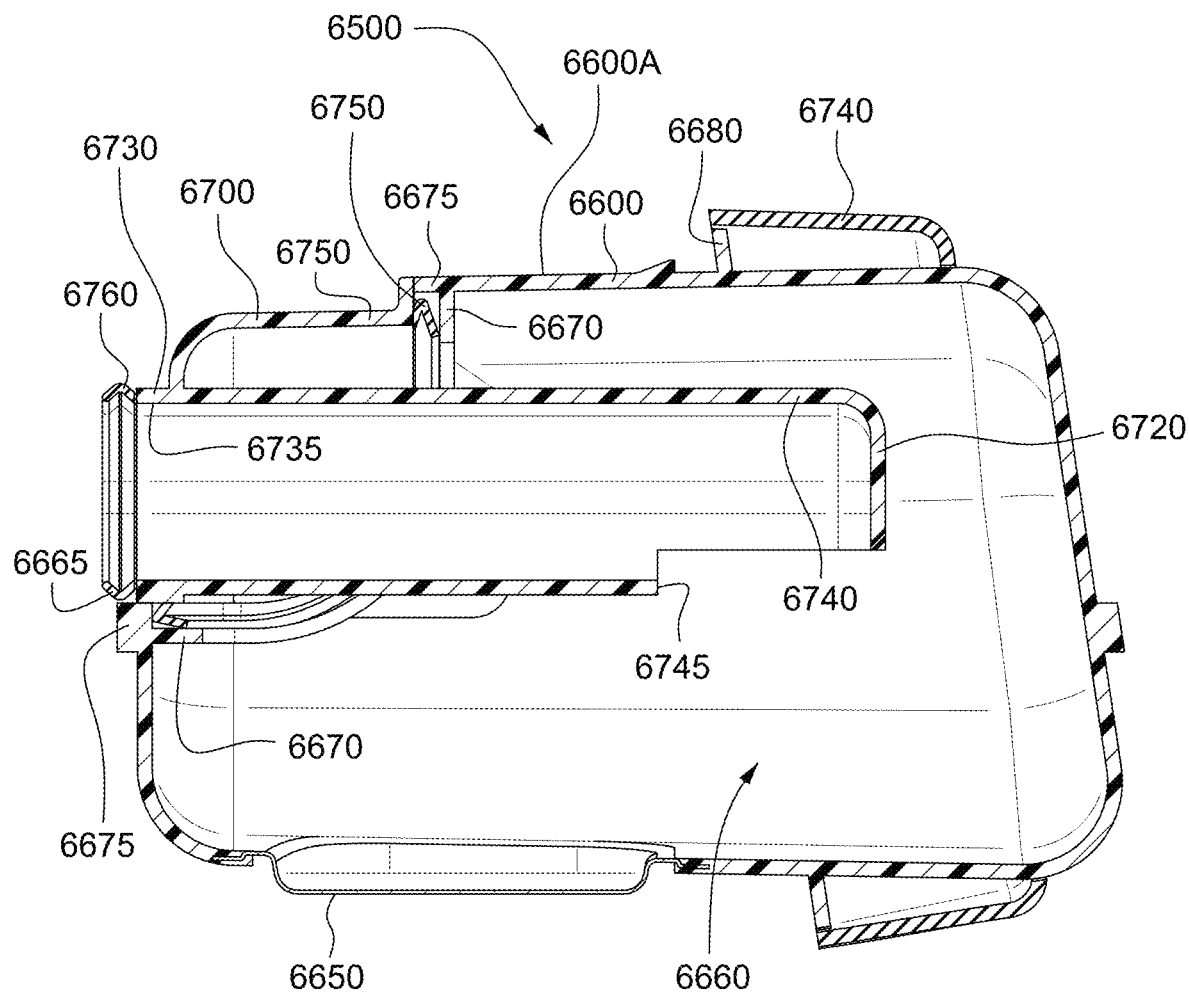

FIG. 23 is a cross-section of the water reservoir as indicated on FIG. 20.

Figure 24:
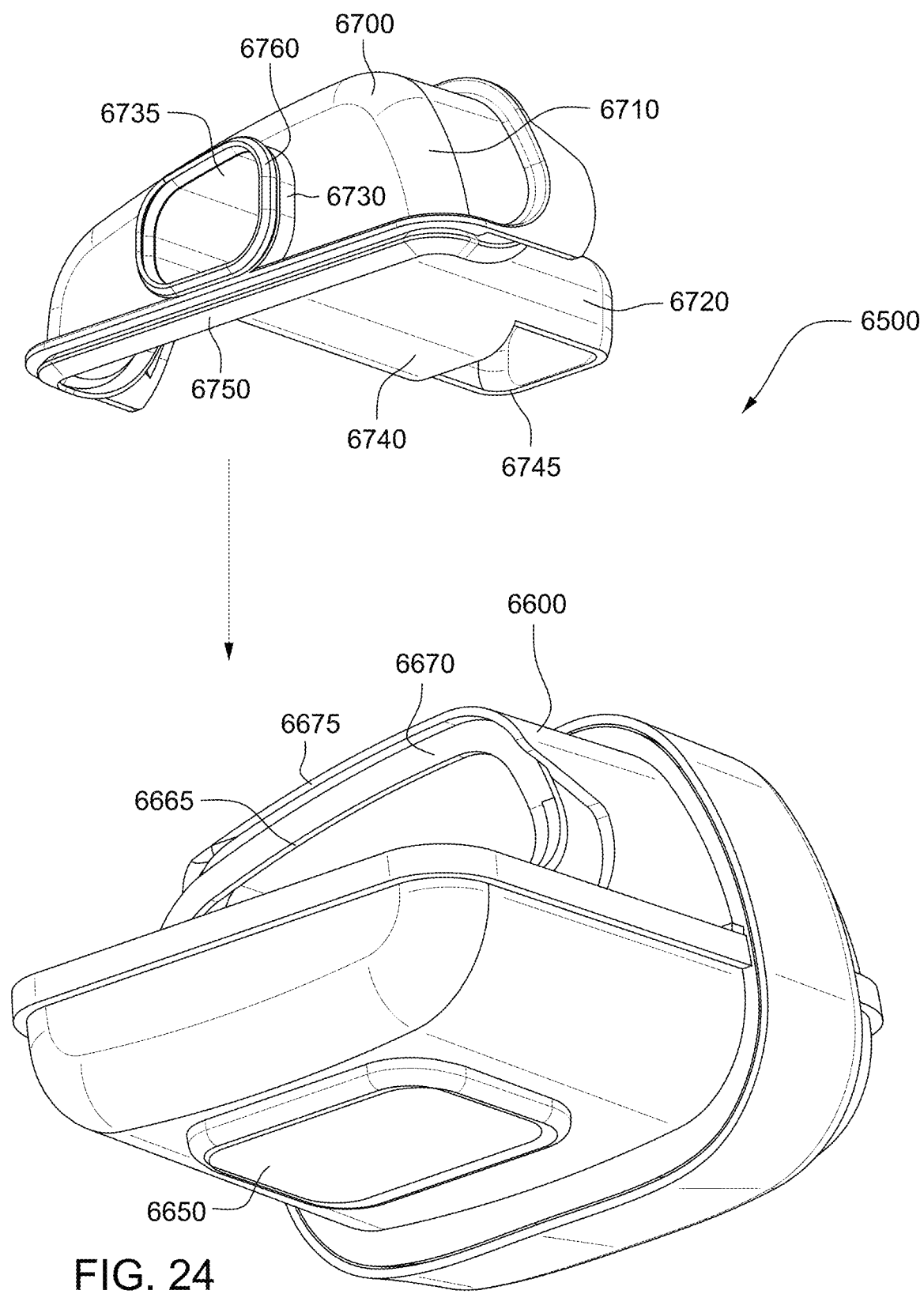

FIG. 24 is an exploded view of the water reservoir shown in FIG. 18.

Figure 25:
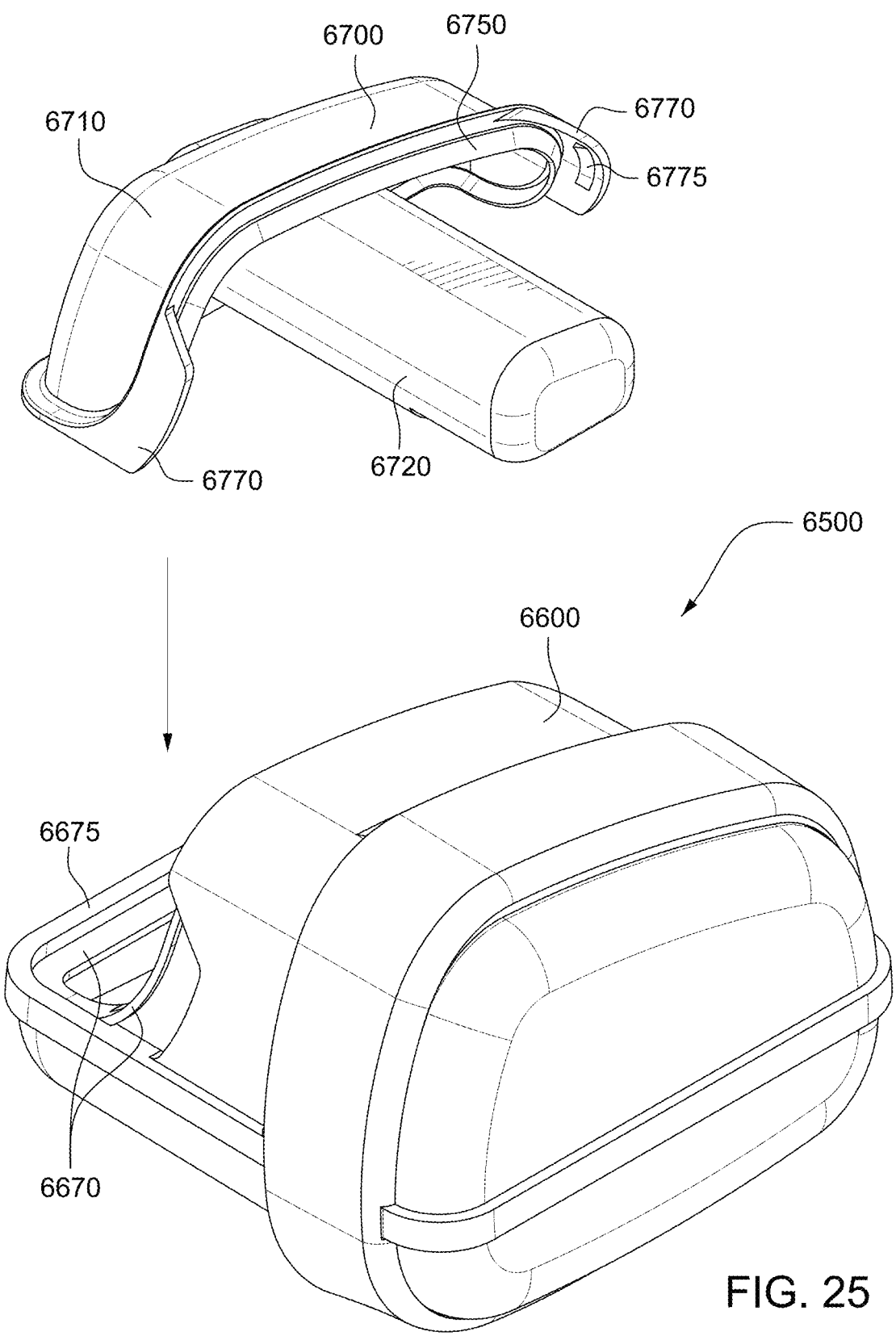

FIG. 25 is another exploded view of the water reservoir shown in FIG. 18.

Figure 26:
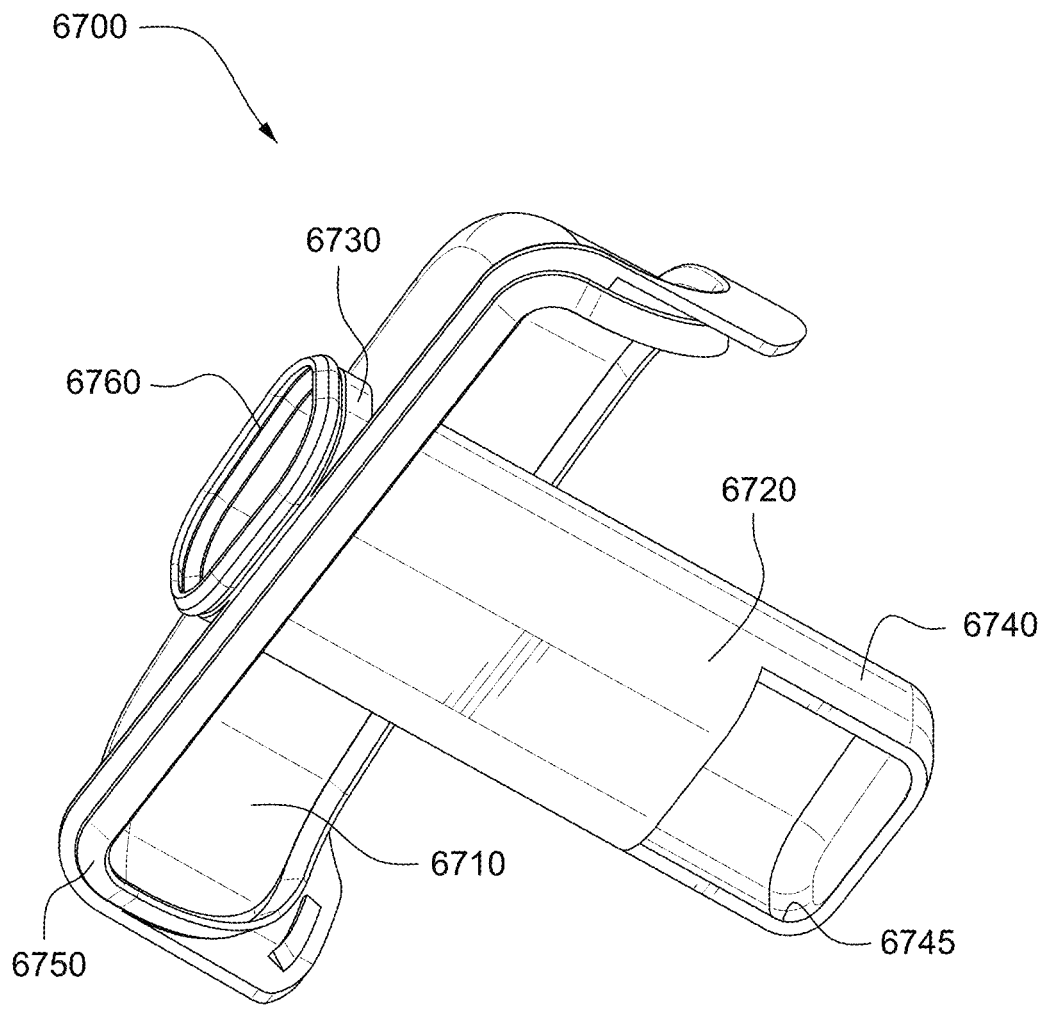

FIG. 26 is a perspective view of a reservoir lid of the water reservoir shown in FIG. 18.

Figure 27:
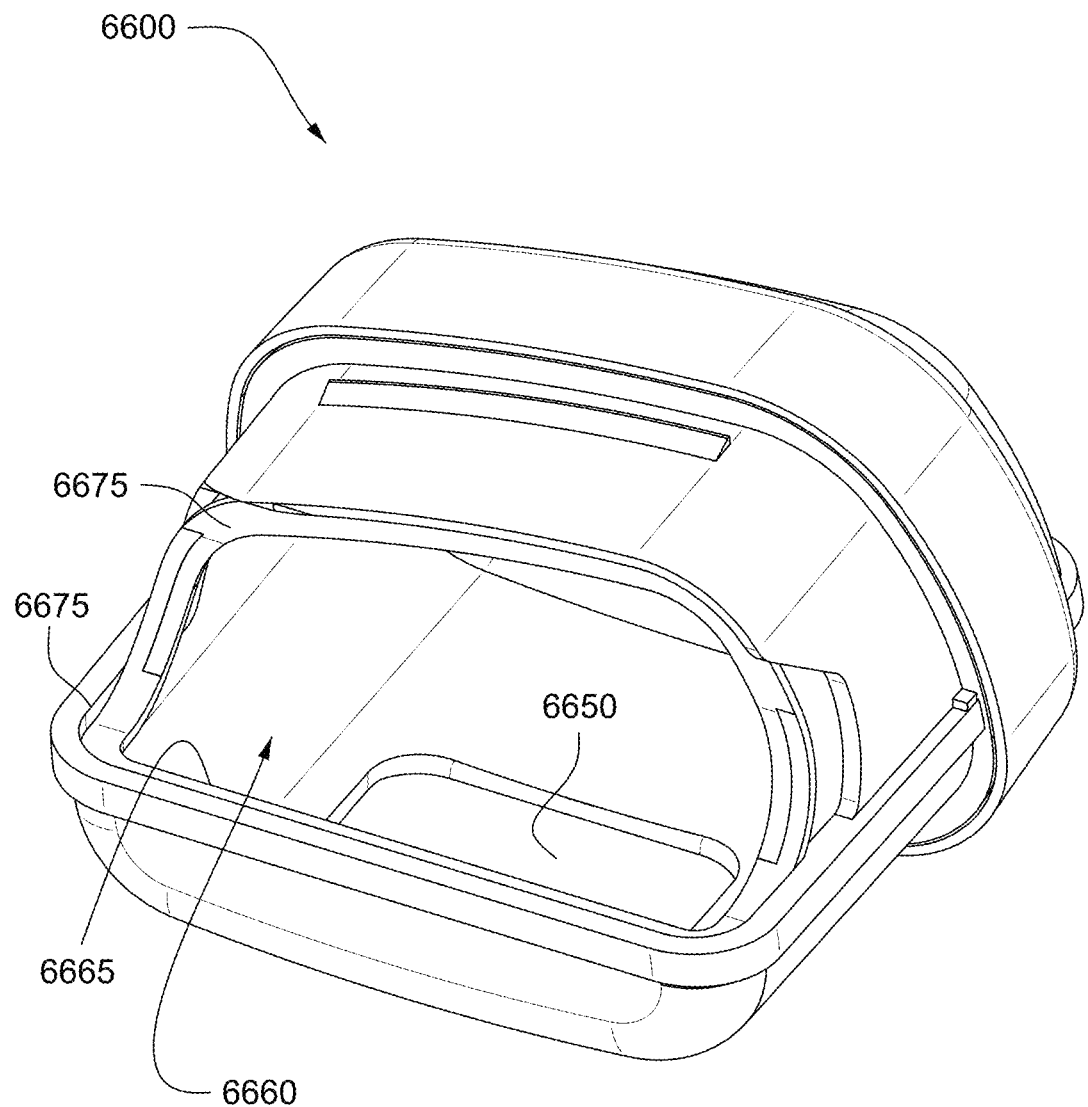

FIG. 27 is a perspective view of a reservoir base of the water reservoir shown in FIG. 18.

Figure 28:
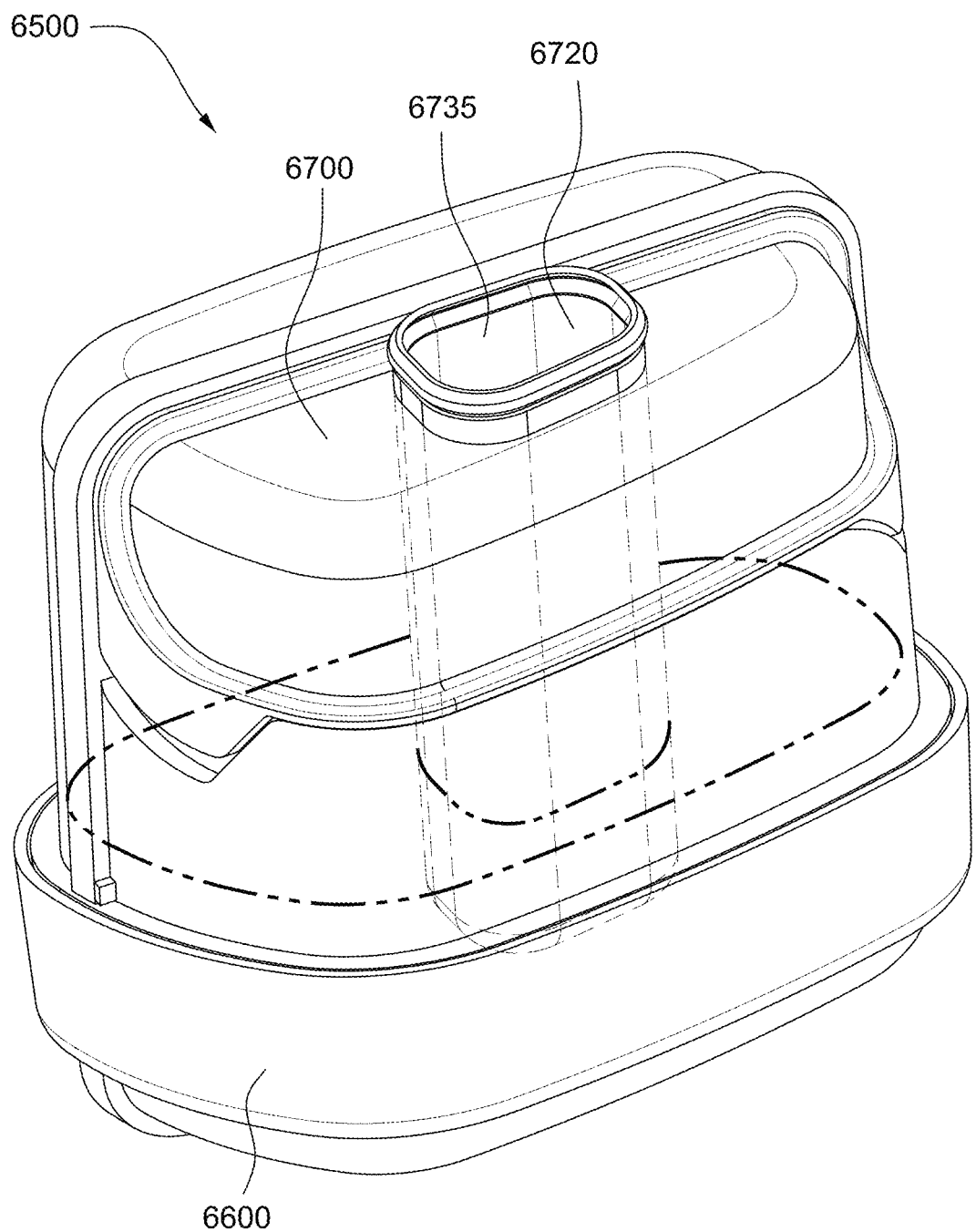

FIG. 28 is a perspective view showing an overfill prevention feature of the water reservoir shown in FIG. 18.

Figure 29:
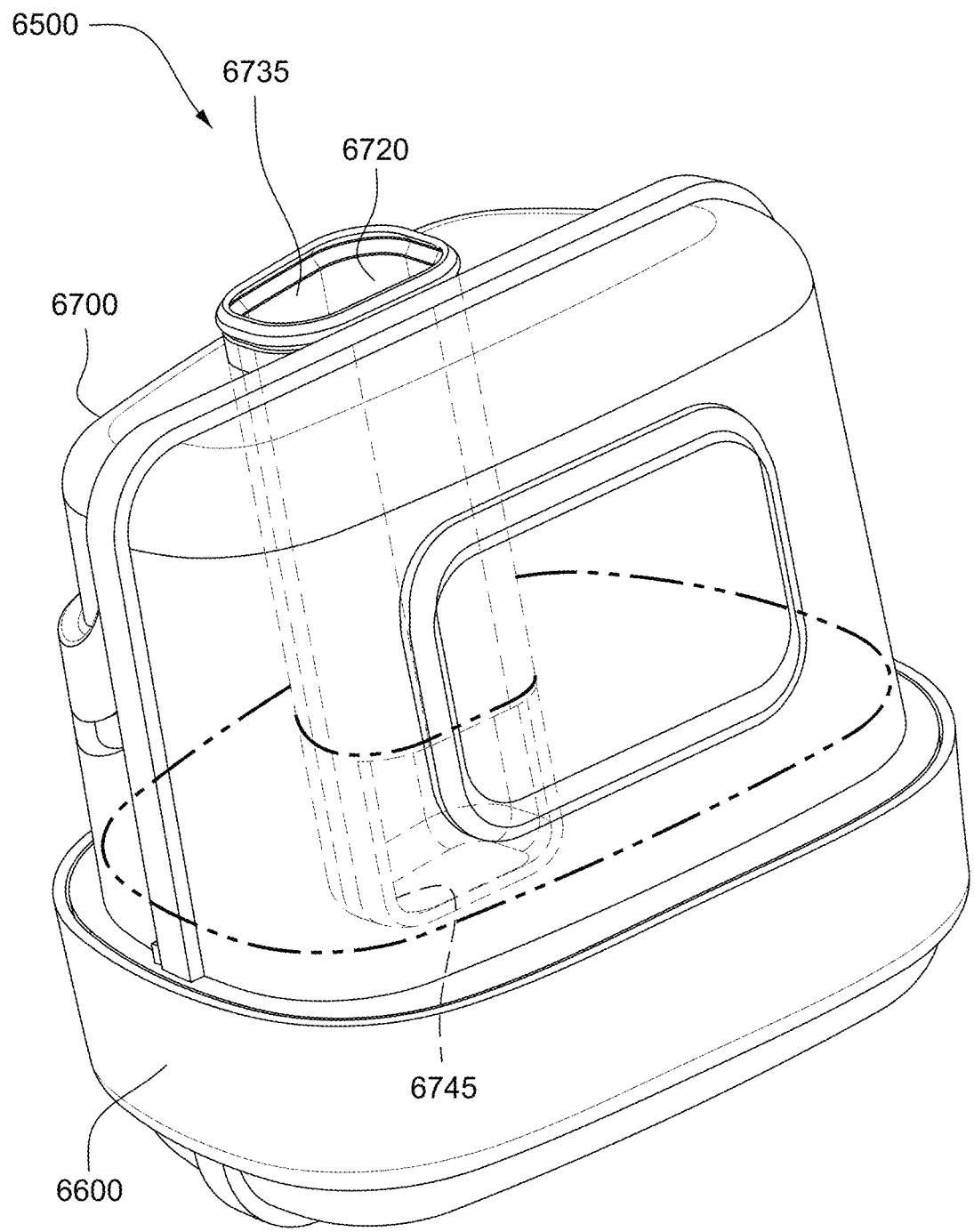

FIG. 29 is another perspective view showing an overfill prevention feature of the water reservoir shown in FIG. 18.

Figure 30:
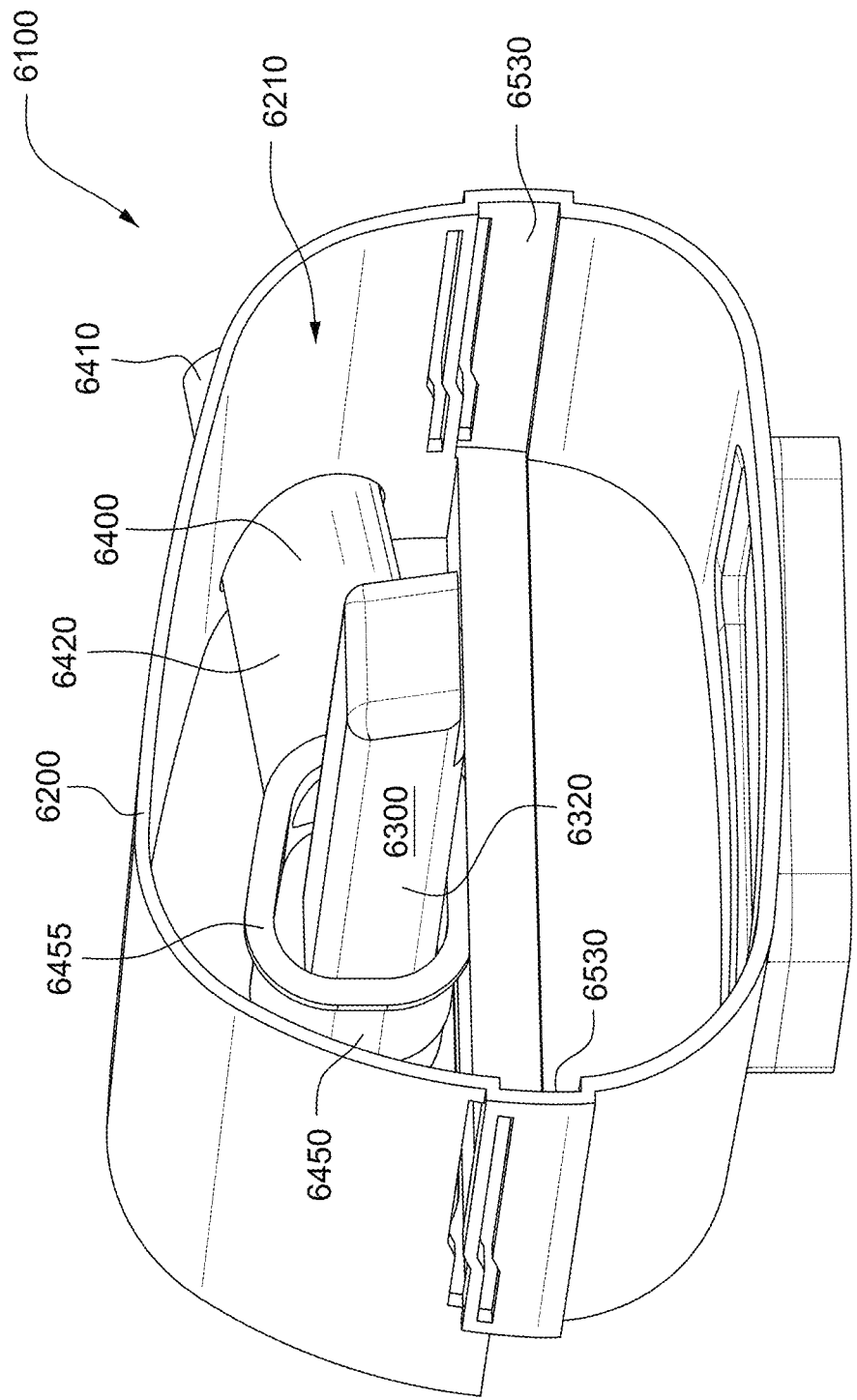

FIG. 30 is a perspective view of a reservoir dock for a humidifier according to an example of the present technology.

Figure 31:
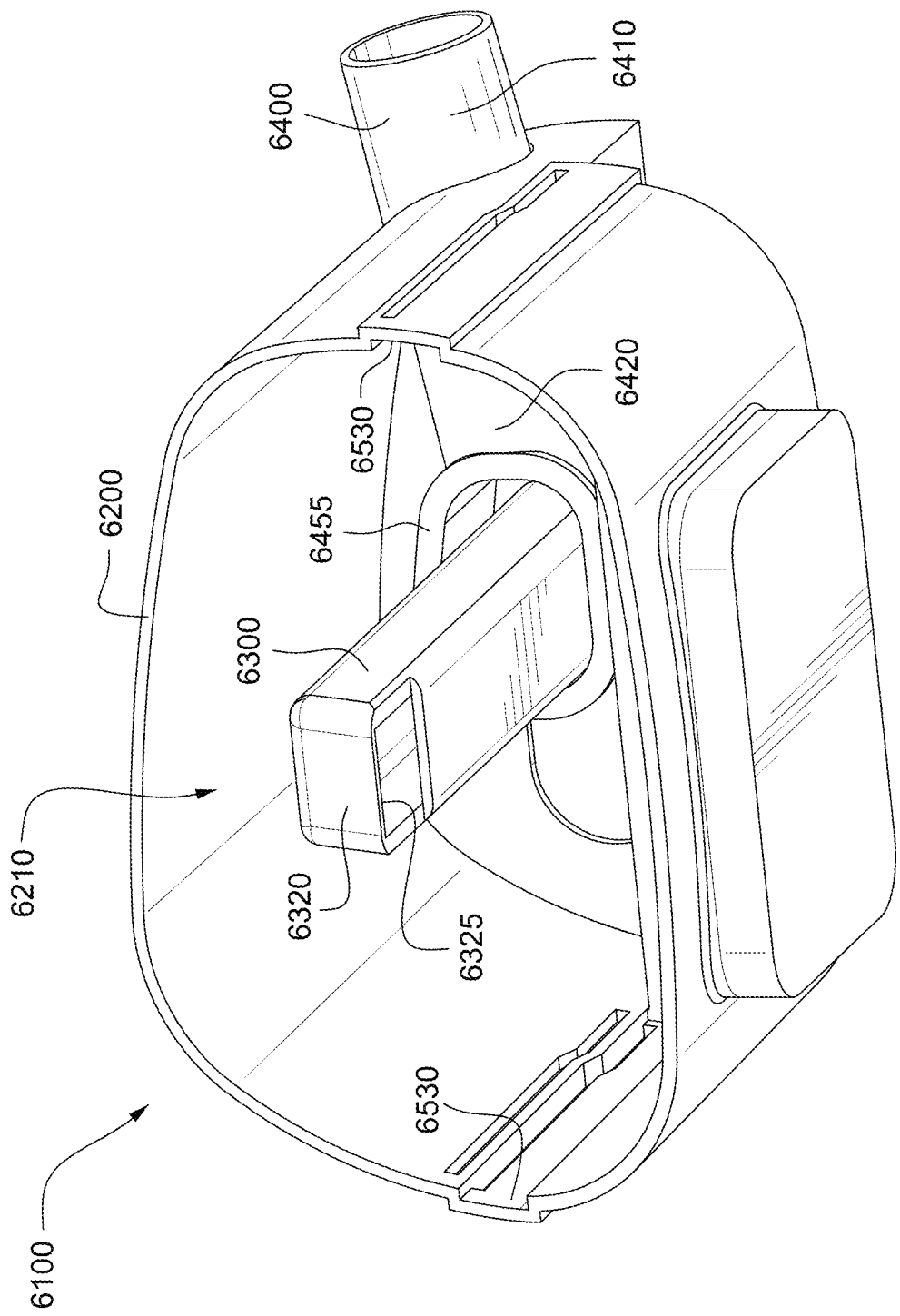

FIG. 31 is another perspective view of the reservoir dock shown in FIG. 30.

Figure 32:
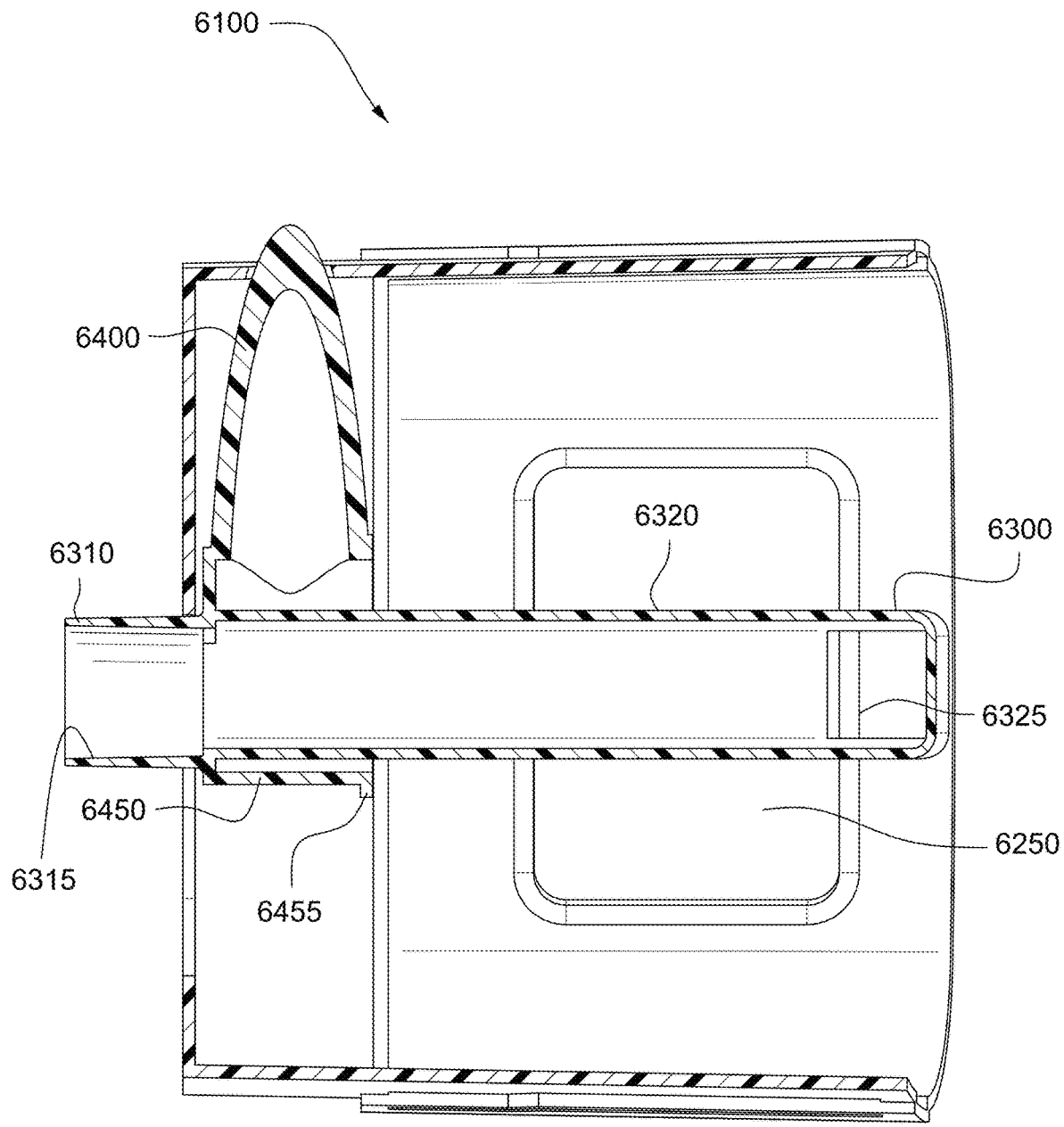

FIG. 32 is a cross-section of the reservoir dock shown in FIG. 30.

Figure 33:
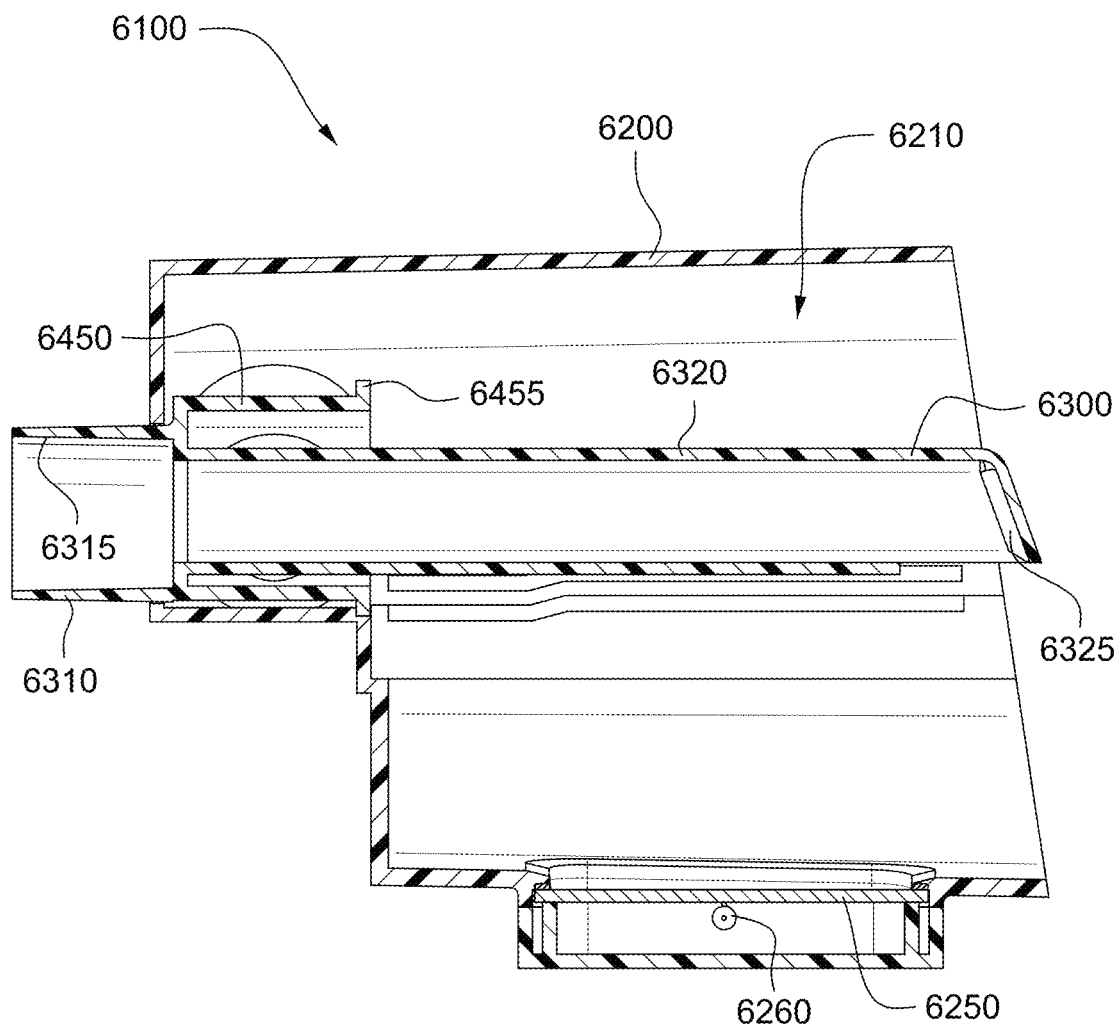

FIG. 33 is another cross-section of the reservoir dock shown in FIG. 30.

Figure 34:
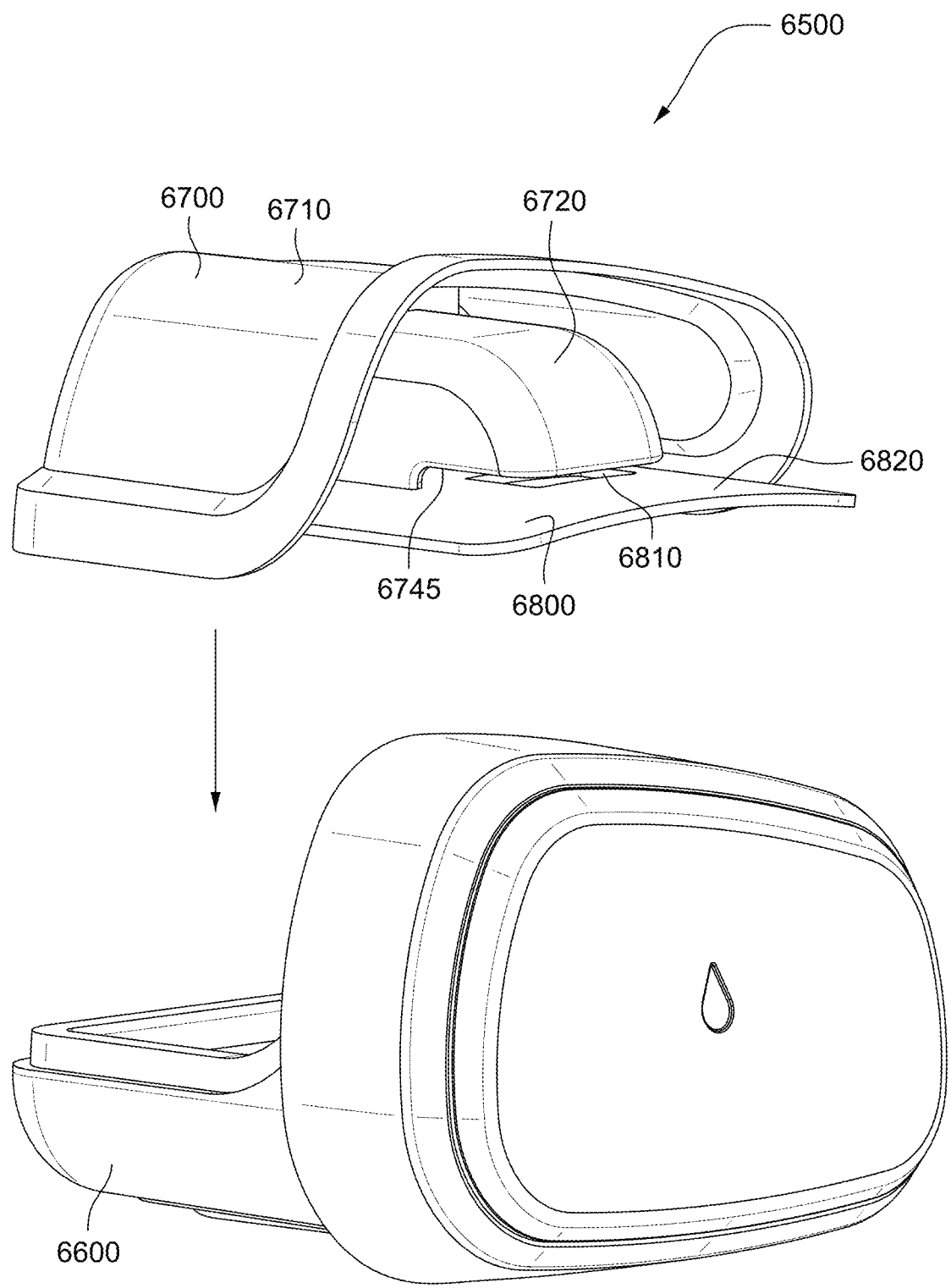

FIG. 34 is an exploded view of a water reservoir for a humidifier according to an example of the present technology.

Figure 35:
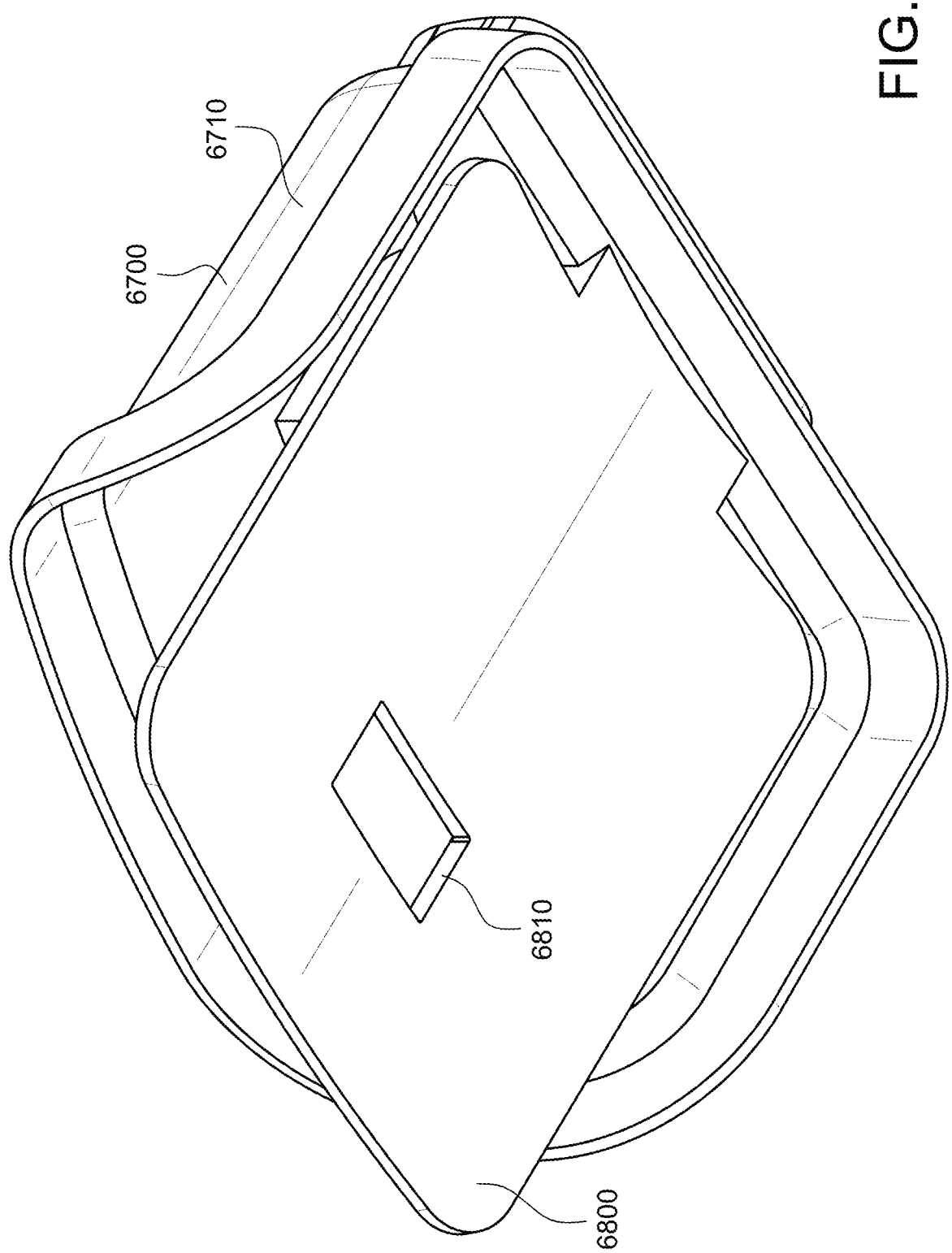

FIG. 35 is a perspective view of a reservoir lid of the water reservoir shown in FIG. 34.

Figure 36:
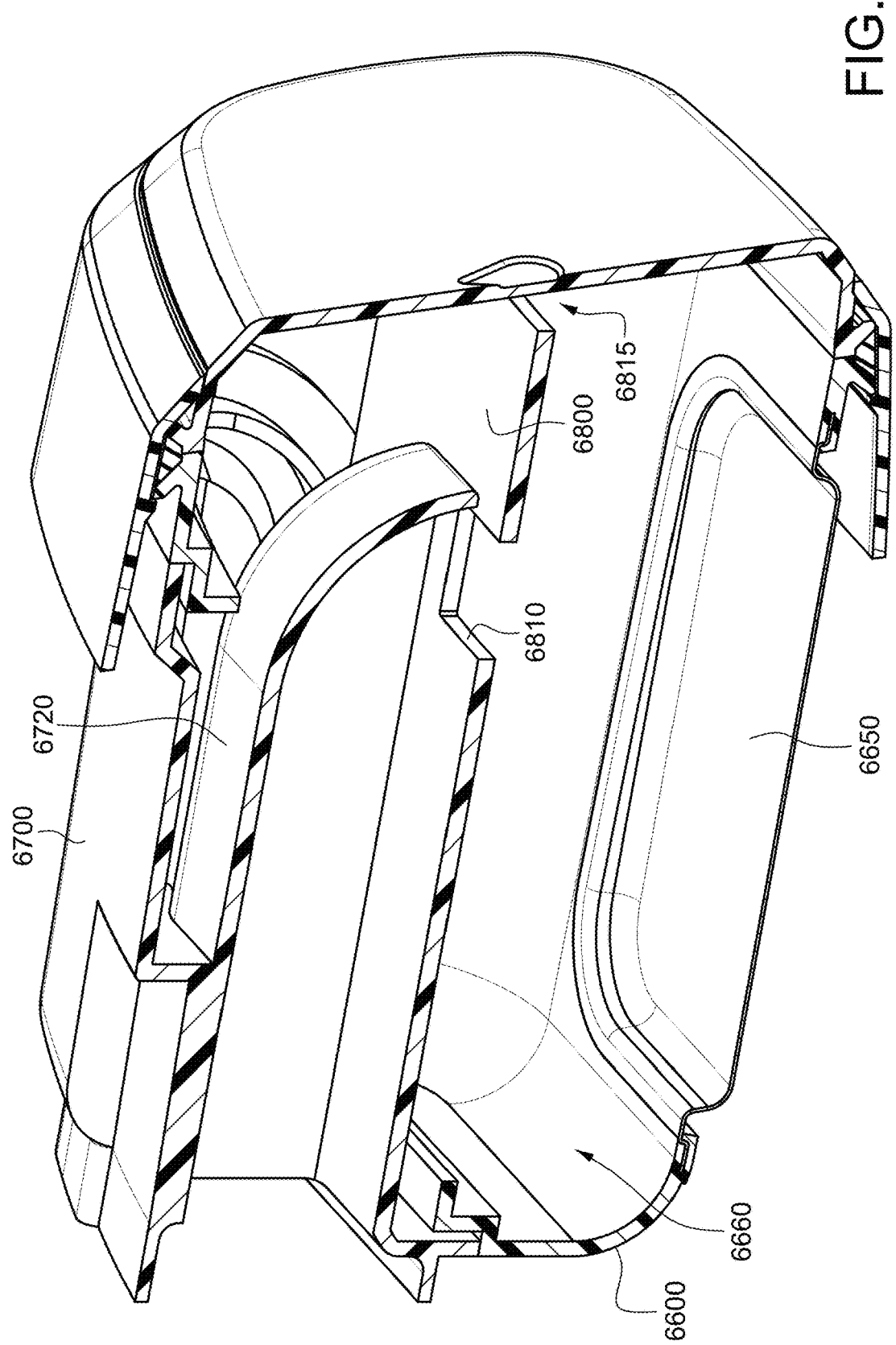

FIG. 36 is a cross-section of the water reservoir shown in FIG. 34 when the reservoir lid is coupled to the reservoir base.

Figure 37:
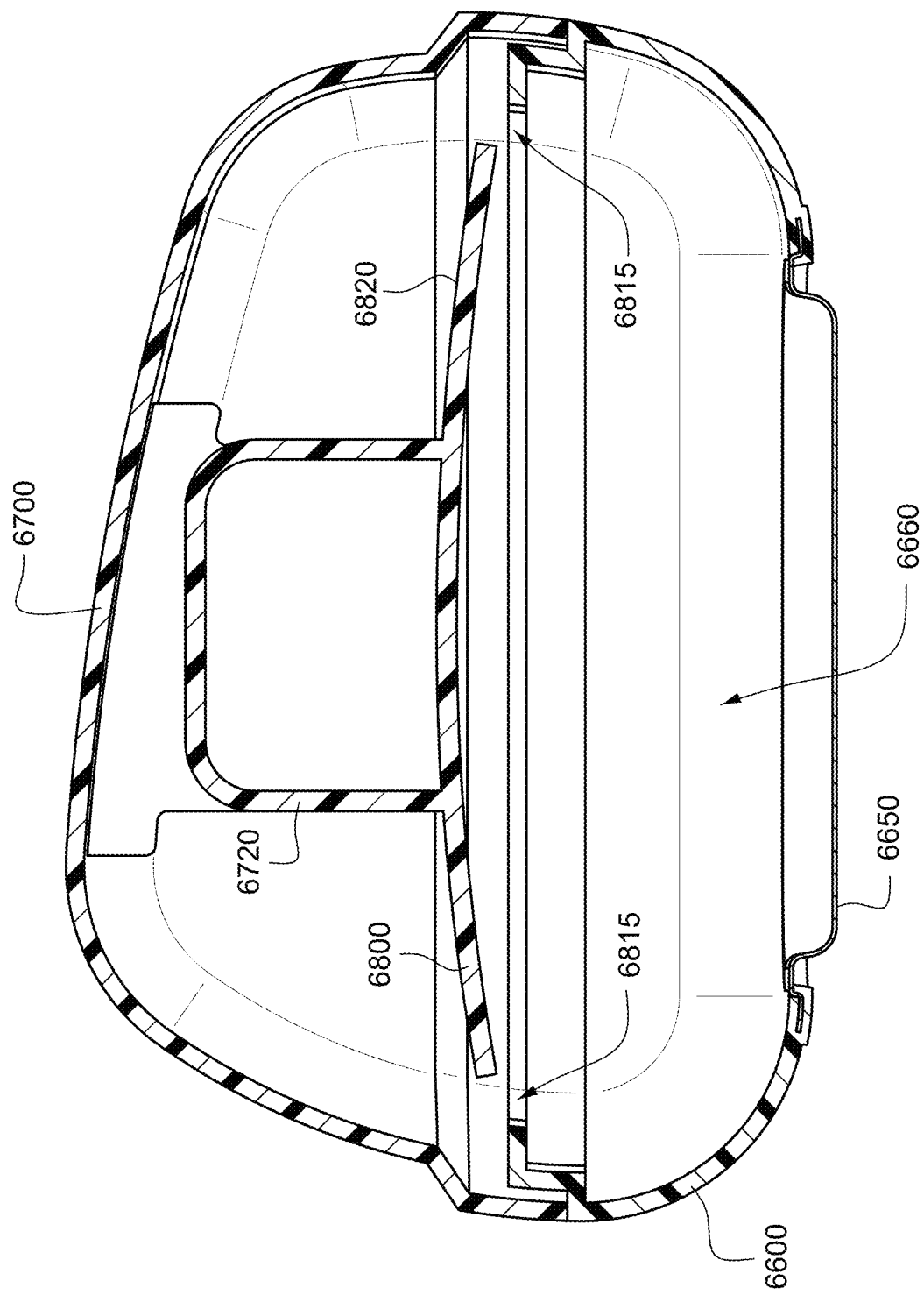

FIG. 37 is another cross-section of the water reservoir shown in FIG. 34 when the reservoir lid is coupled to the reservoir base.

Figure 38:
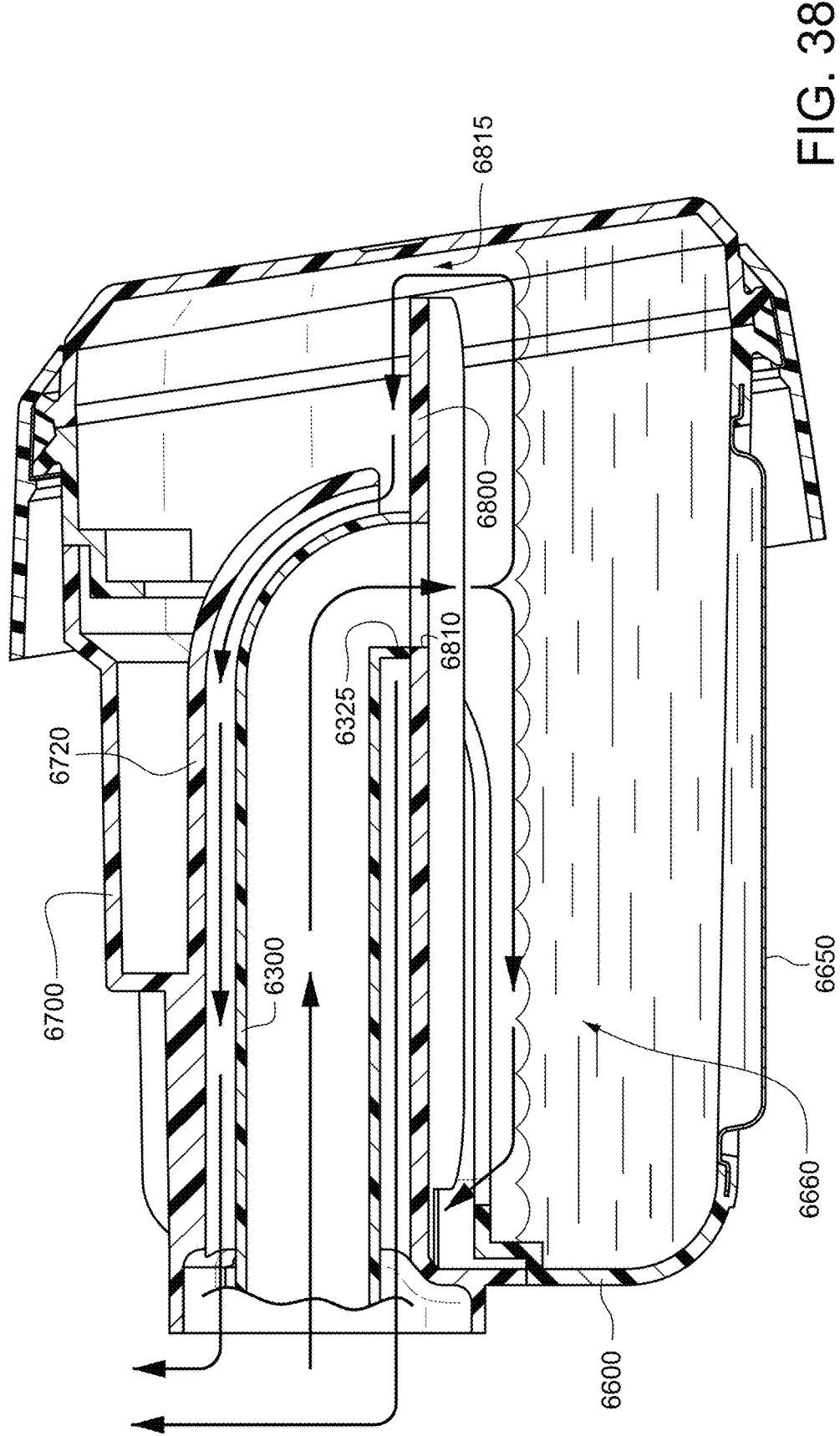

FIG. 38 is a cross-section showing the dock inlet conduit of the reservoir dock extending into the water reservoir of FIG. 34 when the water reservoir is coupled with the reservoir dock according to an example of the present technology, and showing flow paths through the humidifier according to an example of the present technology.

Figure 39:
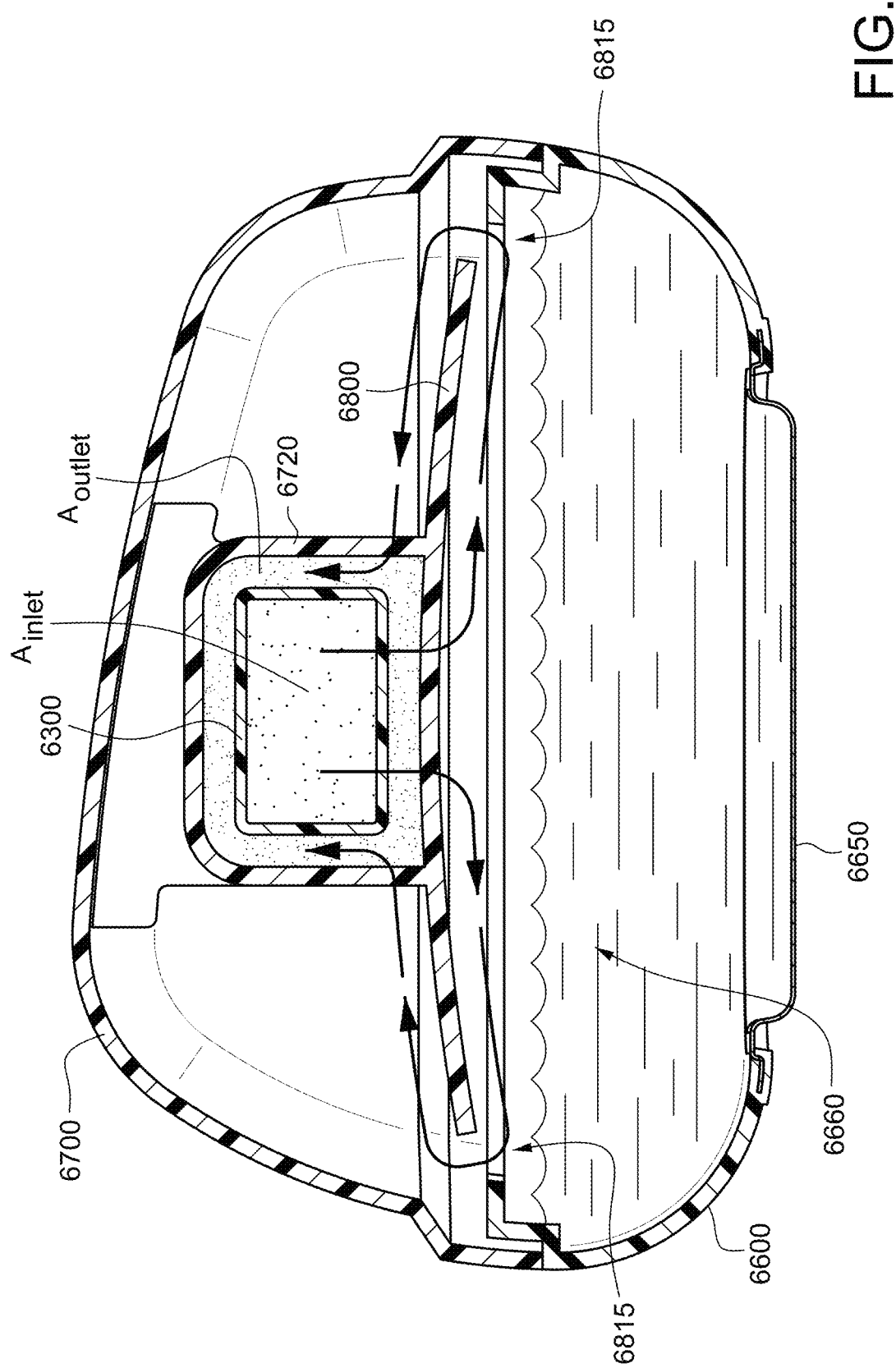

FIG. 39 is another cross-section showing the dock inlet conduit of the reservoir dock extending into the water reservoir of FIG. 34 when the water reservoir is coupled with the reservoir dock according to an example of the present technology, and showing flow paths through the humidifier according to an example of the present technology.

Figure 40:
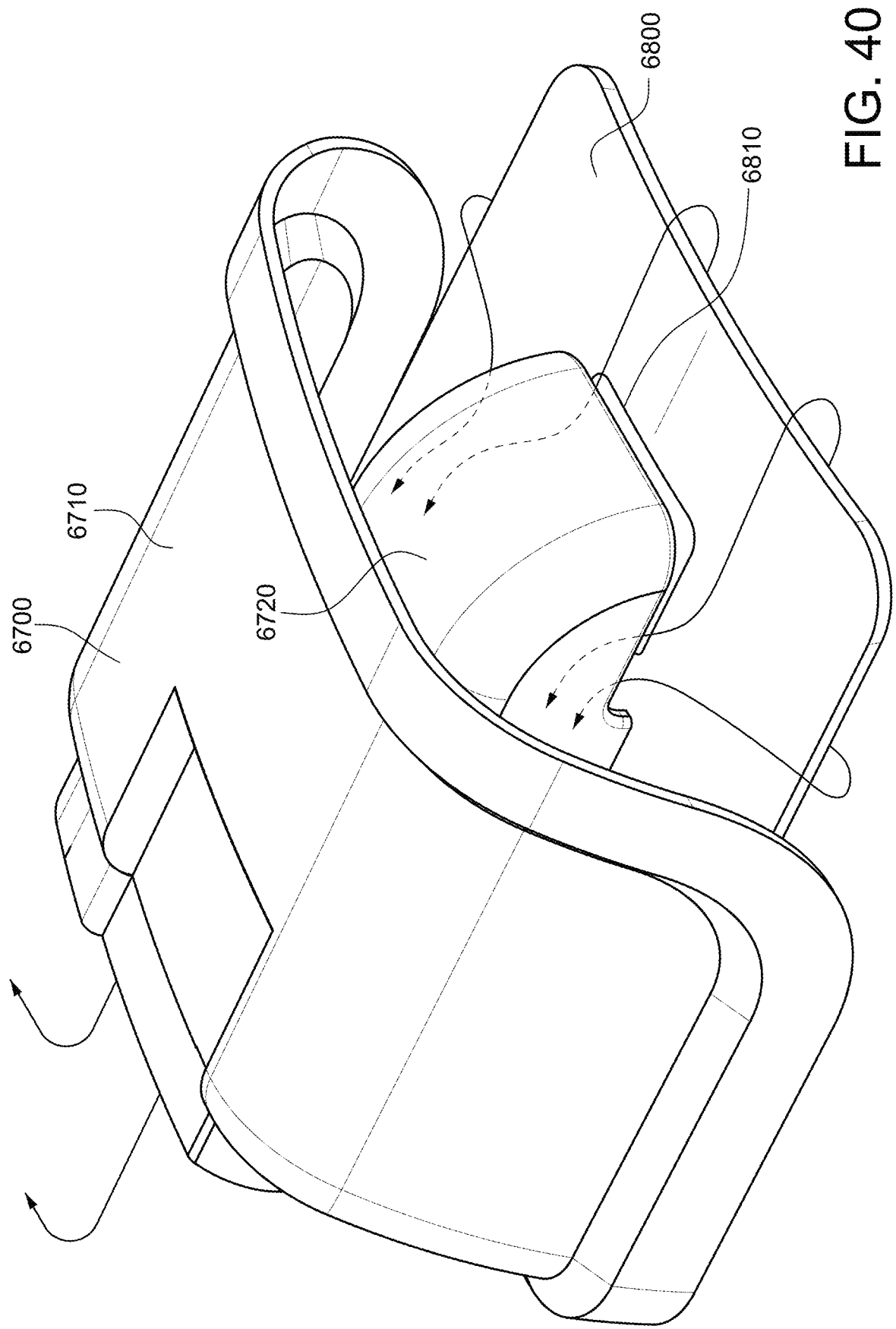

FIG. 40 is a perspective view of a reservoir lid of the water reservoir shown in FIG. 34, and showing flow paths through the humidifier according to an example of the present technology.

5 DETAILED DESCRIPTION OF EXAMPLES OF THE TECHNOLOGY

Before the present technology is described in further detail, it is to be understood that the technology is not limited to the particular examples described herein, which may vary. It is also to be understood that the terminology used in this disclosure is for the purpose of describing only the particular examples discussed herein, and is not intended to be limiting.

The following description is provided in relation to various examples which may share one or more common characteristics and/or features. It is to be understood that one or more features of any one example may be combinable with one or more features of another example or other examples. In addition, any single feature or combination of features in any of the examples may constitute a further example.

5.1 Therapy

In one form, the present technology comprises a method for treating a respiratory disorder comprising the step of applying positive pressure to the entrance of the airways of a patient 1000.

In certain examples of the present technology, a supply of air at positive pressure is provided to the nasal passages of the patient via one or both nares.

In certain examples of the present technology, mouth breathing is limited, restricted or prevented.

5.2 Treatment Systems

In one form, the present technology comprises an apparatus or device for treating a respiratory disorder. The apparatus or device may comprise an RPT device 4000 for supplying pressurised air to the patient 1000 via an air circuit 4170 to a patient interface 3000.

5.3 Patient Interface

A non-invasive patient interface 3000 in accordance with one aspect of the present technology comprises the following functional aspects: a seal-forming structure 3100, a plenum chamber 3200, a positioning and stabilising structure 3300, a vent 3400, one form of connection port 3600 for connection to air circuit 4170, and a forehead support 3700. In some forms a functional aspect may be provided by one or more physical components. In some forms, one physical component may provide one or more functional aspects. In use the seal-forming structure 3100 is arranged to surround an entrance to the airways of the patient so as to facilitate the supply of air at positive pressure to the airways.

If a patient interface is unable to comfortably deliver a minimum level of positive pressure to the airways, the patient interface may be unsuitable for respiratory pressure therapy.

The patient interface 3000 in accordance with one form of the present technology is constructed and arranged to be able to provide a supply of air at a positive pressure of at least 6 cmH$_2$O with respect to ambient.

The patient interface 3000 in accordance with one form of the present technology is constructed and arranged to be able to provide a supply of air at a positive pressure of at least 10 cmH$_2$O with respect to ambient.

The patient interface 3000 in accordance with one form of the present technology is constructed and arranged to be able to provide a supply of air at a positive pressure of at least 20 cmH$_2$O with respect to ambient.

5.4 RPT Device

An RPT device 4000 in accordance with one aspect of the present technology is shown in FIG. 4A, and comprises mechanical, pneumatic, and/or electrical components and is configured to execute one or more algorithms 4300. The RPT device 4000 may be configured to generate a flow of air for delivery to a patient's airways, such as to treat one or more of the respiratory conditions described elsewhere in the present document.

In one form, the RPT device 4000 is constructed and arranged to be capable of delivering a flow of air in a range of −20 L/min to +150 L/min while maintaining a positive pressure of at least 6 cmH$_2$O, or at least 10 cmH$_2$O, or at least 20 cmH$_2$O.

The RPT device may have an external housing 4010, formed in two parts, an upper portion 4012 and a lower portion 4014. Furthermore, the external housing 4010 may include one or more panel(s) 4015. The RPT device 4000 comprises a chassis 4016 that supports one or more internal components of the RPT device 4000. The RPT device 4000 may include a handle 4018.

A schematic diagram of a pneumatic circuit of the RPT device 4000 according to an example of the present technology is shown in FIGS. 4B and 4C. The pneumatic path of the RPT device 4000 may comprise one or more air path items, e.g., an inlet air filter 4112, an inlet muffler 4122, a pressure generator 4140 capable of supplying air at positive pressure (e.g., a blower 4142), an outlet muffler 4124 and one or more transducers 4270, such as pressure sensors 4272 and flow rate sensors 4274.

One or more of the air path items may be located within a removable unitary structure which will be referred to as a pneumatic block 4020. The pneumatic block 4020 may be located within the external housing 4010. In one form a pneumatic block 4020 is supported by, or formed as part of the chassis 4016.

The RPT device 4000 may have an electrical power supply 4210, one or more input devices 4220, a central controller 4230, a therapy device controller 4240, a pressure generator 4140, one or more protection circuits 4250, memory 4260, transducers 4270, data communication interface 4280 and one or more output devices 4290. Electrical components 4200 may be mounted on a single Printed Circuit Board Assembly (PCBA) 4202. In an alternative form, the RPT device 4000 may include more than one PCBA 4202.

5.4.1 RPT Device Mechanical & Pneumatic Components

An RPT device may comprise one or more of the following components in an integral unit. In an alternative form, one or more of the following components may be located as respective separate units.

5.4.1.1 Air Filter(s)

An RPT device in accordance with one form of the present technology may include an air filter 4110, or a plurality of air filters 4110.

In one form, an inlet air filter 4112 is located at the beginning of the pneumatic path upstream of a pressure generator 4140.

In one form, an outlet air filter 4114, for example an antibacterial filter, is located between an outlet of the pneumatic block 4020 and a patient interface 3000.

5.4.1.2 Muffler(s)

An RPT device in accordance with one form of the present technology may include a muffler 4120, or a plurality of mufflers 4120.

In one form of the present technology, an inlet muffler 4122 is located in the pneumatic path upstream of a pressure generator 4140.

In one form of the present technology, an outlet muffler 4124 is located in the pneumatic path between the pressure generator 4140 and a patient interface 3000.

5.4.1.3 Pressure Generator

In one form of the present technology, a pressure generator 4140 for producing a flow, or a supply, of air at positive pressure is a controllable blower 4142. For example the blower 4142 may include a brushless DC motor 4144 with one or more impellers housed in a volute. The blower may be capable of delivering a supply of air, for example at a rate of up to about 120 litres/minute, at a positive pressure in a range from about 4 cmH$_2$O to about 20 cmH$_2$O, or in other forms up to about 30 cmH$_2$O. The blower may be as described in any one of the following patents or patent applications the contents of which are incorporated herein by reference in their entirety: U.S. Pat. Nos. 7,866,944; 8,638,014; 8,636,479; and PCT Patent Application Publication No. WO 2013/020167.

The pressure generator 4140 is under the control of the therapy device controller 4240.

In other forms, a pressure generator 4140 may be a piston-driven pump, a pressure regulator connected to a high pressure source (e.g. compressed air reservoir), or a bellows.

5.4.1.4 Transducer(s)

Transducers may be internal of the RPT device, or external of the RPT device. External transducers may be located for example on or form part of the air circuit, e.g., the patient interface. External transducers may be in the form of non-contact sensors such as a Doppler radar movement sensor that transmit or transfer data to the RPT device.

In one form of the present technology, one or more transducers 4270 are located upstream and/or downstream of the pressure generator 4140. The one or more transducers 4270 may be constructed and arranged to generate signals representing properties of the flow of air such as a flow rate, a pressure or a temperature at that point in the pneumatic path.

In one form of the present technology, one or more transducers 4270 may be located proximate to the patient interface 3000.

In one form, a signal from a transducer 4270 may be filtered, such as by low-pass, high-pass or band-pass filtering.

5.4.1.4.1 Flow Rate Sensor

A flow rate sensor 4274 in accordance with the present technology may be based on a differential pressure transducer, for example, an SDP600 Series differential pressure transducer from SENSIRION.

In one form, a signal representing a flow rate from the flow rate sensor 4274 is received by the central controller 4230.

5.4.1.4.2 Pressure Sensor

A pressure sensor 4272 in accordance with the present technology is located in fluid communication with the pneumatic path. An example of a suitable pressure sensor is a transducer from the HONEYWELL ASDX series. An alternative suitable pressure sensor is a transducer from the NPA Series from GENERAL ELECTRIC.

In one form, a signal from the pressure sensor 4272 is received by the central controller 4230.

5.4.1.4.3 Motor Speed Transducer

In one form of the present technology a motor speed transducer 4276 is used to determine a rotational velocity of the motor 4144 and/or the blower 4142. A motor speed signal from the motor speed transducer 4276 may be provided to the therapy device controller 4240. The motor speed transducer 4276 may, for example, be a speed sensor, such as a Hall effect sensor.

5.4.1.5 Anti-Spill Back Valve

In one form of the present technology, an anti-spill back valve 4160 is located between the humidifier 5000 and the pneumatic block 4020. The anti-spill back valve is constructed and arranged to reduce the risk that water will flow upstream from the humidifier 5000, for example to the motor 4144.

5.4.2 RPT Device Electrical Components

5.4.2.1 Power Supply

A power supply 4210 may be located internal or external of the external housing 4010 of the RPT device 4000.

In one form of the present technology, power supply 4210 provides electrical power to the RPT device 4000 only. In another form of the present technology, power supply 4210 provides electrical power to both RPT device 4000 and humidifier 5000.

5.4.2.2 Input Devices

In one form of the present technology, an RPT device 4000 includes one or more input devices 4220 in the form of buttons, switches or dials to allow a person to interact with the device. The buttons, switches or dials may be physical devices, or software devices accessible via a touch screen. The buttons, switches or dials may, in one form, be physically connected to the external housing 4010, or may, in another form, be in wireless communication with a receiver that is in electrical connection to the central controller 4230.

In one form, the input device 4220 may be constructed and arranged to allow a person to select a value and/or a menu option.

5.4.2.3 Central Controller

In one form of the present technology, the central controller 4230 is one or a plurality of processors suitable to control an RPT device 4000.

Suitable processors may include an x86 INTEL processor, a processor based on ARM® Cortex®-M processor from ARM Holdings such as an STM32 series microcontroller from ST MICROELECTRONIC. In certain alternative forms of the present technology, a 32-bit RISC CPU, such as an STR9 series microcontroller from ST MICROELECTRONICS or a 16-bit RISC CPU such as a processor from the MSP430 family of microcontrollers, manufactured by TEXAS INSTRUMENTS may also be suitable.

In one form of the present technology, the central controller 4230 is a dedicated electronic circuit.

In one form, the central controller 4230 is an application-specific integrated circuit. In another form, the central controller 4230 comprises discrete electronic components.

The central controller 4230 may be configured to receive input signal(s) from one or more transducers 4270, one or more input devices 4220, and the humidifier 5000.

The central controller 4230 may be configured to provide output signal(s) to one or more of an output device 4290, a therapy device controller 4240, a data communication interface 4280, and the humidifier 5000.

In some forms of the present technology, the central controller 4230 is configured to implement the one or more methodologies described herein, such as the one or more algorithms 4300 expressed as computer programs stored in a non-transitory computer readable storage medium, such as memory 4260. In some forms of the present technology, the central controller 4230 may be integrated with an RPT device 4000. However, in some forms of the present technology, some methodologies may be performed by a remotely located device. For example, the remotely located device may determine control settings for a ventilator or detect respiratory related events by analysis of stored data such as from any of the sensors described herein.

5.4.2.4 Clock

The RPT device 4000 may include a clock 4232 that is connected to the central controller 4230.

5.4.2.5 Therapy Device Controller

In one form of the present technology, therapy device controller 4240 is a therapy control module 4330 that forms part of the algorithms 4300 executed by the central controller 4230.

In one form of the present technology, therapy device controller 4240 is a dedicated motor control integrated circuit. For example, in one form a MC33035 brushless DC motor controller, manufactured by ONSEMI is used.

5.4.2.6 Protection Circuits

The one or more protection circuits 4250 in accordance with the present technology may comprise an electrical protection circuit, a temperature and/or pressure safety circuit.

5.4.2.7 Memory

In accordance with one form of the present technology the RPT device 4000 includes memory 4260, e.g., non-volatile memory. In some forms, memory 4260 may include battery powered static RAM. In some forms, memory 4260 may include volatile RAM.

Memory 4260 may be located on the PCBA 4202. Memory 4260 may be in the form of EEPROM, or NAND flash.

Additionally or alternatively, RPT device 4000 includes a removable form of memory 4260, for example a memory card made in accordance with the Secure Digital (SD) standard.

In one form of the present technology, the memory 4260 acts as a non-transitory computer readable storage medium on which is stored computer program instructions expressing the one or more methodologies described herein, such as the one or more algorithms 4300.

5.4.2.8 Data Communication Systems

In one form of the present technology, a data communication interface 4280 is provided, and is connected to the central controller 4230. Data communication interface 4280 may be connectable to a remote external communication network 4282 and/or a local external communication network 4284. The remote external communication network 4282 may be connectable to a remote external device 4286. The local external communication network 4284 may be connectable to a local external device 4288.

In one form, data communication interface 4280 is part of the central controller 4230. In another form, data communication interface 4280 is separate from the central controller 4230, and may comprise an integrated circuit or a processor.

In one form, remote external communication network 4282 is the Internet. The data communication interface 4280 may use wired communication (e.g. via Ethernet, or optical fibre) or a wireless protocol (e.g. CDMA, GSM, LTE) to connect to the Internet.

In one form, local external communication network 4284 utilises one or more communication standards, such as Bluetooth, or a consumer infrared protocol.

In one form, remote external device 4286 is one or more computers, for example a cluster of networked computers. In one form, remote external device 4286 may be virtual computers, rather than physical computers. In either case, such a remote external device 4286 may be accessible to an appropriately authorised person such as a clinician.

The local external device 4288 may be a personal computer, mobile phone, tablet or remote control.

5.4.2.9 Output Devices Including Optional Display, Alarms

An output device 4290 in accordance with the present technology may take the form of one or more of a visual, audio and haptic unit. A visual display may be a Liquid Crystal Display (LCD) or Light Emitting Diode (LED) display.

5.4.2.9.1 Display Driver

A display driver 4292 receives as an input the characters, symbols, or images intended for display on the display 4294, and converts them to commands that cause the display 4294 to display those characters, symbols, or images.

5.4.2.9.2 Display

A display 4294 is configured to visually display characters, symbols, or images in response to commands received from the display driver 4292. For example, the display 4294 may be an eight-segment display, in which case the display driver 4292 converts each character or symbol, such as the figure "0", to eight logical signals indicating whether the eight respective segments are to be activated to display a particular character or symbol.

5.4.3 RPT Device Algorithms

As mentioned above, in some forms of the present technology, the central controller 4230 may be configured to implement one or more algorithms 4300 expressed as computer programs stored in a non-transitory computer readable storage medium, such as memory 4260. The algorithms 4300 are generally grouped into groups referred to as modules, e.g., see FIG. 4D.

5.4.3.1 Pre-Processing Module

A pre-processing module 4310 in accordance with one form of the present technology receives as an input a signal from a transducer 4270, for example a flow rate sensor 4274 or pressure sensor 4272, and performs one or more process steps to calculate one or more output values that will be used as an input to another module, for example a therapy engine module 4320.

In one form of the present technology, the output values include the interface or mask pressure Pm, the respiratory flow rate Qr, and the leak flow rate Ql.

In various forms of the present technology, the pre-processing module 4310 comprises one or more of the following algorithms: pressure compensation 4312, vent flow rate estimation 4314, leak flow rate estimation 4316, and respiratory flow rate estimation 4318.

5.4.3.1.1 Pressure Compensation

In one form of the present technology, a pressure compensation algorithm 4312 receives as an input a signal indicative of the pressure in the pneumatic path proximal to an outlet of the pneumatic block. The pressure compensation algorithm 4312 estimates the pressure drop through the air circuit 4170 and provides as an output an estimated pressure, Pm, in the patient interface 3000.

5.4.3.1.2 Vent Flow Rate Estimation

In one form of the present technology, a vent flow rate estimation algorithm 4314 receives as an input an estimated pressure, Pm, in the patient interface 3000 and estimates a vent flow rate of air, Qv, from a vent 3400 in a patient interface 3000.

5.4.3.1.3 Leak Flow Rate Estimation

In one form of the present technology, a leak flow rate estimation algorithm 4316 receives as an input a total flow rate, Qt, and a vent flow rate Qv, and provides as an output an estimate of the leak flow rate Ql. In one form, the leak flow rate estimation algorithm estimates the leak flow rate Ql by calculating an average of the difference between total flow rate Qt and vent flow rate Qv over a period sufficiently long to include several breathing cycles, e.g. about 10 seconds.

In one form, the leak flow rate estimation algorithm 4316 receives as an input a total flow rate Qt, a vent flow rate Qv, and an estimated pressure, Pm, in the patient interface 3000, and provides as an output a leak flow rate Ql, by calculating a leak conductance, and determining a leak flow rate Ql to be a function of leak conductance and pressure, Pm. Leak conductance is calculated as the quotient of low pass filtered non-vent flow rate equal to the difference between total flow rate Qt and vent flow rate Qv, and low pass filtered square root of pressure Pm, where the low pass filter time constant has a value sufficiently long to include several breathing cycles, e.g. about 10 seconds. The leak flow rate Ql may be estimated as the product of leak conductance and a function of pressure, Pm.

5.4.3.1.4 Respiratory Flow Rate Estimation

In one form of the present technology, a respiratory flow rate estimation algorithm 4318 receives as an input a total flow rate, Qt, a vent flow rate, Qv, and a leak flow rate, Ql, and estimates a respiratory flow rate of air, Qr, to the patient, by subtracting the vent flow rate Qv and the leak flow rate Ql from the total flow rate Qt.

5.4.3.2 Therapy Engine Module

In one form of the present technology, a therapy engine module 4320 receives as inputs one or more of a pressure, Pm, in a patient interface 3000, and a respiratory flow rate of air to a patient, Qr, and provides as an output one or more therapy parameters.

In one form of the present technology, a therapy parameter is a treatment pressure Pt.

In one form of the present technology, therapy parameters are one or more of an amplitude of a pressure variation, a base pressure, and a target ventilation.

In various forms, the therapy engine module 4320 comprises one or more of the following algorithms: phase determination 4321, waveform determination 4322, ventilation determination 4323, inspiratory flow limitation determination 4324, apnea/hypopnea determination 4325, snore determination 4326, airway patency determination 4327, target ventilation determination 4328, and therapy parameter determination 4329.

5.4.3.2.1 Phase Determination

In one form of the present technology, the RPT device 4000 does not determine phase.

In one form of the present technology, a phase determination algorithm 4321 receives as an input a signal indicative of respiratory flow rate, Qr, and provides as an output a phase $\Phi$ of a current breathing cycle of a patient 1000.

In some forms, known as discrete phase determination, the phase output $\Phi$ is a discrete variable. One implementation of discrete phase determination provides a bi-valued phase output $\Phi$ with values of either inhalation or exhalation, for example represented as values of 0 and 0.5 revolutions respectively, upon detecting the start of spontaneous inhalation and exhalation respectively. RPT devices 4000 that "trigger" and "cycle" effectively perform discrete phase determination, since the trigger and cycle points are the instants at which the phase changes from exhalation to inhalation and from inhalation to exhalation, respectively. In one implementation of bi-valued phase determination, the phase output $\Phi$ is determined to have a discrete value of 0 (thereby "triggering" the RPT device 4000) when the respiratory flow rate Qr has a value that exceeds a positive threshold, and a discrete value of 0.5 revolutions (thereby "cycling" the RPT device 4000) when a respiratory flow rate Qr has a value that is more negative than a negative threshold.

Another implementation of discrete phase determination provides a tri-valued phase output $\Phi$ with a value of one of inhalation, mid-inspiratory pause, and exhalation.

In other forms, known as continuous phase determination, the phase output $\Phi$ is a continuous variable, for example varying from 0 to 1 revolutions, or 0 to $2\pi$ radians. RPT devices 4000 that perform continuous phase determination may trigger and cycle when the continuous phase reaches 0 and 0.5 revolutions, respectively. In one implementation of continuous phase determination, a continuous value of phase $\Phi$ is determined using a fuzzy logic analysis of the respiratory flow rate Qr. A continuous value of phase determined in this implementation is often referred to as "fuzzy phase". In one implementation of a fuzzy phase determination algorithm 4321, the following rules are applied to the respiratory flow rate Qr:

1. If the respiratory flow rate is zero and increasing fast then the phase is 0 revolutions.
2. If the respiratory flow rate is large positive and steady then the phase is 0.25 revolutions.
3. If the respiratory flow rate is zero and falling fast, then the phase is 0.5 revolutions.
4. If the respiratory flow rate is large negative and steady then the phase is 0.75 revolutions.
5. If the respiratory flow rate is zero and steady and the 5-second low-pass filtered absolute value of the respiratory flow rate is large then the phase is 0.9 revolutions.
6. If the respiratory flow rate is positive and the phase is expiratory, then the phase is 0 revolutions.
7. If the respiratory flow rate is negative and the phase is inspiratory, then the phase is 0.5 revolutions.
8. If the 5-second low-pass filtered absolute value of the respiratory flow rate is large, the phase is increasing at a steady rate equal to the patient's breathing rate, low-pass filtered with a time constant of 20 seconds.

The output of each rule may be represented as a vector whose phase is the result of the rule and whose magnitude is the fuzzy extent to which the rule is true. The fuzzy extent to which the respiratory flow rate is "large", "steady", etc. is determined with suitable membership functions. The results of the rules, represented as vectors, are then combined by some function such as taking the centroid. In such a combination, the rules may be equally weighted, or differently weighted.

In another implementation of continuous phase determination, the inhalation time Ti and the exhalation time Te are first estimated from the respiratory flow rate Qr. The phase $\Phi$ is then determined as the half the proportion of the inhalation time Ti that has elapsed since the previous trigger instant, or 0.5 revolutions plus half the proportion of the exhalation time Te that has elapsed since the previous cycle instant (whichever was more recent).

5.4.3.2.2 Waveform Determination

In one form of the present technology, the therapy parameter determination algorithm 4329 provides an approximately constant treatment pressure throughout a respiratory cycle of a patient.

In other forms of the present technology, the therapy control module 4330 controls the pressure generator 4140 to provide a treatment pressure Pt that varies as a function of phase $\Phi$ of a respiratory cycle of a patient according to a waveform template $\Pi(\Phi)$.

In one form of the present technology, a waveform determination algorithm 4322 provides a waveform template $\Pi(\Phi)$ with values in the range [0, 1] on the domain of phase values $\Phi$ provided by the phase determination algorithm 4321 to be used by the therapy parameter determination algorithm 4329.

In one form, suitable for either discrete or continuously-valued phase, the waveform template $\Pi(\Phi)$ is a square-wave template, having a value of 1 for values of phase up to and including 0.5 revolutions, and a value of 0 for values of phase above 0.5 revolutions. In one form, suitable for continuously-valued phase, the waveform template $\Pi(\Phi)$ comprises two smoothly curved portions, namely a smoothly curved (e.g. raised cosine) rise from 0 to 1 for values of phase up to 0.5 revolutions, and a smoothly curved (e.g. exponential) decay from 1 to 0 for values of phase above 0.5 revolutions. In one form, suitable for continuously-valued phase, the waveform template Π(Φ) is based on a square wave, but with a smooth rise from 0 to 1 for values of phase up to a "rise time" that is less than 0.5 revolutions, and a smooth fall from 1 to 0 for values of phase within a "fall time" after 0.5 revolutions, with a "fall time" that is less than 0.5 revolutions.

In some forms of the present technology, the waveform determination algorithm 4322 selects a waveform template Π(Φ) from a library of waveform templates, dependent on a setting of the RPT device. Each waveform template Π(Φ) in the library may be provided as a lookup table of values Π against phase values Φ. In other forms, the waveform determination algorithm 4322 computes a waveform template Π(Φ) "on the fly" using a predetermined functional form, possibly parametrised by one or more parameters (e.g. time constant of an exponentially curved portion). The parameters of the functional form may be predetermined or dependent on a current state of the patient 1000.

In some forms of the present technology, suitable for discrete bi-valued phase of either inhalation (Φ=0 revolutions) or exhalation (Φ=0.5 revolutions), the waveform determination algorithm 4322 computes a waveform template Π "on the fly" as a function of both discrete phase Φ and time t measured since the most recent trigger instant. In one such form, the waveform determination algorithm 4322 computes the waveform template Π(Φ, t) in two portions (inspiratory and expiratory) as follows:

$$\Pi(\Phi, t) = \begin{cases} \prod_i (t), & \Phi = 0 \\ \prod_e (t - T_i), & \Phi = 0.5 \end{cases}$$

where $\Pi_i(t)$ and $\Pi_e(t)$ are inspiratory and expiratory portions of the waveform template Π(Φ, t). In one such form, the inspiratory portion $\Pi_i(t)$ of the waveform template is a smooth rise from 0 to 1 parametrised by a rise time, and the expiratory portion $\Pi_e(t)$ of the waveform template is a smooth fall from 1 to 0 parametrised by a fall time.

5.4.3.2.3 Ventilation Determination

In one form of the present technology, a ventilation determination algorithm 4323 receives an input a respiratory flow rate Qr, and determines a measure indicative of current patient ventilation, Vent.

In some implementations, the ventilation determination algorithm 4323 determines a measure of ventilation Vent that is an estimate of actual patient ventilation. One such implementation is to take half the absolute value of respiratory flow rate, Qr, optionally filtered by low-pass filter such as a second order Bessel low-pass filter with a corner frequency of 0.11 Hz.

In other implementations, the ventilation determination algorithm 4323 determines a measure of ventilation Vent that is broadly proportional to actual patient ventilation. One such implementation estimates peak respiratory flow rate Qpeak over the inspiratory portion of the cycle. This and many other procedures involving sampling the respiratory flow rate Qr produce measures which are broadly proportional to ventilation, provided the flow rate waveform shape does not vary very much (here, the shape of two breaths is taken to be similar when the flow rate waveforms of the breaths normalised in time and amplitude are similar). Some simple examples include the median positive respiratory flow rate, the median of the absolute value of respiratory flow rate, and the standard deviation of flow rate. Arbitrary linear combinations of arbitrary order statistics of the absolute value of respiratory flow rate using positive coefficients, and even some using both positive and negative coefficients, are approximately proportional to ventilation. Another example is the mean of the respiratory flow rate in the middle K proportion (by time) of the inspiratory portion, where 0<K<1. There is an arbitrarily large number of measures that are exactly proportional to ventilation if the flow rate shape is constant.

5.4.3.2.4 Determination of Inspiratory Flow Limitation

In one form of the present technology, the central controller 4230 executes an inspiratory flow limitation determination algorithm 4324 for the determination of the extent of inspiratory flow limitation.

In one form, the inspiratory flow limitation determination algorithm 4324 receives as an input a respiratory flow rate signal Qr and provides as an output a metric of the extent to which the inspiratory portion of the breath exhibits inspiratory flow limitation.

In one form of the present technology, the inspiratory portion of each breath is identified by a zero-crossing detector. A number of evenly spaced points (for example, sixty-five), representing points in time, are interpolated by an interpolator along the inspiratory flow rate-time curve for each breath. The curve described by the points is then scaled by a scalar to have unity length (duration/period) and unity area to remove the effects of changing breathing rate and depth. The scaled breaths are then compared in a comparator with a pre-stored template representing a normal unobstructed breath, similar to the inspiratory portion of the breath shown in FIG. 6A. Breaths deviating by more than a specified threshold (typically 1 scaled unit) at any time during the inspiration from this template, such as those due to coughs, sighs, swallows and hiccups, as determined by a test element, are rejected. For non-rejected data, a moving average of the first such scaled point is calculated by the central controller 4230 for the preceding several inspiratory events. This is repeated over the same inspiratory events for the second such point, and so on. Thus, for example, sixty five scaled data points are generated by the central controller 4230, and represent a moving average of the preceding several inspiratory events, e.g., three events. The moving average of continuously updated values of the (e.g., sixty five) points are hereinafter called the "scaled flow rate", designated as Qs(t). Alternatively, a single inspiratory event can be utilised rather than a moving average.

From the scaled flow rate, two shape factors relating to the determination of partial obstruction may be calculated.

Shape factor 1 is the ratio of the mean of the middle (e.g. thirty-two) scaled flow rate points to the mean overall (e.g. sixty-five) scaled flow rate points. Where this ratio is in excess of unity, the breath will be taken to be normal. Where the ratio is unity or less, the breath will be taken to be obstructed. A ratio of about 1.17 is taken as a threshold between partially obstructed and unobstructed breathing, and equates to a degree of obstruction that would permit maintenance of adequate oxygenation in a typical patient.

Shape factor 2 is calculated as the RMS deviation from unit scaled flow rate, taken over the middle (e.g. thirty two) points. An RMS deviation of about 0.2 units is taken to be normal. An RMS deviation of zero is taken to be a totally flow-limited breath. The closer the RMS deviation to zero, the breath will be taken to be more flow limited.

Shape factors 1 and 2 may be used as alternatives, or in combination. In other forms of the present technology, the number of sampled points, breaths and middle points may differ from those described above. Furthermore, the threshold values can be other than those described.

5.4.3.2.5 Determination of Apneas and Hypopneas

In one form of the present technology, the central controller 4230 executes an apnea/hypopnea determination algorithm 4325 for the determination of the presence of apneas and/or hypopneas.

In one form, the apnea/hypopnea determination algorithm 4325 receives as an input a respiratory flow rate signal Qr and provides as an output a flag that indicates that an apnea or a hypopnea has been detected.

In one form, an apnea will be said to have been detected when a function of respiratory flow rate Qr falls below a flow rate threshold for a predetermined period of time. The function may determine a peak flow rate, a relatively short-term mean flow rate, or a flow rate intermediate of relatively short-term mean and peak flow rate, for example an RMS flow rate. The flow rate threshold may be a relatively long-term measure of flow rate.

In one form, a hypopnea will be said to have been detected when a function of respiratory flow rate Qr falls below a second flow rate threshold for a predetermined period of time. The function may determine a peak flow, a relatively short-term mean flow rate, or a flow rate intermediate of relatively short-term mean and peak flow rate, for example an RMS flow rate. The second flow rate threshold may be a relatively long-term measure of flow rate. The second flow rate threshold is greater than the flow rate threshold used to detect apneas.

5.4.3.2.6 Determination of Snore

In one form of the present technology, the central controller 4230 executes one or more snore determination algorithms 4326 for the determination of the extent of snore.

In one form, the snore determination algorithm 4326 receives as an input a respiratory flow rate signal Qr and provides as an output a metric of the extent to which snoring is present.

The snore determination algorithm 4326 may comprise the step of determining the intensity of the flow rate signal in the range of 30-300 Hz. Further, the snore determination algorithm 4326 may comprise a step of filtering the respiratory flow rate signal Qr to reduce background noise, e.g., the sound of airflow in the system from the blower.

5.4.3.2.7 Determination of Airway Patency

In one form of the present technology, the central controller 4230 executes one or more airway patency determination algorithms 4327 for the determination of the extent of airway patency.

In one form, the airway patency determination algorithm 4327 receives as an input a respiratory flow rate signal Qr, and determines the power of the signal in the frequency range of about 0.75 Hz and about 3 Hz. The presence of a peak in this frequency range is taken to indicate an open airway. The absence of a peak is taken to be an indication of a closed airway.

In one form, the frequency range within which the peak is sought is the frequency of a small forced oscillation in the treatment pressure Pt. In one implementation, the forced oscillation is of frequency 2 Hz with amplitude about 1 $cmH_2O$.

In one form, airway patency determination algorithm 4327 receives as an input a respiratory flow rate signal Qr, and determines the presence or absence of a cardiogenic signal. The absence of a cardiogenic signal is taken to be an indication of a closed airway.

5.4.3.2.8 Determination of Target Ventilation

In one form of the present technology, the central controller 4230 takes as input the measure of current ventilation, Vent, and executes one or more target ventilation determination algorithms 4328 for the determination of a target value Vtgt for the measure of ventilation.

In some forms of the present technology, there is no target ventilation determination algorithm 4328, and the target value Vtgt is predetermined, for example by hard-coding during configuration of the RPT device 4000 or by manual entry through the input device 4220.

In other forms of the present technology, such as adaptive servo-ventilation (ASV), the target ventilation determination algorithm 4328 computes a target value Vtgt from a value Vtyp indicative of the typical recent ventilation of the patient.

In some forms of adaptive servo-ventilation, the target ventilation Vtgt is computed as a high proportion of, but less than, the typical recent ventilation Vtyp. The high proportion in such forms may be in the range (80%, 100%), or (85%, 95%), or (87%, 92%).

In other forms of adaptive servo-ventilation, the target ventilation Vtgt is computed as a slightly greater than unity multiple of the typical recent ventilation Vtyp.

The typical recent ventilation Vtyp is the value around which the distribution of the measure of current ventilation Vent over multiple time instants over some predetermined timescale tends to cluster, that is, a measure of the central tendency of the measure of current ventilation over recent history. In one implementation of the target ventilation determination algorithm 4328, the recent history is of the order of several minutes, but in any case should be longer than the timescale of Cheyne-Stokes waxing and waning cycles. The target ventilation determination algorithm 4328 may use any of the variety of well-known measures of central tendency to determine the typical recent ventilation Vtyp from the measure of current ventilation, Vent. One such measure is the output of a low-pass filter on the measure of current ventilation Vent, with time constant equal to one hundred seconds.

5.4.3.2.9 Determination of Therapy Parameters

In some forms of the present technology, the central controller 4230 executes one or more therapy parameter determination algorithms 4329 for the determination of one or more therapy parameters using the values returned by one or more of the other algorithms in the therapy engine module 4320.

In one form of the present technology, the therapy parameter is an instantaneous treatment pressure Pt. In one implementation of this form, the therapy parameter determination algorithm 4329 determines the treatment pressure Pt using the equation $$Pt = A\Pi(\Phi, t) + P_0 \qquad (1)$$

where:
A is the amplitude,
$\Pi(\Phi, t)$ is the waveform template value (in the range 0 to 1) at the current value $\Phi$ of phase and t of time, and
$P_0$ is a base pressure.

If the waveform determination algorithm 4322 provides the waveform template $\Pi(\Phi, t)$ as a lookup table of values Π indexed by phase $\Phi$, the therapy parameter determination algorithm 4329 applies equation (1) by locating the nearest lookup table entry to the current value Φ of phase returned by the phase determination algorithm 4321, or by interpolation between the two entries straddling the current value Φ of phase.

The values of the amplitude A and the base pressure $P_0$ may be set by the therapy parameter determination algorithm 4329 depending on the chosen respiratory pressure therapy mode in the manner described below.

5.4.3.3 Therapy Control Module

The therapy control module 4330 in accordance with one aspect of the present technology receives as inputs the therapy parameters from the therapy parameter determination algorithm 4329 of the therapy engine module 4320, and controls the pressure generator 4140 to deliver a flow of air in accordance with the therapy parameters.

In one form of the present technology, the therapy parameter is a treatment pressure Pt, and the therapy control module 4330 controls the pressure generator 4140 to deliver a flow of air whose mask pressure Pm at the patient interface 3000 is equal to the treatment pressure Pt.

5.4.3.4 Detection of Fault Conditions

In one form of the present technology, the central controller 4230 executes one or more methods 4340 for the detection of fault conditions. The fault conditions detected by the one or more methods 4340 may include at least one of the following:

Power failure (no power, or insufficient power)
Transducer fault detection
Failure to detect the presence of a component
Operating parameters outside recommended ranges (e.g. pressure, flow rate, temperature, $PaO_2$)
Failure of a test alarm to generate a detectable alarm signal.

Upon detection of the fault condition, the corresponding algorithm 4340 signals the presence of the fault by one or more of the following:

Initiation of an audible, visual &/or kinetic (e.g. vibrating) alarm
Sending a message to an external device
Logging of the incident

5.5 Air Circuit

An air circuit 4170 in accordance with an aspect of the present technology is a conduit or a tube constructed and arranged to allow, in use, a flow of air to travel between two components such as RPT device 4000 and the patient interface 3000.

In particular, the air circuit 4170 may be in fluid connection with the outlet of the pneumatic block 4020 and the patient interface. The air circuit may be referred to as an air delivery tube. In some cases there may be separate limbs of the circuit for inhalation and exhalation. In other cases a single limb is used.

In some forms, the air circuit 4170 may comprise one or more heating elements configured to heat air in the air circuit, for example to maintain or raise the temperature of the air. The heating element may be in a form of a heated wire circuit, and may comprise one or more transducers, such as temperature sensors. In one form, the heated wire circuit may be helically wound around the axis of the air circuit 4170. The heating element may be in communication with a controller such as a central controller 4230. One example of an air circuit 4170 comprising a heated wire circuit is described in U.S. Pat. No. 8,733,349, which is incorporated herewithin in its entirety by reference.

5.5.1 Oxygen Delivery

In one form of the present technology, supplemental oxygen 4180 is delivered to one or more points in the pneumatic path, such as upstream of the pneumatic block 4020, to the air circuit 4170 and/or to the patient interface 3000.

5.6 Humidifier

5.6.1 Humidifier Overview

In one form of the present technology there is provided a humidifier 5000 to change the absolute humidity of air or gas for delivery to a patient relative to ambient air. Typically, the humidifier 5000 is used to increase the absolute humidity and increase the temperature of the flow of air (relative to ambient air) before delivery to the patient's airways.

A simplified representation of a humidifier 5000 is shown in FIG. 5A. In one form, a humidifier 5000 may comprise a humidifier reservoir 5110, a heating element 5240 and one or more sensors 5210. The humidifier 5000 may be configured to receive a flow of air from a pressure generator 4140 via an air circuit 4170, and deliver a flow of humidified air to a patient interface 3000 (not shown in FIG. 5A), for example via a heated air circuit 4171.

A simplified schematic of a humidifier 5000 according to an example of the present technology is shown in FIG. 5B. The humidifier 5000 may comprise one or more controllers 5250 such as a heated air circuit controller 5254, a heating element controller 5252 or a central humidifier controller 5251, which may be discrete controllers or one controller performing multiple functions. The controller(s) 5250 may be in electrical communication with one or more of: one or more sensors 5210, input devices 4220, output devices 4290, heated air circuit 4171 and a heating element 5240 as shown in FIG. 5B.

FIGS. 7 to 33 illustrates a humidifier 6000 according to an example of the present technology. As illustrated, the humidifier 6000 includes a reservoir dock 6100 structured and arranged to receive a water reservoir 6500. In the illustrated example, the humidifier 6000 is integrated with an RPT device 7000 such that an external housing 7010 of the RPT device 7000 encases components that perform the function of the RPT device 7000 as well as components that perform the function of the humidifier 6000. For example, as shown in FIGS. 7 to 17, the reservoir dock 6100 is integrated with the external housing 7010 to provide an integral unit, with the reservoir dock 6100 structured and arranged to receive the water reservoir 6500.

It should be appreciated that the humidifier 6000 (e.g., reservoir dock 6100) may be provided separately to the RPT device 7000 in an alternative arrangement. In such arrangement, additional interfaces may be used to connect the humidifier 6000 (e.g., reservoir dock 6100) to the RPT device 7000.

The RPT device 7000 comprises a blower 7100 supported within the external housing 7010, e.g., see FIGS. 10 and 11. The blower 7100 is structured and arranged for producing a flow, or a supply, of air at positive pressure, e.g., in the range of 4-30 $cmH_2O$. In an example, the blower 7100 may include a single stage design or a multi-stage design, e.g., two or more stage designs. The blower 7100 is operable to draw a supply of air into the external housing 7010, e.g., through one or more intake openings in the external housing 7010, and into an inlet thereof (blower inlet) 7105, and provide a pressurized supply of air at an outlet (blower outlet) 7110. Examples and details of an exemplary blower are described in PCT Patent Application Publication No. WO 2013/020167, which is incorporated herein by reference in its entirety. The blower outlet 7110 is communicated with the humidifier 6000 as described in greater detail below.

5.6.2 Humidifier Components

5.6.2.1 Water Reservoir

FIGS. 18 to 29 show a water reservoir 6500 according to an example of the present technology. The water reservoir 6500 is configured to hold, or retain, a volume of liquid (e.g., water) to be evaporated for humidification of the flow of air. The water reservoir 6500 may be configured to hold a predetermined maximum volume of water in order to provide adequate humidification for at least the duration of a respiratory therapy session, such as one evening of sleep. Typically, the water reservoir 6500 is configured to hold several hundred millilitres of water, e.g. 300 millilitres (ml), 325 ml, 350 ml or 400 ml, although it is to be understood that other volumes of liquid may be utilised, e.g., at least 100 ml. In other forms, the humidifier 6000 may be configured to receive a supply of water from an external water source such as a building's water supply system.

In the illustrated example, the water reservoir 6500 includes a reservoir base 6600 (also referred to as a humidifier tub) and a reservoir lid 6700 (also referred to as a humidifier tub lid) removably coupled to the reservoir base 6600. A deformable seal 6750 is provided to the reservoir lid 6700. When the reservoir lid 6700 is coupled to the reservoir base 6600, the seal 6750 is structured and arranged to engage between the lid 6700 and the base 6600 to seal the lid 6700 and the base 6600 and prevent egress of water from the water reservoir 6500. The reservoir lid 6700 is structured to be fully removable from the reservoir base 6600, e.g., for patient usability to clean the interior of the reservoir base 6600 and/or the reservoir lid 6700. In an alternative example, the seal 6750 may be provided to the reservoir base 6600.

In an example, the reservoir base 6600 and the reservoir lid 6700 may comprise a bio-compatible material, e.g., such as plastic or thermoplastic polymer.

In an alternative example, the reservoir lid 6700 may not be removable from the reservoir base 6600. In such example, the water reservoir 6500 with the integrated/non-removable lid 6700 may be disposable. An exemplary benefit of such example is that a new water reservoir may be obtained, e.g., each use, and the patient can be assured that it is clean rather than the variability of not knowing whether the water reservoir has been sufficiently cleaned.

According to one aspect, the water reservoir 6500 is configured to add humidity to a flow of air from the RPT device 7000 as the flow of air travels therethrough. In one form, the water reservoir 6500 may be configured to encourage the flow of air to travel in a tortuous path through the reservoir 6500 while in contact with the volume of water therein. For example, the water reservoir 6500 may comprise one or more flow elements, e.g., baffles, to encourage a tortuous flow path.

As described in more detail below, the water reservoir 6500 may be removably coupled with the reservoir dock 6100, for example in a lateral direction as shown in FIG. 15.

As described in more detail below, the water reservoir 6500 may also be configured to discourage egress of liquid therefrom, such as when the reservoir 6500 is displaced and/or rotated from its normal, working orientation, such as through any apertures and/or in between its sub-components. As the flow of air to be humidified by the humidifier 6000 is typically pressurised, the reservoir 6500 may also be configured to prevent losses in pneumatic pressure through leak and/or flow impedance.

Reservoir Base

In FIG. 21, the reservoir base 6600 comprises a plurality of walls and a conductive portion 6650 sealed to a bottom one of the walls to form a chamber or cavity 6660 to hold the volume of water.

The conductive portion 6650 is configured to allow efficient transfer of heat from a heating element (e.g., heater plate 6250 of the reservoir dock 6100) to the volume of liquid in the reservoir 6500. In one form, the conductive portion 6650 may be arranged as a plate, although other shapes may also be suitable. All or a part of the conductive portion 6650 may be made of a thermally conductive material such as aluminium (e.g., approximately 2 mm thick, such as 1 mm, 1.5 mm, 2.5 mm or 3 mm), another heat conducting metal or some plastics. In some cases, suitable heat conductivity may be achieved with less conductive materials of suitable geometry.

In FIG. 23, the reservoir base 6600 includes an opening 6665 (e.g., along an upper, front corner portion) into the chamber 6660 structured and arranged to receive the reservoir lid 6700. A rim 6670 is provided along the perimeter of the opening 6665. As illustrated, the rim 6670 is spaced inwardly from the edge of the opening 6665 and extends inwardly towards the interior of the chamber 6660. The rim 6670 and adjacent wall portion 6675 along the perimeter of the opening 6665 provide surfaces arranged to engage or interface with the seal 6750 provided to the reservoir lid 6700, e.g., to prevent egress of water from the water reservoir 6500. In addition, such engagement of the seal 6750 with the rim 6670 and adjacent wall portion 6675 may be arranged to help retain the reservoir lid 6700 to the reservoir base 6600. Further, the reservoir lid 6700 may include wing portions 6770 with respective locking tabs 6775 (see FIG. 25) arranged to engage behind the rim 6670 of the reservoir base 6660 (e.g., with a snap-fit) to releasably retain the reservoir lid 6700 to the reservoir base 6600.

In FIG. 21, in an example, the reservoir base 6600 may comprise a first part or base mold 6600A constructed of a relatively rigid material and a second part or overmold 6600B constructed of a relatively soft material (e.g., thermoplastic elastomer (TPE) or silicone) provided (e.g., by overmolding) to the first part 6600A. In the illustrated example, the overmold 6600B is provided to an exterior surface of the base mold 6600A along a rear portion thereof, e.g., opposite to the opening 6665 provided along a front portion. The overmold 6600B extends along the perimeter of the reservoir base 6600 to provide grip or tactility to the water reservoir 6500, e.g., to facilitate manual engagement/disengagement of the water reservoir 6500 with the reservoir dock 6100.

In FIG. 23, in addition, an annular wall 6680 extends from the exterior surface of the reservoir base 6600 adjacent a front edge of the overmold 6600B. In one form, the annular wall 6680 and front edge of the overmold 6600B may provide a stop, e.g., to ensure that the water reservoir 6500 is fully engaged within the reservoir dock 6100 in use.

Reservoir Lid

In FIG. 21, the reservoir lid 6700 includes a lid portion 6710 and an elongated, hollow body or single conduit 6720 provided to the lid portion 6710. The seal 6750 is spaced inwardly from the edge of the lid portion 6710. The edge of the lid portion 6710 may provide a stop structured and arranged to engage along the edge of the base opening 6665 as the seal 6750 engages with the rim 6670 and adjacent wall portion 6675 of the base 6600.

In the illustrated example, the reservoir lid 6700 includes only a single conduit 6720 that provides both an inlet for receiving a flow of air into the water reservoir 6500 and an outlet for delivering a flow of air from the reservoir 6500. In addition, the single conduit 6720 provides a single inlet for filling the water reservoir 6500 with water, which improves usability, e.g., because there is no mistake or confusion which conduit is usable for filling the water reservoir with water if more than one conduit was present.

Moreover, such single conduit arrangement of the water reservoir 6500 prevents alternative water reservoirs from being used or connected with the reservoir dock 6100 of the present technology, e.g., water reservoirs known in the art include two conduits (i.e., separate inlet and outlet conduits) which would not be compatible with the reservoir dock 6100 of the present technology.

As illustrated, the single conduit 6720 includes an outer end portion 6730 and an inner end portion 6740. When the reservoir lid 6700 is coupled to the reservoir base 6600, the outer end portion 6730 is arranged outside the chamber 6660 and the inner end portion 6740 is arranged inside the chamber 6660. As such, the outer end portion 6730 provides an outer opening 6735 arranged outside the chamber 6660, and the inner end portion 6740 provides an inner opening 6745 arranged inside the chamber 6660.

The outer opening 6735 is arranged at one end of the single conduit 6720 such that an axis through the geometric center of the outer opening 6735 is aligned with the longitudinal axis of the conduit 6720. The inner opening 6745 is arranged along a bottom wall of conduit 6720 such an axis through the geometric center of the inner opening 6745 is generally transverse or perpendicular to the axis of the outer opening 6735 and the longitudinal axis of the conduit 6720. As such, the inner opening 6745 is arranged to be oriented downwardly towards the bottom wall and conductive portion 6650 of the reservoir base 6600.

As noted above, the conduit 6720 provides a single inlet for filling the water reservoir 6500 with water. In the illustrated example, the inner opening 6745 opens into the interior of the chamber 6660 of the water reservoir 6500, and the shape of the inner opening 6745, e.g., squarish with rounded corners, maximizes the opening size, e.g., to facilitate filling.

Moreover, the longitudinal length of the inner end portion 6740 of the conduit 6720 and/or the positioning of the inner opening 6745 along the inner end portion 6740 of the conduit 6720 are suitably selected so as to arrange the inner opening 6745 at or near the geometric center or centroid of the reservoir chamber 6660, e.g., within at least about 6-11 mm of the geometric center or centroid of the reservoir chamber 6660. Such arrangement provides optimal spillback performance as described in greater detail below.

A seal 6760 is provided to the free end of the outer end portion 6730 of the conduit 6720. When the water reservoir 6500 is coupled to the reservoir dock 6100, the seal 6760 is structured and arranged to provide a face seal with the reservoir dock 6100, e.g., to prevent losses in pneumatic pressure through leak.

In the illustrated example, the conduit 6720 includes a non-circular cross-sectional shape, e.g., squarish with rounded corners. However, it should be appreciated that the conduit may include other cross-sectional shapes, e.g., circular shape (e.g., cylindrical or tubular conduit) or noncircular shape (e.g., square, rectangle).

5.6.2.2 Reservoir Dock

In the illustrated example, the reservoir dock 6100 is provided to the external housing 7010 of the RPT device 7000 and configured and arranged to receive the water reservoir 6500, e.g., see FIGS. 30 to 33.

In FIGS. 10 and 33, the reservoir dock 6100 includes a main body 6200 forming a cavity 6210 to receive the water reservoir 6500, a dock inlet conduit 6300 arranged to receive a pressurized flow of air from the RPT device 7000 and deliver such pressurized flow of air to the water reservoir 6500, and a dock outlet conduit 6400 arranged to receive the pressurized flow of air that has been humidified in the water reservoir 6500 and deliver such humidified air to the air circuit 4170.

In an example, the reservoir dock may comprise a biocompatible material, e.g., such as plastic or thermoplastic polymer.

The main body 6200 comprises a plurality of walls and a heating element (e.g., heater plate 6250) provided to a bottom one of the walls to form the cavity 6210 to receive the water reservoir 6500.

The external housing 7010 of the RPT device 7000 includes an open end and the main body 6200 of the reservoir dock 6100 is arranged within the external housing 7010 adjacent the open end such that the open end of the cavity 6210 is arranged to receive the water reservoir 6500.

The dock inlet conduit 6300 includes an outer end portion 6310 arranged outside the cavity 6210 and an inner end portion 6320 arranged inside the cavity 6210. As such, the outer end portion 6310 provides an outer opening 6315 arranged outside the cavity 6210, and the inner end portion 6320 provides an inner opening 6325 arranged inside the cavity 6210.

The outer opening 6315 is arranged at one end of the dock inlet conduit 6300 such that an axis a1 through the geometric center of the outer opening 6315 is aligned with the longitudinal axis of the dock inlet conduit 6300 (e.g., see FIG. 11). The inner opening 6325 is arranged along a bottom wall of dock inlet conduit 6300 such that an axis a2 through the geometric center of the inner opening 6325 is generally transverse or perpendicular to the axis a1 of the outer opening 6315 and the longitudinal axis of the dock inlet conduit 6300. As such, the inner opening 6325 is oriented downwardly towards the bottom wall and heater plate 6250 of the reservoir dock 6100.

In the illustrated example, the outer end portion 6310 of the dock inlet conduit 6300 includes a circular cross-sectional shape (e.g., cylindrical or tubular conduit), e.g., to facilitate connection to the blower 7100 of the RPT device 7000. In the illustrated example, the inner end portion 6320 of the dock inlet conduit 6300 includes a non-circular cross-sectional shape, e.g., squarish with rounded corners. However, it should be appreciated that the dock inlet conduit 6300 may include other cross-sectional shapes, e.g., circular and noncircular shapes, and the outer and inner end portions 6310, 6320 may have similar or different cross-sectional shapes relative to one another.

Moreover, at least the inner end portion 6320 of the dock inlet conduit 6300 is suitably sized to allow the inner end portion 6320 to extend into the interior of the conduit 6720 of the reservoir lid 6700 when the water reservoir 6500 is inserted into the reservoir dock 6100, i.e., single conduit 6720 and dock inlet conduit 6300 are suitably sized so that the single conduit 6720 can receive and overlap the dock inlet conduit 6300 therewithin.

Further, the longitudinal length of the inner end portion 6320 of the dock inlet conduit 6300 and/or the positioning of the inner opening 6325 along the inner end portion 6320 of the dock inlet conduit 6300 are suitably selected so as to arrange the inner opening 6325 at or near the inner opening 6745 of the single conduit 6720, when the water reservoir 6500 is inserted into the reservoir dock 6100. For example, the inner opening 6325 of the dock inlet conduit 6300 is arranged to at least partially overlap with the inner opening 6745 of the single conduit 6720. In an example, the geometric centers of the inner openings 6325, 6745 may be aligned or coaxial with one another. As such, the inner opening 6325 of the dock inlet conduit 6300 may be arranged at or near the geometric center or centroid of the water reservoir chamber 6660.

Such overlapping or nested arrangement of the single conduit 6720 and dock inlet conduit 6300 forms inlet and outlet flow paths or passageways into and out of the water reservoir 6500. For example, as best shown in FIGS. 10 to 14, 16, and 17, the inlet flow path is formed by the interior surface of the dock inlet conduit 6300, and the outlet flow path is formed between the interior surface of the single conduit 6720 and the exterior surface of the dock inlet conduit 6300.

As such, the inner opening 6325 of the dock inlet conduit 6300 forms an inlet for air flow into the chamber 6660 of the water reservoir 6500. Also, the end of the dock inlet conduit 6300 and the end of the single conduit 6720 cooperate to form an outlet for air flow out of the chamber 6660 of the water reservoir 6500. Moreover, such overlapping or nested arrangement of the single conduit 6720 and dock inlet conduit 6300 positions the inlet and the outlet of air flow into and out of the water reservoir 6500 at or near the geometric center or centroid of the reservoir chamber, e.g., within at least about 6-11 mm of the geometric center or centroid of the reservoir chamber.

In addition, the openings 6325, 6745 are oriented downwardly towards the heater plate 6250/conductive portion 6650 such that both openings 6325, 6745 face the water in the water reservoir 6500, e.g., to facilitate humidification by directing air flow towards the surface of the water.

The dock outlet conduit 6400 includes an outer end portion 6410 arranged outside the cavity 6210 and an inner end portion 6420 arranged inside the cavity 6210. In the illustrated example, the outer end portion 6410 of the dock outlet conduit 6400 includes a circular cross-sectional shape (e.g., cylindrical or tubular conduit), e.g., to facilitate connection to the air circuit 4170. In the illustrated example, the inner end portion 6420 of the dock outlet conduit 6400 also includes a circular cross-sectional shape (e.g., cylindrical or tubular conduit). However, it should be appreciated that the dock outlet conduit 6400 may include other cross-sectional shapes along its length, e.g., circular and noncircular shapes.

In the illustrated example, a conduit portion 6450 is provided inside the cavity 6210 and arranged to overlap a portion of the inner end portion 6320 of the dock inlet conduit 6300. As illustrated, the conduit portion 6450 is arranged to extend from a rear wall of the main body 6200 and overlap a portion of the inner end portion 6320 adjacent the rear wall. The free end of the conduit portion 6450 includes an outwardly extending flange or lip 6455.

In an example, the conduit portion 6450 includes a cross-section similar in shape and size to the single conduit 6720 of the water reservoir 6500, e.g., a non-circular cross-sectional shape, e.g., squarish with rounded corners. However, it should be appreciated that the conduit 6720 may include other cross-sectional shapes, e.g., circular or non-circular shapes.

As best shown in FIGS. 10 and 11, the inner end portion 6420 of the dock outlet conduit 6400 extends from a side wall of the conduit portion 6450. In the illustrated example, the dock outlet conduit 6400 is arranged generally transverse or perpendicular to the conduit portion 6450, e.g., the longitudinal axis of the dock outlet conduit 6400 is generally perpendicular to the longitudinal axis of the conduit portion 6450. However, it should be appreciated that the dock outlet conduit 6400 and conduit portion 6450 may be arranged in alternative configurations, e.g., arranged at non-perpendicular angle relative to one another.

When the water reservoir 6500 is inserted into the reservoir dock 6100, the seal 6760 along the outer end portion 6730 of the single conduit 6720 is structured to sealingly engage or interface against the flange or lip 6455 along the free end of the conduit portion 6450. Such engagement provides a face seal between the water reservoir 6500 and the reservoir dock 6100, e.g., to prevent losses in pneumatic pressure through leak. That is, such engagement seals the outlet flow path that allows air flow out of the chamber 6660 of the water reservoir 6500 to pass back through the single conduit 6720, into the conduit portion 6450, and out the dock outlet conduit 6400. In the illustrated example, the outer end portion 6410 of the dock outlet conduit 6400 is arranged to protrude outside the external housing 7010 of the RPT device 7000 to allow connection to the air circuit 4170.

In some arrangements, the reservoir dock 6100 may comprise a locking feature configured to releasably retain the water reservoir 6500 in the reservoir dock 6100. In an example, the external housing 7010 of the RPT device 7000 may comprise a locking feature configured to releasably retain the water reservoir 6500 in the reservoir dock 6100. For example, as shown in FIGS. 7 and 8, the external housing 7010 of the RPT device 7000 may comprise a release button 7200, e.g., along a top wall of the external housing 7010, structured and arranged to releasably retain the water reservoir 6500 in the reservoir dock 6100. The release button 7200 may include a retainer structured and arranged to releasably retain the water reservoir 6500 when the water reservoir 6500 is inserted into the reservoir dock 6100. The retainer may be structured and arranged to allow release or removal of the water reservoir 6500 from the reservoir dock 6100 upon manual depression of the release button 7200. As shown in FIGS. 18 and 21, the top wall of the water reservoir 6500 may comprise a retaining feature, e.g., protrusion 6510, structured and arranged to releasably engage the retainer of the release button 7200. However, it should be appreciated that the water reservoir 6500 may be releasably retained in the reservoir dock 6100 in other suitable manners.

In an alternative example, the mating relationship of the inner end portion 6320 of the dock inlet conduit 6300 and the conduit 6720 of the reservoir lid 6700 may be reversed. For example, the inner end portion 6320 of the dock inlet conduit 6300 and the conduit 6720 may be structured and arranged to allow the inner end portion 6320 to receive the conduit 6720 within its interior when the water reservoir 6500 is inserted into the reservoir dock 6100, i.e., the inner end portion 6320 of the dock inlet conduit 6300 is structured and arranged to receive and overlap the conduit 6720 therewithin.

5.6.2.3 Water Reservoir to Reservoir Dock Connection

In use, the water reservoir 6500 is removably coupled with the reservoir dock 6100 by inserting the water reservoir 6500 into the reservoir dock 6100, e.g., by sliding the water reservoir 6500 in a lateral direction into the cavity 6210 of the reservoir dock 6100. The single conduit 6720 and the dock inlet conduit 6300 are generally horizontally oriented and generally aligned with an axis of assembly (e.g., axis a in FIG. 15) such that the dock inlet conduit 6300 extends into the single conduit 6720 to establish the overlapping and nested arrangement when the water reservoir 6500 is removably coupled with the reservoir dock 6100. The seal 6760 provided to the single conduit 6720 sealingly engages the conduit portion 6450 of the reservoir dock 6100 when the water reservoir 6500 reaches an operative position within the reservoir dock 6100, which provides a pneumatic seal. In addition, engagement of the seal 6760 may provide a stop to provide an indication that the water reservoir 6500 has reached the operative position.

Moreover, when the water reservoir 6500 reaches the operative position, the conductive portion 6650 of the water reservoir 6500 aligns with and thermally contacts the heater plate 6250 of the reservoir dock 6100 to allow heat transfer from the heater plate 6250 to the water in the water reservoir 6500, e.g., surface of the conductive portion 6650 engages or contacts surface of the heater plate 6250 (e.g., see FIG. 11). A level or degree of thermal contact between the conductive portion 6650 and the heater plate 6250 may be varied, e.g., spring elements provided to heater plate 6250 to increase contact pressure and improve thermal contact.

The dock inlet conduit 6300 is configured to receive the pressurized flow of air from the blower 7100 of the RPT device 7000, and to direct the flow of air into the water reservoir 6500 via the inner opening 6325 of the dock inlet conduit 6300. Humidity (i.e., water vapour) is added to the flow of air as the air travels through the water reservoir 6500, and the humidified flow of air exits the water reservoir 6500 through the outlet formed between the end of the dock inlet conduit 6300 and the end of the single conduit 6720. Air continues to flow along the outlet flow path between dock inlet conduit 6300 and the single conduit 6720, into the conduit portion 6450, and out the dock outlet conduit 6400. The dock outlet conduit 6400 is connectable to the air circuit 4170 to deliver the flow of humidified air to the patient. FIGS. 16 and 17 show exemplary inlet and outlet flow paths of the flow of air through the reservoir dock 6100 and the water reservoir 6500.

The overmold 6600B provided to the rear portion of the water reservoir 6500 is structured and arranged to assist the patient to grip and hold the water reservoir 6500 during engagement/disengagement with the reservoir dock 6100.

In FIG. 18, also, the front portion of the water reservoir 6500 provides a recessed, dock engagement portion 6505 structured and arranged to interface and engage the reservoir dock 6100. In an example, the water reservoir 6500 and reservoir dock 6100 may include structure to facilitate placement and alignment of the water reservoir 6500 with the reservoir dock 6100. For example, opposing sides of the water reservoir 6500 along the dock engagement portion 6505 may include guiding surfaces (e.g., rails 6520) arranged to engage corresponding guiding surfaces (e.g., recesses 6530) within the reservoir dock 6100 to guide the water reservoir 6500 into the reservoir dock 6100. However, it should be appreciated that other guiding structures are possible.

In the illustrated example, the water reservoir 6500 may be removed from the reservoir dock 6100 while the air circuit 4170 remains attached to the dock outlet conduit 6400. Thus, the insertion and removal of the water reservoir 6500 may be independent of the connection of the air circuit 4170. Also, the water reservoir 6500 must be removed from the reservoir dock 6100 to fill the water reservoir 6500 with water, thereby reducing the likelihood of the patient over-filling the water reservoir 6500 beyond the given, maximum volume of liquid as the water reservoir 6500 incorporates features to prevent over-filling as described further below.

5.6.2.4 Spillback Protection

The single conduit 6720 of the water reservoir 6500 is structured and arranged to prevent egress of water from the water reservoir 6500 when the water reservoir 6500 is displaced or rotated from its normal, working orientation. In the illustrated example, the single conduit 6720 provides a single opening into the reservoir chamber 6660 which is arranged at or near the geometric center or centroid of the reservoir chamber 6660, e.g., within at least about 6-11 mm of the geometric center or centroid of the reservoir chamber 6660. Such arrangement achieves spillback protection, so that when the water reservoir 6500 is rotated by 90 degrees to 180 degrees in any direction from its working horizontal orientation, the given maximum volume of water is able to be stored in the water reservoir 6500 without reaching the outer opening 6735 of the single conduit 6720 (e.g., see FIGS. 28 and 29). Such spillback protection prevents water from exiting the water reservoir 6500 via the single conduit 6720, e.g., to prevent moisture damage to electronics in the RPT device 7000 when the water reservoir 6500 is received in the reservoir dock 6100 integrated with the RPT device 7000.

5.6.2.5 Overfill Prevention

The single conduit 6720 of the water reservoir 6500 is also structured and arranged to prevent overfilling of the water reservoir 6500, e.g., with a volume of water over and above a predetermined maximum volume of water, which may reduce effectiveness of the spillback prevent feature discussed above.

In the illustrated example, the single conduit 6720 is structured and arranged to form an air lock to prevent further ingress of liquid into the water reservoir 6500 when the predetermined maximum volume of liquid is in the water reservoir 6500. In this form, when filling the water reservoir 6500 via the conduit 6720, an air lock would form an enclosure of air in the water reservoir 6500 that is not displaced by the volume of liquid in the water reservoir 6500. As shown in FIGS. 28 and 29, the water reservoir 6500 is in an orientation such that the longitudinal axis of the conduit 6720 is oriented vertically, as a patient would orient the water reservoir 6500 while filling it with water from a tap or faucet. The water level would rise, and reach the level shown on FIGS. 28 and 29 in which the water level extends just above the top of the inner opening 6745, whereupon the remaining volume of air in the water reservoir 6500 is no longer able to access the conduit 6720. Therefore, air would no longer be able to escape the water reservoir 6500 via the conduit 6720, and the water reservoir 6500 would thus not be able to receive any further volume of water into its chamber 6660. Adding further water would fill the conduit 6720 and then overflow out of the top or outer opening 6735 of the conduit 6720. This would indicate to the patient that the water reservoir 6500 was being overfilled.

The location of the inner opening 6745 of the conduit 6720 at or near the geometric center or centroid of the reservoir chamber 6660 allows a higher water level capacity in the water reservoir 6500.

5.6.2.6 Baffle Plate

In an alternative example, as shown in FIGS. 34 to 40, a baffle plate 6800 may be provided to the water reservoir 6500 to improve humidification performance. In use, the baffle plate 6800 is arranged between the inlet flow path (formed by dock inlet conduit 6300) and the outlet flow path (formed between dock inlet conduit 6300 and the conduit 6720) to encourage the incoming air to flow into contact with the water surface prior to exiting through the outlet formed between the dock inlet conduit 6300 and the single conduit 6720. That is, the baffle plate 6800 is arranged to force air to travel over the water surface to enhance moisture pickup by the flow of air passing through the water reservoir 6500. The baffle plate 6800 also helps reduce/prevent spitting in the configuration illustrated in FIGS. 38 and 39 where the inlet is disposed near the water surface and air is gushing downwards to the surface of the water. The baffle plate 6800 in this case helps prevent droplets of water being pushed into the outlet and down the air circuit 4170. This allows spitting to be mitigated within a smaller overall configuration, thus enhancing the compactness of the device, e.g., as compared to an alternative configuration where spitting is mitigated by disposing the air inlet much higher than the maximum waterline.

In the illustrated example, the baffle plate 6800 is provided to, or otherwise supported by, the reservoir lid 6700. For example, the baffle plate 6800 may be provided to, or otherwise supported by, the conduit 6720 of the reservoir lid 6700. In an example, the baffle plate 6800 may be formed in one-piece with the conduit 6720 (e.g., integrally molded as one-piece construction) to provide an integral unit, e.g., baffle plate 6800 is an extension of a bottom wall of the conduit 6720. Alternatively, the baffle plate 6800 may be formed separately from the conduit 6720 and then permanently or releasably attached thereto, e.g., press fit, snap fit, mechanically fastened, welding or bonding techniques. In an example, the baffle plate 6800 may form a retro-fit component structured for attachment to an existing water reservoir. However, it should be appreciated that the baffle plate may be arranged and supported within the water reservoir in other suitable manners, e.g., supported by side walls of the lid portion 6710, supported within the reservoir base 6600, etc.

FIGS. 36 and 37 show two mutually orthogonal cross-sections of the water reservoir 6500 when the reservoir lid 6700 is coupled to the reservoir base 6600. As illustrated, the baffle plate 6800 in this case forms an extension of the bottom wall of the conduit 6720 and includes an inlet opening 6810 arranged to communicate with the dock inlet conduit 6300 in use. Edges of the baffle plate 6800 are spaced from side walls forming the interior of the water reservoir 6500, which provides a gap 6815 to allow air to escape around the edges to the air flow outlet.

The baffle plate 6800 includes a length that extends parallel to a longitudinal axis of the conduit 6720 and a width that extends perpendicular to the length. As best shown in FIGS. 34 and 37, the shown baffle plate 6800 includes a slight curvature along its width so as to curve downwardly from the conduit 6720 towards the base 6600 or water in the water reservoir 6500 in use. Such curved arrangement allows water runoff from the upper surface 6820 of the baffle plate 6800 to avoid water accumulation. However, it should be appreciated that the baffle plate may include a curvature along its length and may include other suitable configurations along its length and/or width, e.g., generally planar configuration or other suitable curvatures along the width and/or length.

In the illustrated example, the baffle plate 6800 includes a generally constant thickness. However, it should be appreciated that the thickness of the baffle plate may vary, e.g., thickness may increase and/or decrease along its length and/or width.

FIGS. 38 and 39 show examples of the water reservoir 6500 including baffle plate 6800 when coupled with reservoir dock 6100 in use. As illustrated, the dock inlet conduit 6300 of the reservoir dock 3100 extends into the single conduit 6720 to establish the overlapping and nested arrangement as described above. When the water reservoir 6500 reaches the operative position, the inner opening 6325 of the dock inlet conduit 6300 is generally aligned or coaxial with the inlet opening 6810 of the baffle plate 6800 (see FIG. 38). As such, the inlet for air flow into the chamber 6660 of the water reservoir 6500 may be arranged at or near the geometric center or centroid of the water reservoir chamber 6660. Also, the end of the dock inlet conduit 6300 and the end of the single conduit 6720 cooperate to form an outlet for air flow out of the chamber 6660 of the water reservoir 6500.

FIGS. 38 and 39 also show exemplary inlet and outlet flow paths of the flow of air through the water reservoir 6500. FIG. 40 also shows an exemplary flow path around the baffle plate 6800 to the outlet of the water reservoir. As illustrated, the pressurized flow of air is directed into the water reservoir 6500 via the dock inlet conduit 6300 and passes through aligned openings 6325, 6810 towards the surface of the water. The baffle plate 6800 forces air to travel over the water surface before exiting via gap 6815 along the edges of the baffle plate 6800 towards the air flow outlet, thereby allowing increased moisturization of the flow of gas. Humidity (i.e., water vapour) is added to the flow of air as the air travels through the water reservoir 6500, and the humidified flow of air exits the water reservoir 6500 through the outlet formed between the end of the dock inlet conduit 6300 and the end of the single conduit 6720. Air continues to flow along the outlet flow path between dock inlet conduit 6300 and the single conduit 6720 towards the dock outlet conduit 6400 as described above.

Such baffle plate arrangement also prevents short-circuiting of the air flow from the inlet air flow to the outlet air flow, i.e., configuration and positioning of the baffle plate 6800 provides a barrier between the inlet and outlet air flow to encourage contact of the air with the water surface before exiting the outlet.

When seen in a cross-section as shown in FIG. 39, the dock inlet conduit 6300 forms an inlet cross-sectional area ($A_{inlet}$) for the inlet flow path; and the dock inlet conduit 6300 and the single conduit 6720 cooperate to form an outlet cross-sectional area ($A_{outlet}$) for the outlet flow path. For an improved flow dynamic performance, the hydraulic resistance of the inlet flow path should be substantially equal or at least similar to that of the outlet flow path. One way to ensure this for similarly shaped inlet and outlet, is for the inlet and the outlet flow paths to have at least similar cross-sectional areas, as well as generally similar lengths and similar overall spatial configurations. In the case of different cross-sectional shapes, instead of similar cross-sectional areas, the inlet and outlet flow paths should have similar hydraulic diameters, as well as generally similar lengths and similar overall spatial configurations.

In addition, as best shown in FIG. 39, the dock inlet conduit 6300 and the single conduit 6720 are generally horizontally oriented and generally aligned with one another, i.e., longitudinal axis through the geometric centers of the dock inlet conduit 6300 and the single conduit 6720 are aligned or coaxial with one another. However, it should be appreciated that the dock inlet conduit 6300 and the single conduit 6720 may include longitudinal axes that are offset from one another.

Further, as shown in FIG. 39, the dock inlet conduit 6300 includes a cross-section similar in shape to the single conduit 6720 of the water reservoir 6500, e.g., a non-circular cross-sectional shape, e.g., generally rectangular. However, it should be appreciated that the dock inlet conduit 6300 and the single conduit 6720 may include other cross-sectional shapes, e.g., circular and noncircular shapes, and the dock inlet conduit 6300 and the single conduit 6720 may have similar or different cross-sectional shapes relative to one another.

5.6.2.7 Water Level Indicator

The water reservoir 6500 may comprise a water level indicator, e.g., one or more lines or markings along the reservoir base 6600. In some forms, the water level indicator may provide one or more indications to a user such as the patient 1000 or a care giver regarding a quantity of the volume of water in the water reservoir 6500. The one or more indications provided by the water level indicator may include an indication of a maximum, predetermined volume of water, any portions thereof, such as 25%, 50% or 75% or volumes such as 200 ml, 300 ml or 400 ml.

5.6.2.8 Humidifier Transducer(s)

The humidifier may comprise one or more humidifier transducers (sensors) 5210 instead of, or in addition to, transducers 4270 described above. Humidifier transducers 5210 may include one or more of an air pressure sensor 5212, an air flow rate transducer 5214, a temperature sensor 5216, or a humidity sensor 5218 as shown in FIG. 5B. A humidifier transducer 5210 may produce one or more output signals which may be communicated to a controller such as the central controller 4230 and/or the humidifier controller 5250. In some forms, a humidifier transducer may be located externally to the humidifier (such as in the air circuit 4170) while communicating the output signal to the controller.

5.6.2.8.1 Pressure Transducer

One or more pressure transducers 5212 may be provided to the humidifier in addition to, or instead of, a pressure sensor 4272 provided in the RPT device.

5.6.2.8.2 Flow Rate Transducer

One or more flow rate transducers 5214 may be provided to the humidifier in addition to, or instead of, a flow rate sensor 4274 provided in the RPT device.

5.6.2.8.3 Temperature Transducer

The humidifier may comprise one or more temperature transducers 5216. The one or more temperature transducers 5216 may be configured to measure one or more temperatures such as of the heating element 5240 and/or of the flow of air downstream of the humidifier outlet 5004. In some forms, the humidifier may further comprise a temperature sensor 5216 to detect the temperature of the ambient air.

5.6.2.8.4 Humidity Transducer

In one form, the humidifier may comprise one or more humidity sensors 5218 to detect a humidity of a gas, such as the ambient air. The humidity sensor 5218 may be placed towards the humidifier outlet 5004 in some forms to measure a humidity of the gas delivered from the humidifier. The humidity sensor may be an absolute humidity sensor or a relative humidity sensor.

5.6.2.9 Heating Element

A heater plate 6250 is used to transfer heat to the water reservoir 6500. In the illustrated example, the heater plate 6250 may form a part of the reservoir dock 6100, and may be located on or near the base of the reservoir dock 6100. The heater plate 6250 may be formed, for example, of a nickel chrome alloy, stainless steel or anodised aluminium. The heater plate 6250 may comprise a heating element 6260. The heating element 6260 may comprise a heat generating component such as an electrically resistive heating track. One suitable example of a heating element is a layered heating element such as one described in the PCT Patent Application Publication No. WO 2012/171072, which is incorporated herewith by reference in its entirety.

5.6.2.10 Humidifier Controller

According to one arrangement of the present technology, a humidifier may comprise a humidifier controller 5250 as shown in FIG. 5B. In one form, the humidifier controller 5250 may be a part of the central controller 4230. In another form, the humidifier controller 5250 may be a separate controller, which may be in communication with the central controller 4230.

In one form, the humidifier controller 5250 may receive as inputs measures of properties (such as temperature, humidity, pressure and/or flow rate), for example of the flow of air, the water in the reservoir 5110 and/or the humidifier 5000. The humidifier controller 5250 may also be configured to execute or implement humidifier algorithms and/or deliver one or more output signals.

As shown in FIG. 5B, the humidifier controller 5250 may comprise one or more controllers, such as a central humidifier controller 5251, a heated air circuit controller 5254 configured to control the temperature of a heated air circuit 4171 and/or a heating element controller 5252 configured to control the temperature of a heating element 5240.

5.7 Glossary

For the purposes of the present technology disclosure, in certain forms of the present technology, one or more of the following definitions may apply. In other forms of the present technology, alternative definitions may apply.

5.7.1 General

Air: In certain forms of the present technology, air may be taken to mean atmospheric air, and in other forms of the present technology air may be taken to mean some other combination of breathable gases, e.g. atmospheric air enriched with oxygen.

Ambient: In certain forms of the present technology, the term ambient will be taken to mean (i) external of the treatment system or patient, and (ii) immediately surrounding the treatment system or patient.

For example, ambient humidity with respect to a humidifier may be the humidity of air immediately surrounding the humidifier, e.g. the humidity in the room where a patient is sleeping. Such ambient humidity may be different to the humidity outside the room where a patient is sleeping.

In another example, ambient pressure may be the pressure immediately surrounding or external to the body.

In certain forms, ambient (e.g., acoustic) noise may be considered to be the background noise level in the room where a patient is located, other than for example, noise generated by an RPT device or emanating from a mask or patient interface. Ambient noise may be generated by sources outside the room.

Automatic Positive Airway Pressure (APAP) therapy: CPAP therapy in which the treatment pressure is automatically adjustable, e.g. from breath to breath, between minimum and maximum limits, depending on the presence or absence of indications of SDB events.

Continuous Positive Airway Pressure (CPAP) therapy: Respiratory pressure therapy in which the treatment pressure is approximately constant through a respiratory cycle of a patient. In some forms, the pressure at the entrance to the airways will be slightly higher during exhalation, and slightly lower during inhalation. In some forms, the pressure will vary between different respiratory cycles of the patient, for example, being increased in response to detection of indications of partial upper airway obstruction, and decreased in the absence of indications of partial upper airway obstruction.

Flow rate: The volume (or mass) of air delivered per unit time. Flow rate may refer to an instantaneous quantity. In some cases, a reference to flow rate will be a reference to a scalar quantity, namely a quantity having magnitude only. In other cases, a reference to flow rate will be a reference to a vector quantity, namely a quantity having both magnitude and direction. Flow rate may be given the symbol Q. 'Flow rate' is sometimes shortened to simply 'flow' or 'airflow'.

In the example of patient respiration, a flow rate may be nominally positive for the inspiratory portion of a breathing cycle of a patient, and hence negative for the expiratory portion of the breathing cycle of a patient. Total flow rate, Qt, is the flow rate of air leaving the RPT device. Vent flow rate, Qv, is the flow rate of air leaving a vent to allow washout of exhaled gases. Leak flow rate, Ql, is the flow rate of leak from a patient interface system or elsewhere. Respiratory flow rate, Qr, is the flow rate of air that is received into the patient's respiratory system.

Humidifier: The word humidifier will be taken to mean a humidifying apparatus constructed and arranged, or configured with a physical structure to be capable of providing a therapeutically beneficial amount of water ($H_2O$) vapour to a flow of air to ameliorate a medical respiratory condition of a patient.

Leak: The word leak will be taken to be an unintended flow of air. In one example, leak may occur as the result of an incomplete seal between a mask and a patient's face. In another example leak may occur in a swivel elbow to the ambient.

Noise, conducted (acoustic): Conducted noise in the present document refers to noise which is carried to the patient by the pneumatic path, such as the air circuit and the patient interface as well as the air therein. In one form, conducted noise may be quantified by measuring sound pressure levels at the end of an air circuit.

Noise, radiated (acoustic): Radiated noise in the present document refers to noise which is carried to the patient by the ambient air. In one form, radiated noise may be quantified by measuring sound power/pressure levels of the object in question according to ISO 3744.

Noise, vent (acoustic): Vent noise in the present document refers to noise which is generated by the flow of air through any vents such as vent holes of the patient interface.

Patient: A person, whether or not they are suffering from a respiratory condition.

Pressure: Force per unit area. Pressure may be expressed in a range of units, including $cmH_2O$, $g$-$f/cm^2$ and hectopascal. 1 $cmH_2O$ is equal to 1 $g$-$f/cm^2$ and is approximately 0.98 hectopascal. In this specification, unless otherwise stated, pressure is given in units of $cmH_2O$.

The pressure in the patient interface is given the symbol Pm, while the treatment pressure, which represents a target value to be achieved by the mask pressure Pm at the current instant of time, is given the symbol Pt.

Respiratory Pressure Therapy (RPT): The application of a supply of air to an entrance to the airways at a treatment pressure that is typically positive with respect to atmosphere.

Ventilator: A mechanical device that provides pressure support to a patient to perform some or all of the work of breathing.

5.7.1.1 Materials

Silicone or Silicone Elastomer: A synthetic rubber. In this specification, a reference to silicone is a reference to liquid silicone rubber (LSR) or a compression moulded silicone rubber (CMSR). One form of commercially available LSR is SILASTIC (included in the range of products sold under this trademark), manufactured by Dow Corning. Another manufacturer of LSR is Wacker. Unless otherwise specified to the contrary, an exemplary form of LSR has a Shore A (or Type A) indentation hardness in the range of about 35 to about 45 as measured using ASTM D2240. (Year? Required?)

Polycarbonate: a thermoplastic polymer of Bisphenol-A Carbonate.

5.7.1.2 Mechanical Properties

Resilience: Ability of a material to absorb energy when deformed elastically and to release the energy upon unloading.

Resilient: Will release substantially all of the energy when unloaded. Includes e.g. certain silicones, and thermoplastic elastomers.

Hardness: The ability of a material per se to resist deformation (e.g. described by a Young's Modulus, or an indentation hardness scale measured on a standardised sample size).

'Soft' materials may include silicone or thermo-plastic elastomer (TPE), and may, e.g. readily deform under finger pressure.

'Hard' materials may include polycarbonate, polypropylene, steel or aluminium, and may not e.g. readily deform under finger pressure.

Stiffness (or rigidity) of a structure or component: The ability of the structure or component to resist deformation in response to an applied load. The load may be a force or a moment, e.g. compression, tension, bending or torsion. The structure or component may offer different resistances in different directions.

Floppy structure or component: A structure or component that will change shape, e.g. bend, when caused to support its own weight, within a relatively short period of time such as 1 second.

Rigid structure or component: A structure or component that will not substantially change shape when subject to the loads typically encountered in use. An example of such a use may be setting up and maintaining a patient interface in sealing relationship with an entrance to a patient's airways, e.g. at a load of approximately 20 to 30 $cmH_2O$ pressure.

As an example, an I-beam may comprise a different bending stiffness (resistance to a bending load) in a first direction in comparison to a second, orthogonal direction. In another example, a structure or component may be floppy in a first direction and rigid in a second direction.

5.7.2 Respiratory Cycle

Apnea: According to some definitions, an apnea is said to have occurred when flow falls below a predetermined threshold for a duration, e.g. 10 seconds. An obstructive apnea will be said to have occurred when, despite patient effort, some obstruction of the airway does not allow air to flow. A central apnea will be said to have occurred when an apnea is detected that is due to a reduction in breathing effort, or the absence of breathing effort, despite the airway being patent. A mixed apnea occurs when a reduction or absence of breathing effort coincides with an obstructed airway.

Breathing rate: The rate of spontaneous respiration of a patient, usually measured in breaths per minute.

Duty cycle: The ratio of inhalation time, Ti to total breath time, Ttot.

Effort (breathing): The work done by a spontaneously breathing person attempting to breathe.

Expiratory portion of a breathing cycle: The period from the start of expiratory flow to the start of inspiratory flow.

Flow limitation: Flow limitation will be taken to be the state of affairs in a patient's respiration where an increase in effort by the patient does not give rise to a corresponding increase in flow. Where flow limitation occurs during an inspiratory portion of the breathing cycle it may be described as inspiratory flow limitation. Where flow limitation occurs during an expiratory portion of the breathing cycle it may be described as expiratory flow limitation.

Types of flow limited inspiratory waveforms:
(i) Flattened: Having a rise followed by a relatively flat portion, followed by a fall.
(ii) M-shaped: Having two local peaks, one at the leading edge, and one at the trailing edge, and a relatively flat portion between the two peaks.
(iii) Chair-shaped: Having a single local peak, the peak being at the leading edge, followed by a relatively flat portion.
(iv) Reverse-chair shaped: Having a relatively flat portion followed by single local peak, the peak being at the trailing edge.

Hypopnea: According to some definitions, a hypopnea is taken to be a reduction in flow, but not a cessation of flow. In one form, a hypopnea may be said to have occurred when there is a reduction in flow below a threshold rate for a duration. A central hypopnea will be said to have occurred when a hypopnea is detected that is due to a reduction in breathing effort. In one form in adults, either of the following may be regarded as being hypopneas:
(i) a 30% reduction in patient breathing for at least 10 seconds plus an associated 4% desaturation; or
(ii) a reduction in patient breathing (but less than 50%) for at least 10 seconds, with an associated desaturation of at least 3% or an arousal.

Hyperpnea: An increase in flow to a level higher than normal.

Inspiratory portion of a breathing cycle: The period from the start of inspiratory flow to the start of expiratory flow will be taken to be the inspiratory portion of a breathing cycle.

Patency (airway): The degree of the airway being open, or the extent to which the airway is open. A patent airway is open. Airway patency may be quantified, for example with a value of one (1) being patent, and a value of zero (0), being closed (obstructed).

Positive End-Expiratory Pressure (PEEP): The pressure above atmosphere in the lungs that exists at the end of expiration.

Peak flow rate (Qpeak): The maximum value of flow rate during the inspiratory portion of the respiratory flow waveform.

Respiratory flow rate, patient airflow rate, respiratory airflow rate (Qr): These terms may be understood to refer to the RPT device's estimate of respiratory flow rate, as opposed to "true respiratory flow rate" or "true respiratory flow rate", which is the actual respiratory flow rate experienced by the patient, usually expressed in litres per minute.

Tidal volume (Vt): The volume of air inhaled or exhaled during normal breathing, when extra effort is not applied.

(inhalation) Time (Ti): The duration of the inspiratory portion of the respiratory flow rate waveform.

(exhalation) Time (Te): The duration of the expiratory portion of the respiratory flow rate waveform.

(total) Time (Ttot): The total duration between the start of one inspiratory portion of a respiratory flow rate waveform and the start of the following inspiratory portion of the respiratory flow rate waveform.

Typical recent ventilation: The value of ventilation around which recent values of ventilation Vent over some predetermined timescale tend to cluster, that is, a measure of the central tendency of the recent values of ventilation.

Upper airway obstruction (UAO): includes both partial and total upper airway obstruction. This may be associated with a state of flow limitation, in which the flow rate increases only slightly or may even decrease as the pressure difference across the upper airway increases (Starling resistor behaviour).

Ventilation (Vent): A measure of a rate of gas being exchanged by the patient's respiratory system. Measures of ventilation may include one or both of inspiratory and expiratory flow, per unit time. When expressed as a volume per minute, this quantity is often referred to as "minute ventilation". Minute ventilation is sometimes given simply as a volume, understood to be the volume per minute.

5.7.3 Ventilation

Adaptive Servo-Ventilator (ASV): A servo-ventilator that has a changeable, rather than fixed target ventilation. The changeable target ventilation may be learned from some characteristic of the patient, for example, a respiratory characteristic of the patient.

Backup rate: A parameter of a ventilator that establishes the minimum breathing rate (typically in number of breaths per minute) that the ventilator will deliver to the patient, if not triggered by spontaneous respiratory effort.

Cycled: The termination of a ventilator's inspiratory phase. When a ventilator delivers a breath to a spontaneously breathing patient, at the end of the inspiratory portion of the breathing cycle, the ventilator is said to be cycled to stop delivering the breath.

Expiratory positive airway pressure (EPAP): a base pressure, to which a pressure varying within the breath is added to produce the desired mask pressure which the ventilator will attempt to achieve at a given time.

End expiratory pressure (EEP): Desired mask pressure which the ventilator will attempt to achieve at the end of the expiratory portion of the breath. If the pressure waveform template $\Pi(\Phi)$ is zero-valued at the end of expiration, i.e. $\Pi(\Phi)=0$ when $\Phi=1$, the EEP is equal to the EPAP.

Inspiratory positive airway pressure (IPAP): Maximum desired mask pressure which the ventilator will attempt to achieve during the inspiratory portion of the breath.

Pressure support: A number that is indicative of the increase in pressure during ventilator inspiration over that during ventilator expiration, and generally means the difference in pressure between the maximum value during inspiration and the base pressure (e.g., PS=IPAP−EPAP). In some contexts pressure support means the difference which the ventilator aims to achieve, rather than what it actually achieves.

Servo-ventilator: A ventilator that measures patient ventilation, has a target ventilation, and which adjusts the level of pressure support to bring the patient ventilation towards the target ventilation.

Spontaneous/Timed (S/T): A mode of a ventilator or other device that attempts to detect the initiation of a breath of a spontaneously breathing patient. If however, the device is unable to detect a breath within a predetermined period of time, the device will automatically initiate delivery of the breath.

Swing: Equivalent term to pressure support.

Triggered: When a ventilator delivers a breath of air to a spontaneously breathing patient, it is said to be triggered to do so at the initiation of the respiratory portion of the breathing cycle by the patient's efforts.

Typical recent ventilation: The typical recent ventilation Vtyp is the value around which recent measures of ventilation over some predetermined timescale tend to cluster. For example, a measure of the central tendency of the measures of ventilation over recent history may be a suitable value of a typical recent ventilation.

5.7.4 Patient Interface

Anti-asphyxia valve (AAV): The component or sub-assembly of a mask system that, by opening to atmosphere in a failsafe manner, reduces the risk of excessive $CO_2$ rebreathing by a patient.

Elbow: An elbow is an example of a structure that directs an axis of flow of air travelling therethrough to change direction through an angle. In one form, the angle may be approximately 90 degrees. In another form, the angle may be more, or less than 90 degrees. The elbow may have an approximately circular cross-section. In another form the elbow may have an oval or a rectangular cross-section. In certain forms an elbow may be rotatable with respect to a mating component, e.g. about 360 degrees. In certain forms an elbow may be removable from a mating component, e.g. via a snap connection. In certain forms, an elbow may be assembled to a mating component via a one-time snap during manufacture, but not removable by a patient.

Frame: Frame will be taken to mean a mask structure that bears the load of tension between two or more points of connection with a headgear. A mask frame may be a non-airtight load bearing structure in the mask. However, some forms of mask frame may also be air-tight.

Functional dead space: (description to be inserted here)

Headgear: Headgear will be taken to mean a form of positioning and stabilizing structure designed for use on a head. For example the headgear may comprise a collection of one or more struts, ties and stiffeners configured to locate and retain a patient interface in position on a patient's face for delivery of respiratory therapy. Some ties are formed of a soft, flexible, elastic material such as a laminated composite of foam and fabric.

Membrane: Membrane will be taken to mean a typically thin element that has, preferably, substantially no resistance to bending, but has resistance to being stretched.

Plenum chamber: a mask plenum chamber will be taken to mean a portion of a patient interface having walls at least partially enclosing a volume of space, the volume having air therein pressurised above atmospheric pressure in use. A shell may form part of the walls of a mask plenum chamber.

Seal: May be a noun form ("a seal") which refers to a structure, or a verb form ("to seal") which refers to the effect. Two elements may be constructed and/or arranged to 'seal' or to effect 'sealing' therebetween without requiring a separate 'seal' element per se.

Shell: A shell will be taken to mean a curved, relatively thin structure having bending, tensile and compressive stiffness. For example, a curved structural wall of a mask may be a shell. In some forms, a shell may be faceted. In some forms a shell may be airtight. In some forms a shell may not be airtight.

Stiffener: A stiffener will be taken to mean a structural component designed to increase the bending resistance of another component in at least one direction.

Strut: A strut will be taken to be a structural component designed to increase the compression resistance of another component in at least one direction.

Swivel (noun): A subassembly of components configured to rotate about a common axis, preferably independently, preferably under low torque. In one form, the swivel may be constructed to rotate through an angle of at least 360 degrees. In another form, the swivel may be constructed to rotate through an angle less than 360 degrees. When used in the context of an air delivery conduit, the sub-assembly of components preferably comprises a matched pair of cylindrical conduits. There may be little or no leak flow of air from the swivel in use.

Tie (noun): A structure designed to resist tension.

Vent: (noun): A structure that allows a flow of air from an interior of the mask, or conduit, to ambient air for clinically effective washout of exhaled gases. For example, a clinically effective washout may involve a flow rate of about 10 litres per minute to about 100 litres per minute, depending on the mask design and treatment pressure.

5.7.5 Shape of Structures

Products in accordance with the present technology may comprise one or more three-dimensional mechanical structures, for example a mask cushion or an impeller. The three-dimensional structures may be bounded by two-dimensional surfaces. These surfaces may be distinguished using a label to describe an associated surface orientation, location, function, or some other characteristic. For example a structure may comprise one or more of an anterior surface, a posterior surface, an interior surface and an exterior surface. In another example, a seal-forming structure may comprise a face-contacting (e.g. outer) surface, and a separate non-face-contacting (e.g. underside or inner) surface. In another example, a structure may comprise a first surface and a second surface.

To facilitate describing the shape of the three-dimensional structures and the surfaces, we first consider a cross-section through a surface of the structure at a point, p. See FIG. 3B to FIG. 3F, which illustrate examples of cross-sections at point p on a surface, and the resulting plane curves. FIGS. 3B to 3F also illustrate an outward normal vector at p. The outward normal vector at p points away from the surface. In some examples we describe the surface from the point of view of an imaginary small person standing upright on the surface.

5.7.5.1 Curvature in One Dimension

The curvature of a plane curve at p may be described as having a sign (e.g. positive, negative) and a magnitude (e.g. 1/radius of a circle that just touches the curve at p).

Positive curvature: If the curve at p turns towards the outward normal, the curvature at that point will be taken to be positive (if the imaginary small person leaves the point p they must walk uphill). See FIG. 3B (relatively large positive curvature compared to FIG. 3C) and FIG. 3C (relatively small positive curvature compared to FIG. 3B). Such curves are often referred to as concave.

Zero curvature: If the curve at p is a straight line, the curvature will be taken to be zero (if the imaginary small person leaves the point p, they can walk on a level, neither up nor down). See FIG. 3D.

Negative curvature: If the curve at p turns away from the outward normal, the curvature in that direction at that point will be taken to be negative (if the imaginary small person leaves the point p they must walk downhill). See FIG. 3E (relatively small negative curvature compared to FIG. 3F) and FIG. 3F (relatively large negative curvature compared to FIG. 3E). Such curves are often referred to as convex.

5.7.5.2 Curvature of Two Dimensional Surfaces

A description of the shape at a given point on a two-dimensional surface in accordance with the present technology may include multiple normal cross-sections. The multiple cross-sections may cut the surface in a plane that includes the outward normal (a "normal plane"), and each cross-section may be taken in a different direction. Each cross-section results in a plane curve with a corresponding curvature. The different curvatures at that point may have the same sign, or a different sign. Each of the curvatures at that point has a magnitude, e.g. relatively small. The plane curves in FIGS. 3B to 3F could be examples of such multiple cross-sections at a particular point.

Principal curvatures and directions: The directions of the normal planes where the curvature of the curve takes its maximum and minimum values are called the principal directions. In the examples of FIG. 3B to FIG. 3F, the maximum curvature occurs in FIG. 3B, and the minimum occurs in FIG. 3F, hence FIG. 3B and FIG. 3F are cross sections in the principal directions. The principal curvatures at p are the curvatures in the principal directions.

Region of a surface: A connected set of points on a surface. The set of points in a region may have similar characteristics, e.g. curvatures or signs.

Saddle region: A region where at each point, the principal curvatures have opposite signs, that is, one is positive, and the other is negative (depending on the direction to which the imaginary person turns, they may walk uphill or downhill).

Dome region: A region where at each point the principal curvatures have the same sign, e.g. both positive (a "concave dome") or both negative (a "convex dome").

Cylindrical region: A region where one principal curvature is zero (or, for example, zero within manufacturing tolerances) and the other principal curvature is non-zero.

Planar region: A region of a surface where both of the principal curvatures are zero (or, for example, zero within manufacturing tolerances).

Edge of a surface: A boundary or limit of a surface or region.

Path: In certain forms of the present technology, 'path' will be taken to mean a path in the mathematical—topological sense, e.g. a continuous space curve from f(0) to f(1) on a surface. In certain forms of the present technology, a 'path' may be described as a route or course, including e.g. a set of points on a surface. (The path for the imaginary person is where they walk on the surface, and is analogous to a garden path).

Path length: In certain forms of the present technology, 'path length' will be taken to mean the distance along the surface from f(0) to f(1), that is, the distance along the path on the surface. There may be more than one path between two points on a surface and such paths may have different path lengths. (The path length for the imaginary person would be the distance they have to walk on the surface along the path).

Straight-line distance: The straight-line distance is the distance between two points on a surface, but without regard to the surface. On planar regions, there would be a path on the surface having the same path length as the straight-line distance between two points on the surface. On non-planar surfaces, there may be no paths having the same path length as the straight-line distance between two points. (For the imaginary person, the straight-line distance would correspond to the distance 'as the crow flies'.)

5.7.5.3 Space Curves

Space curves: Unlike a plane curve, a space curve does not necessarily lie in any particular plane. A space curve may be closed, that is, having no endpoints. A space curve may be considered to be a one-dimensional piece of three-dimensional space. An imaginary person walking on a strand of the DNA helix walks along a space curve. A typical human left ear comprises a helix, which is a left-hand helix, see FIG. 3Q. A typical human right ear comprises a helix, which is a right-hand helix, see FIG. 3R. FIG. 3S shows a right-hand helix. The edge of a structure, e.g. the edge of a membrane or impeller, may follow a space curve. In general, a space curve may be described by a curvature and a torsion at each point on the space curve. Torsion is a measure of how the curve turns out of a plane. Torsion has a sign and a magnitude. The torsion at a point on a space curve may be characterised with reference to the tangent, normal and binormal vectors at that point.

Tangent unit vector (or unit tangent vector): For each point on a curve, a vector at the point specifies a direction from that point, as well as a magnitude. A tangent unit vector is a unit vector pointing in the same direction as the curve at that point. If an imaginary person were flying along the curve and fell off her vehicle at a particular point, the direction of the tangent vector is the direction she would be travelling.

Unit normal vector: As the imaginary person moves along the curve, this tangent vector itself changes. The unit vector pointing in the same direction that the tangent vector is changing is called the unit principal normal vector. It is perpendicular to the tangent vector.

Binormal unit vector: The binormal unit vector is perpendicular to both the tangent vector and the principal normal vector. Its direction may be determined by a right-hand rule (see e.g. FIG. 3P), or alternatively by a left-hand rule (FIG. 3O).

Osculating plane: The plane containing the unit tangent vector and the unit principal normal vector. See FIGS. 3O and 3P.

Torsion of a space curve: The torsion at a point of a space curve is the magnitude of the rate of change of the binormal unit vector at that point. It measures how much the curve deviates from the osculating plane. A space curve which lies in a plane has zero torsion. A space curve which deviates a relatively small amount from the osculating plane will have a relatively small magnitude of torsion (e.g. a gently sloping helical path). A space curve which deviates a relatively large amount from the osculating plane will have a relatively large magnitude of torsion (e.g. a steeply sloping helical path). With reference to FIG. 3S, since T2>T1, the magnitude of the torsion near the top coils of the helix of FIG. 3S is greater than the magnitude of the torsion of the bottom coils of the helix of FIG. 3S With reference to the right-hand rule of FIG. 3P, a space curve turning towards the direction of the right-hand binormal may be considered as having a right-hand positive torsion (e.g. a right-hand helix as shown in FIG. 3S). A space curve turning away from the direction of the right-hand binormal may be considered as having a right-hand negative torsion (e.g. a left-hand helix).

Equivalently, and with reference to a left-hand rule (see FIG. 3O), a space curve turning towards the direction of the left-hand binormal may be considered as having a left-hand positive torsion (e.g. a left-hand helix). Hence left-hand positive is equivalent to right-hand negative. See FIG. 3T.

5.7.5.4 Holes

A surface may have a one-dimensional hole, e.g. a hole bounded by a plane curve or by a space curve. Thin structures (e.g. a membrane) with a hole, may be described as having a one-dimensional hole. See for example the one dimensional hole in the surface of structure shown in FIG. 3I, bounded by a plane curve.

A structure may have a two-dimensional hole, e.g. a hole bounded by a surface. For example, an inflatable tyre has a two dimensional hole bounded by the interior surface of the tyre. In another example, a bladder with a cavity for air or gel could have a two-dimensional hole. See for example the cushion of FIG. 3L and the example cross-sections therethrough in FIG. 3M and FIG. 3N, with the interior surface bounding a two dimensional hole indicated. In a yet another example, a conduit may comprise a one-dimension hole (e.g. at its entrance or at its exit), and a two-dimension hole bounded by the inside surface of the conduit. See also the two dimensional hole through the structure shown in FIG. 3K, bounded by a surface as shown.

5.8 Other Remarks

A portion of the disclosure of this patent document contains material which is subject to copyright protection. The copyright owner has no objection to the facsimile reproduction by anyone of the patent document or the patent disclosure, as it appears in Patent Office patent files or records, but otherwise reserves all copyright rights whatsoever.

Unless the context clearly dictates otherwise and where a range of values is provided, it is understood that each intervening value, to the tenth of the unit of the lower limit, between the upper and lower limit of that range, and any other stated or intervening value in that stated range is encompassed within the technology. The upper and lower limits of these intervening ranges, which may be independently included in the intervening ranges, are also encompassed within the technology, subject to any specifically excluded limit in the stated range. Where the stated range includes one or both of the limits, ranges excluding either or both of those included limits are also included in the technology.

Furthermore, where a value or values are stated herein as being implemented as part of the technology, it is understood that such values may be approximated, unless otherwise stated, and such values may be utilized to any suitable significant digit to the extent that a practical technical implementation may permit or require it.

Unless defined otherwise, all technical and scientific terms used herein have the same meaning as commonly understood by one of ordinary skill in the art to which this technology belongs. Although any methods and materials similar or equivalent to those described herein can also be used in the practice or testing of the present technology, a limited number of the exemplary methods and materials are described herein.

When a particular material is identified as being used to construct a component, obvious alternative materials with similar properties may be used as a substitute. Furthermore, unless specified to the contrary, any and all components herein described are understood to be capable of being manufactured and, as such, may be manufactured together or separately.

It must be noted that as used herein and in the appended claims, the singular forms "a", "an", and "the" include their plural equivalents, unless the context clearly dictates otherwise.

All publications mentioned herein are incorporated herein by reference in their entirety to disclose and describe the methods and/or materials which are the subject of those publications. The publications discussed herein are provided solely for their disclosure prior to the filing date of the present application. Nothing herein is to be construed as an admission that the present technology is not entitled to antedate such publication by virtue of prior invention. Further, the dates of publication provided may be different from the actual publication dates, which may need to be independently confirmed.

The terms "comprises" and "comprising" should be interpreted as referring to elements, components, or steps in a non-exclusive manner, indicating that the referenced elements, components, or steps may be present, or utilized, or combined with other elements, components, or steps that are not expressly referenced.

The subject headings used in the detailed description are included only for the ease of reference of the reader and should not be used to limit the subject matter found throughout the disclosure or the claims. The subject headings should not be used in construing the scope of the claims or the claim limitations.

Although the technology herein has been described with reference to particular examples, it is to be understood that these examples are merely illustrative of the principles and applications of the technology. In some instances, the terminology and symbols may imply specific details that are not required to practice the technology. For example, although the terms "first" and "second" may be used, unless otherwise specified, they are not intended to indicate any order but may be utilised to distinguish between distinct elements. Furthermore, although process steps in the methodologies may be described or illustrated in an order, such an ordering is not required. Those skilled in the art will recognize that such ordering may be modified and/or aspects thereof may be conducted concurrently or even synchronously.

It is therefore to be understood that numerous modifications may be made to the illustrative examples and that other arrangements may be devised without departing from the spirit and scope of the technology.

5.9 Reference Signs List

| | |
|---|---|
| patient | 1000 |
| bed partner | 1100 |
| patient interface | 3000 |
| seal-forming structure | 3100 |
| plenum chamber | 3200 |
| positioning and stablising structure | 3300 |
| vent | 3400 |
| connection port | 3600 |
| forehead support | 3700 |
| RPT device | 4000 |
| external housing | 4010 |
| upper portion | 4012 |
| lower portion | 4014 |
| panel | 4015 |
| chassis | 4016 |
| handle | 4018 |
| pneumatic block | 4020 |
| air filter | 4110 |
| inlet air filter | 4112 |
| outlet air filter | 4114 |
| muffler | 4120 |
| inlet muffler | 4122 |
| outlet muffler | 4124 |
| pressure generator | 4140 |
| blower | 4142 |
| motor | 4144 |
| anti-spillback valve | 4160 |
| air circuit | 4170 |
| air circuit | 4171 |
| supplemental oxygen | 4180 |
| electrical component | 4200 |
| PCBA | 4202 |
| power supply | 4210 |

| | |
|---|---|
| input device | 4220 |
| central controller | 4230 |
| clock | 4232 |
| therapy device controller | 4240 |
| protection circuit | 4250 |
| memory | 4260 |
| transducer | 4270 |
| pressure sensor | 4272 |
| flow rate sensor | 4274 |
| motor speed transducer | 4276 |
| data communication interface | 4280 |
| remote external communication network | 4282 |
| local external communication network | 4284 |
| remote external device | 4286 |
| local external device | 4288 |
| output device | 4290 |
| display driver | 4292 |
| display | 4294 |
| algorithm | 4300 |
| pre-processing module | 4310 |
| pressure compensation algorithm | 4312 |
| vent flow rate estimation algorithm | 4314 |
| leak flow rate estimation algorithm | 4316 |
| respiratory flow rate estimation algorithm | 4318 |
| therapy engine module | 4320 |
| phase determination algorithm | 4321 |
| waveform determination algorithm | 4322 |
| ventilation determination algorithm | 4323 |
| flow limitation determination algorithm | 4324 |
| apnea/hypopnea determination algorithm | 4325 |
| snore determination algorithm | 4326 |
| airway patency determination algorithm | 4327 |
| target ventilation determination algorithm | 4328 |
| therapy parameter determination algorithm | 4329 |
| therapy control module | 4330 |
| Fault condition detection | 4340 |
| humidifier | 5000 |
| humidifier outlet | 5004 |
| reservoir | 5110 |
| sensor | 5210 |
| air pressure sensor | 5212 |
| air flow rate transducer | 5214 |
| temperature sensor | 5216 |
| humidity sensor | 5218 |
| heating element | 5240 |
| humidifier controller | 5250 |
| central humidifier controller | 5251 |
| heating element controller | 5252 |
| air circuit controller | 5254 |
| humidifier | 6000 |
| reservoir dock | 6100 |
| main body | 6200 |
| cavity | 6210 |
| heater plate | 6250 |
| heating element | 6260 |
| dock inlet conduit | 6300 |
| outer end portion | 6310 |
| outer opening | 6315 |
| inner end portion | 6320 |
| inner opening | 6325 |
| dock outlet conduit | 6400 |
| outer end portion | 6410 |
| inner end portion | 6420 |
| conduit portion | 6450 |
| lip | 6455 |
| water reservoir | 6500 |
| dock engagement portion | 6505 |
| protrusion | 6510 |
| rail | 6520 |
| recess | 6530 |
| reservoir base | 6600 |
| base mold | 6600A |
| overmold | 6600B |
| conductive portion | 6650 |
| chamber | 6660 |
| opening | 6665 |
| rim | 6670 |
| wall portion | 6675 |
| annular wall | 6680 |
| reservoir lid | 6700 |
| lid portion | 6710 |
| single conduit | 6720 |
| outer end portion | 6730 |
| outer opening | 6735 |
| inner end portion | 6740 |
| inner opening | 6745 |
| seal | 6750 |
| seal | 6760 |
| wing portion | 6770 |
| locking tab | 6775 |
| baffle plate | 6800 |
| inlet opening | 6810 |
| gap | 6815 |
| upper surface | 6820 |
| RPT device | 7000 |
| external housing | 7010 |
| blower | 7100 |
| blower inlet | 7105 |
| blower outlet | 7110 |
| release button | 7200 |

The invention claimed is:

1. A medical treatment apparatus for providing a supply of pressurized breathable air to a patient in a positive pressure range suitable for treatment of a respiratory disorder, the medical treatment apparatus comprising:
   a blower configured to pressurize the supply of pressurized breathable air in the positive pressure range;
   a water reservoir including a cavity structured to hold a volume of water to humidify the supply of pressurized breathable air, the water reservoir including a heat conductive portion;
   a water reservoir dock including a cavity configured and arranged to receive at least an end portion of the water reservoir in an operative position, the water reservoir dock including a heater plate adapted to thermally engage the heat conductive portion of the water reservoir in the operative position to allow thermal transfer of heat from the heater plate to the volume of water; and
   an overlapping conduit arrangement configured and arranged to provide an inlet for a flow of pressurized breathable air entering the cavity of the water reservoir and an outlet for a flow of humidified, pressurized breathable air exiting the cavity of the water reservoir when the water reservoir is in the operative position,
   wherein the overlapping conduit arrangement includes a first conduit and a second conduit, the first conduit configured and arranged to at least partially extend within the second conduit when the water reservoir is in the operative position,
   wherein the first conduit includes an interior surface that forms an inlet flow path for the flow of pressurized breathable air entering the cavity of the water reservoir, and the first conduit includes an exterior surface that cooperates with an interior surface of the second conduit to form an outlet flow path for the flow of humidified, pressurized breathable air exiting the cavity of the water reservoir,
   wherein the water reservoir further comprises a baffle plate configured and arranged to direct at least a portion of the air exiting the cavity of the water reservoir to the outlet,
   wherein the water reservoir includes a bottom surface forming a bottom plane that is substantially horizontal when the water reservoir is in the operative position, and wherein the baffle plate extends substantially parallel to the bottom plane.

2. The medical treatment apparatus according to claim 1, wherein the first conduit is configured to receive the flow of pressurized breathable air from the blower.

3. The medical treatment apparatus according to claim 1, wherein the first conduit includes an inner opening arranged within the cavity of the water reservoir.

4. The medical treatment apparatus according to claim 3, wherein the inner opening of the first conduit is arranged at or near a geometric center of the cavity of the water reservoir.

5. The medical treatment apparatus according to claim 1, wherein the water reservoir includes a reservoir base and a reservoir lid removably coupled to the reservoir base.

6. The medical treatment apparatus according to claim 5, further comprising a seal configured and arranged to form a seal between the reservoir base and the reservoir lid when the reservoir lid is coupled to the reservoir base.

7. The medical treatment apparatus according to claim 1, wherein the first conduit and the second conduit each include a non-circular cross-sectional shape.

8. The medical treatment apparatus according to claim 7, wherein at least a portion of the first conduit comprises a square cross-sectional shape.

9. The medical treatment apparatus according to claim 1, further comprising a seal configured and arranged to form a seal between the water reservoir and the water reservoir dock when the water reservoir is in the operative position.

10. The medical treatment apparatus according to claim 9, wherein the seal is configured to form a face seal along at least a portion of the outlet flow path.

11. The medical treatment apparatus according to claim 1, wherein the baffle plate is configured and arranged to encourage air entering the cavity of the water reservoir to flow into contact with the water.

12. The medical treatment apparatus according to claim 1, wherein each of the first conduit and the second conduit includes an axis that is substantially parallel to the bottom plane.

13. The medical treatment apparatus according to claim 1, wherein the first conduit includes an inner opening arranged within the cavity of the water reservoir and outer opening arranged in a wall of the water reservoir, wherein each of the inner opening and the outer opening includes an axis, and wherein the axis of the inner opening is generally perpendicular to the axis of the outer opening.

14. The medical treatment apparatus according to claim 13, wherein the axis of the inner opening is generally perpendicular to the bottom plane.

15. The medical treatment apparatus according to claim 1, wherein the water reservoir is configured to removably couple with the water reservoir dock in a lateral direction.

16. The medical treatment apparatus according to claim 1, further comprising a retainer configured and arranged to releasably retain the water reservoir when the water reservoir is in the operative position.

17. The medical treatment apparatus according to claim 1, wherein the first conduit is configured to receive the flow of pressurized breathable air from the blower,
wherein the first conduit includes an inner opening arranged within the cavity of the water reservoir,
wherein the water reservoir includes a reservoir base and a reservoir lid removably coupled to the reservoir base,
further comprising a seal configured and arranged to form a seal between the reservoir base and the reservoir lid when the reservoir lid is coupled to the reservoir base,
wherein the first conduit and the second conduit each include a non-circular cross-sectional shape,
wherein at least a portion of the first conduit comprises a square cross-sectional shape,
further comprising a seal configured and arranged to form a seal between the water reservoir and the water reservoir dock when the water reservoir is in the operative position,
wherein the water reservoir is configured to removably couple with the water reservoir dock in a lateral direction, and
further comprising a retainer configured and arranged to releasably retain the water reservoir when the water reservoir is in the operative position.

18. The medical treatment apparatus according to claim 1, wherein the baffle plate includes a first side and a second side that is opposite to the first side, and wherein the first conduit and the second conduit are both arranged adjacent the first side.

19. The medical treatment apparatus according to claim 1, wherein the baffle plate includes planar configuration having a planar surface that extends substantially parallel to the bottom plane when the water reservoir is in the operative position,
wherein the planar surface is arranged along an inlet end of the outlet flow path formed by the second conduit to direct the flow of humidified, pressurized breathable air to the outlet flow path,
wherein the second conduit includes an axis that is substantially parallel to the bottom plane, and
wherein the planar surface extends substantially parallel to the bottom plane.

* * * * *